US010888369B2

(12) United States Patent
Messerly et al.

(10) Patent No.: US 10,888,369 B2
(45) Date of Patent: Jan. 12, 2021

(54) SYSTEMS AND METHODS FOR CONTROLLING CONTROL CIRCUITS FOR INDEPENDENT ENERGY DELIVERY OVER SEGMENTED SECTIONS

(71) Applicant: Ethicon LLC, Guaynabo, PR (US)

(72) Inventors: Jeffrey D. Messerly, Cincinnati, OH (US); David C. Yates, West Chester, OH (US); Jason L. Harris, Lebanon, OH (US); Frederick E. Shelton, IV, Hillsboro, OH (US); Mark A. Davison, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 556 days.

(21) Appl. No.: 15/636,116

(22) Filed: Jun. 28, 2017

(65) Prior Publication Data
US 2019/0000534 A1    Jan. 3, 2019

(51) Int. Cl.
*A61B 18/14* (2006.01)
*A61B 17/072* (2006.01)
(Continued)

(52) U.S. Cl.
CPC .... *A61B 18/1445* (2013.01); *A61B 17/07207* (2013.01); *A61B 18/1206* (2013.01);
(Continued)

(58) Field of Classification Search
CPC ............. A61B 18/085; A61B 18/1206; A61B 18/1442; A61B 18/1445; A61B 2018/00708; A61B 2018/0063; A61B 2018/00607; A61B 2018/00916; A61B 2018/00922; A61B 2018/124;
(Continued)

(56) References Cited

U.S. PATENT DOCUMENTS 2,961,385 A    11/1960    McGall
3,370,263 A     2/1968    Schreieck
(Continued)

FOREIGN PATENT DOCUMENTS

GB        1526401 A      9/1978
WO    WO-9937225 A1      7/1999

OTHER PUBLICATIONS

Bay Area Circuits (https://bayareacircuits.com/multi-layer-stackups/) (Year: 2015).

*Primary Examiner* — Thomas A Giuliani

(57) ABSTRACT

The present disclosure provides a surgical instrument that includes an end effector having a first jaw, a second jaw that is movable relative to the first jaw, and at least one electrode in the first jaw. The surgical instrument also includes a control circuit configured to provide electrosurgical energy to the at least one electrode and a electrical conductor electrically connected between the end effector and the control circuit. The control circuit includes a shaft control segment and an electrosurgical energy control segment. The shaft control segment is configured to provide a control signal for operating the end effector to the end effector through the electrical conductor. The electrosurgical energy control segment is configured to provide the electrosurgical energy to the at least one electrode through the electrical conductor.

20 Claims, 25 Drawing Sheets

(51) Int. Cl.
*A61B 18/12* (2006.01)
*A61B 17/00* (2006.01)
*A61B 18/00* (2006.01)
*A61B 17/29* (2006.01)
*A61B 90/00* (2016.01)
*A61B 17/295* (2006.01)

(52) U.S. Cl.
CPC ... *A61B 17/295* (2013.01); *A61B 2017/00017* (2013.01); *A61B 2017/00026* (2013.01); *A61B 2017/0046* (2013.01); *A61B 2017/00075* (2013.01); *A61B 2017/00119* (2013.01); *A61B 2017/00128* (2013.01); *A61B 2017/00353* (2013.01); *A61B 2017/00398* (2013.01); *A61B 2017/00464* (2013.01); *A61B 2017/00477* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/2926* (2013.01); *A61B 2017/2927* (2013.01); *A61B 2018/0063* (2013.01); *A61B 2018/00172* (2013.01); *A61B 2018/00178* (2013.01); *A61B 2018/00589* (2013.01); *A61B 2018/00619* (2013.01); *A61B 2018/00642* (2013.01); *A61B 2018/00666* (2013.01); *A61B 2018/00708* (2013.01); *A61B 2018/00755* (2013.01); *A61B 2018/00875* (2013.01); *A61B 2018/00922* (2013.01); *A61B 2018/00988* (2013.01); *A61B 2018/124* (2013.01); *A61B 2018/1452* (2013.01); *A61B 2018/1455* (2013.01); *A61B 2018/1467* (2013.01); *A61B 2090/0808* (2016.02); *A61B 2090/0811* (2016.02)

(58) Field of Classification Search
CPC .... A61B 2018/1452; A61B 2018/1455; A61B 2018/1467; A61B 2018/00178; A61B 17/07207; A61B 17/295; A61B 17/29; A61B 2017/00017; A61B 2017/00353; A61B 2017/0046; A61B 2017/2932
USPC ............. 606/34, 37, 38, 41, 42, 50-52
See application file for complete search history.

(56) References Cited

U.S. PATENT DOCUMENTS

| | | |
|---|---|---|
| D278,081 S | 3/1985 | Green |
| D297,764 S | 9/1988 | Hunt et al. |
| 5,007,907 A | 4/1991 | Nishigaki et al. |
| 5,364,395 A | 11/1994 | West, Jr. |
| 5,403,312 A | 4/1995 | Yates et al. |
| D360,688 S | 7/1995 | Ferragamo et al. |
| 5,485,947 A | 1/1996 | Olson et al. |
| 5,658,281 A | 8/1997 | Heard |
| 5,673,842 A | 10/1997 | Bittner et al. |
| 5,735,848 A | 4/1998 | Yates et al. |
| 5,817,093 A | 10/1998 | Williamson, IV et al. |
| 5,833,690 A | 11/1998 | Yates et al. |
| 5,835,829 A | 11/1998 | Genovese et al. |
| 6,004,320 A | 12/1999 | Casscells et al. |
| D480,808 S | 10/2003 | Wells et al. |
| 6,730,081 B1 | 5/2004 | Desai |
| 6,918,906 B2 | 7/2005 | Long |
| D509,297 S | 9/2005 | Wells |
| 6,988,649 B2 | 1/2006 | Shelton, IV et al. |
| 7,044,352 B2 | 5/2006 | Shelton, IV et al. |
| 7,223,267 B2 | 5/2007 | Isola et al. |
| 7,383,611 B2 | 6/2008 | Foster |
| D576,278 S | 9/2008 | Nalagatla et al. |
| 7,431,720 B2 | 10/2008 | Pendekanti et al. |
| 7,476,222 B2 | 1/2009 | Sun et al. |
| 7,517,356 B2 | 4/2009 | Heinrich |
| 7,575,144 B2 | 8/2009 | Ortiz et al. |
| 7,617,961 B2 | 11/2009 | Viola |
| D605,762 S | 12/2009 | Nalagatla et al. |
| 7,673,781 B2 | 3/2010 | Swayze et al. |
| 7,780,663 B2 | 8/2010 | Yates et al. |
| 7,819,296 B2 | 10/2010 | Hueil et al. |
| 7,861,906 B2 | 1/2011 | Doll et al. |
| 7,896,877 B2 | 3/2011 | Hall et al. |
| 7,901,400 B2 | 3/2011 | Wham et al. |
| D650,074 S | 12/2011 | Hunt et al. |
| 8,277,446 B2 | 10/2012 | Heard |
| 8,453,906 B2 | 6/2013 | Huang et al. |
| 8,485,413 B2 | 7/2013 | Scheib et al. |
| 8,517,239 B2 | 8/2013 | Scheib et al. |
| 8,523,043 B2 | 9/2013 | Ullrich et al. |
| 8,579,176 B2 | 11/2013 | Smith et al. |
| 8,608,045 B2 | 12/2013 | Smith et al. |
| 8,616,431 B2 | 12/2013 | Timm et al. |
| 8,622,274 B2 | 1/2014 | Yates et al. |
| 8,636,736 B2 | 1/2014 | Yates et al. |
| 8,663,222 B2 | 3/2014 | Anderson et al. |
| 8,746,533 B2 | 6/2014 | Whitman et al. |
| 8,764,747 B2 | 7/2014 | Cummings et al. |
| 8,784,415 B2 | 7/2014 | Malackowski et al. |
| 8,820,603 B2 | 9/2014 | Shelton, IV et al. |
| 8,840,603 B2 | 9/2014 | Shelton, IV et al. |
| 8,888,771 B2 | 11/2014 | Twomey |
| 8,888,776 B2 | 11/2014 | Dietz et al. |
| 8,979,890 B2 | 3/2015 | Boudreaux |
| 8,998,060 B2 | 4/2015 | Bruewer et al. |
| 9,005,199 B2 | 4/2015 | Beckman et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,149,325 B2 | 10/2015 | Worrell et al. |
| 9,161,802 B2 | 10/2015 | Przybyszewski |
| 9,326,788 B2 | 5/2016 | Batross et al. |
| 9,345,481 B2 | 5/2016 | Hall et al. |
| 9,358,003 B2 | 6/2016 | Hall et al. |
| 9,402,627 B2 | 8/2016 | Stevenson et al. |
| 9,510,906 B2 | 12/2016 | Boudreaux et al. |
| 9,549,733 B2 | 1/2017 | Knodel |
| 9,572,622 B2 | 2/2017 | Shelton, IV et al. |
| 9,585,657 B2 | 3/2017 | Shelton, IV et al. |
| 9,629,627 B2 | 4/2017 | Kostrzewski et al. |
| 9,629,628 B2 | 4/2017 | Aranyi |
| 9,700,309 B2 | 7/2017 | Jaworek et al. |
| 9,706,993 B2 | 7/2017 | Hessler et al. |
| 9,724,095 B2 | 8/2017 | Gupta et al. |
| 9,743,929 B2 | 8/2017 | Leimbach et al. |
| D800,904 S | 10/2017 | Leimbach et al. |
| 9,788,836 B2 | 10/2017 | Overmyer et al. |
| 9,795,379 B2 | 10/2017 | Leimbach et al. |
| 9,808,246 B2 | 11/2017 | Shelton, IV et al. |
| 9,814,514 B2 | 11/2017 | Shelton, IV et al. |
| 9,839,421 B2 | 12/2017 | Zerkle et al. |
| 9,844,375 B2 | 12/2017 | Overmyer et al. |
| 9,877,722 B2 | 1/2018 | Schellin et al. |
| D809,659 S | 2/2018 | Menn |
| 9,888,958 B2 | 2/2018 | Evans et al. |
| 9,913,642 B2 | 3/2018 | Leimbach et al. |
| 9,924,942 B2 | 3/2018 | Swayze et al. |
| 9,924,944 B2 | 3/2018 | Shelton, IV et al. |
| 9,924,998 B2 | 3/2018 | Martin et al. |
| 9,968,355 B2 | 5/2018 | Shelton, IV et al. |
| 9,980,769 B2 | 5/2018 | Trees et al. |
| 10,010,366 B2 | 7/2018 | Strobl |
| 10,016,186 B2 | 7/2018 | Benn |
| 10,052,100 B2 | 8/2018 | Morgan et al. |
| D831,209 S | 10/2018 | Huitema et al. |
| D836,198 S | 12/2018 | Harris et al. |
| 10,178,992 B2 | 1/2019 | Wise et al. |
| 10,194,912 B2 | 2/2019 | Scheib et al. |
| 10,201,348 B2 | 2/2019 | Scheib et al. |
| 10,211,586 B2 | 2/2019 | Adams et al. |
| 10,213,198 B2 | 2/2019 | Aronhalt et al. |
| 10,231,776 B2 | 3/2019 | Artale et al. |
| 10,238,385 B2 | 3/2019 | Yates et al. |

(56) References Cited

U.S. PATENT DOCUMENTS

| | | |
|---|---|---|
| 10,245,027 B2 | 4/2019 | Shelton, IV et al. |
| 10,265,120 B2 | 4/2019 | Yates et al. |
| D847,989 S | 5/2019 | Shelton, IV et al. |
| D850,617 S | 6/2019 | Shelton, IV et al. |
| 10,327,776 B2 | 6/2019 | Harris et al. |
| 10,335,147 B2 | 7/2019 | Rector et al. |
| 10,357,305 B2 | 7/2019 | Esch et al. |
| 10,413,291 B2 | 9/2019 | Worthington et al. |
| D865,175 S | 10/2019 | Widenhouse et al. |
| 10,470,768 B2 | 11/2019 | Harris et al. |
| 10,485,567 B2 | 11/2019 | Piskun |
| 10,548,504 B2 | 2/2020 | Shelton, IV et al. |
| 10,548,655 B2 | 2/2020 | Scheib et al. |
| 10,595,930 B2 | 3/2020 | Scheib et al. |
| 10,603,117 B2 | 3/2020 | Schings et al. |
| 10,617,412 B2 | 4/2020 | Shelton, IV et al. |
| 10,639,037 B2 | 5/2020 | Shelton, IV et al. |
| 10,687,809 B2 | 6/2020 | Shelton, IV et al. |
| 10,716,614 B2 | 7/2020 | Yates et al. |
| D893,717 S | 8/2020 | Messerly et al. |
| 2004/0122423 A1 | 6/2004 | Dycus et al. |
| 2006/0064086 A1* | 3/2006 | Odom ............. A61B 18/1442 606/51 |
| 2009/0206133 A1 | 8/2009 | Morgan et al. |
| 2010/0193566 A1 | 8/2010 | Scheib et al. |
| 2011/0028964 A1 | 2/2011 | Edwards |
| 2011/0106076 A1 | 5/2011 | Hernandez Zendejas |
| 2011/0125176 A1 | 5/2011 | Yates et al. |
| 2012/0016362 A1* | 1/2012 | Heinrich ............ A61B 17/0469 606/41 |
| 2012/0016413 A1 | 1/2012 | Timm et al. |
| 2012/0245576 A1 | 9/2012 | Epstein et al. |
| 2014/0263541 A1 | 9/2014 | Leimbach et al. |
| 2014/0263552 A1 | 9/2014 | Hall et al. |
| 2015/0060519 A1 | 3/2015 | Shelton, IV et al. |
| 2015/0088122 A1* | 3/2015 | Jensen ............... A61B 18/1445 606/37 |
| 2016/0051314 A1* | 2/2016 | Batchelor .......... A61B 17/2812 606/45 |
| 2016/0120545 A1 | 5/2016 | Shelton, IV et al. |
| 2016/0270842 A1 | 9/2016 | Strobl et al. |
| 2017/0119388 A1 | 5/2017 | Kostrzewski |
| 2017/0143336 A1 | 5/2017 | Shah et al. |
| 2017/0296213 A1 | 10/2017 | Swensgard et al. |
| 2017/0312019 A1 | 11/2017 | Trees et al. |
| 2018/0168650 A1 | 6/2018 | Shelton, IV et al. |
| 2018/0360452 A1 | 12/2018 | Shelton, IV et al. |
| 2019/0000463 A1 | 1/2019 | Shelton, IV et al. |
| 2019/0000468 A1 | 1/2019 | Adams et al. |
| 2019/0000470 A1 | 1/2019 | Yates et al. |
| 2019/0000472 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000530 A1 | 1/2019 | Yates et al. |
| 2019/0000531 A1 | 1/2019 | Messerly et al. |
| 2019/0000532 A1 | 1/2019 | Shelton, IV et al. |
| 2019/0000533 A1 | 1/2019 | Messerly et al. |
| 2019/0000535 A1 | 1/2019 | Messerly et al. |
| 2019/0000537 A1 | 1/2019 | Widenhouse et al. |
| 2019/0000538 A1 | 1/2019 | Widenhouse et al. |
| 2019/0000539 A1 | 1/2019 | Messerly et al. |

* cited by examiner

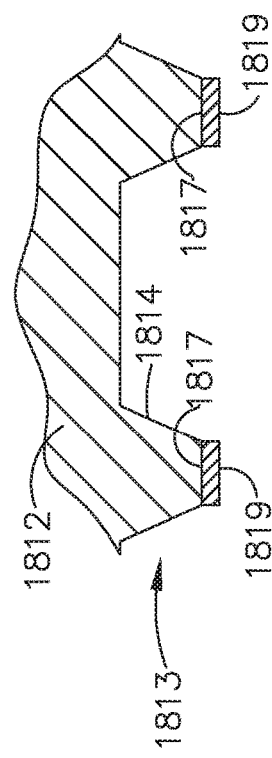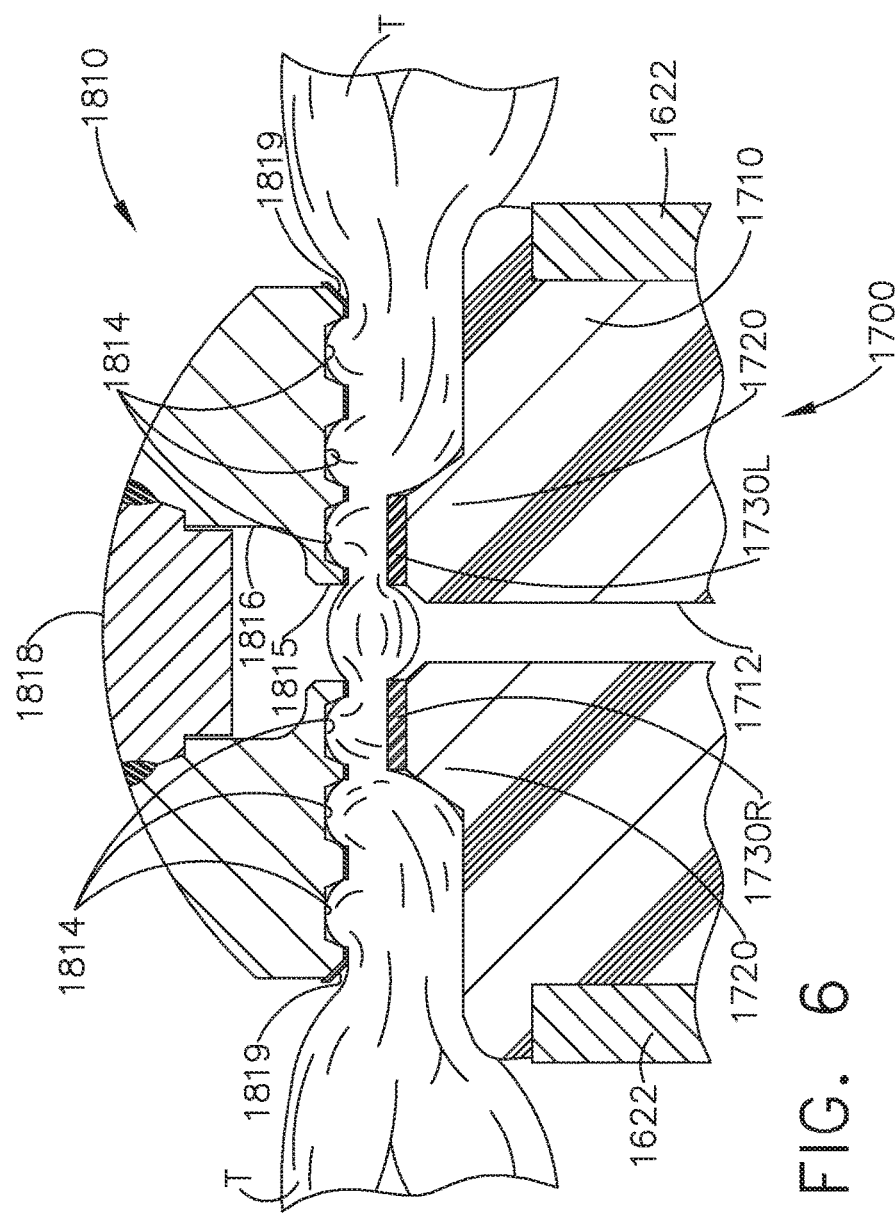
FIG. 7
FIG. 6

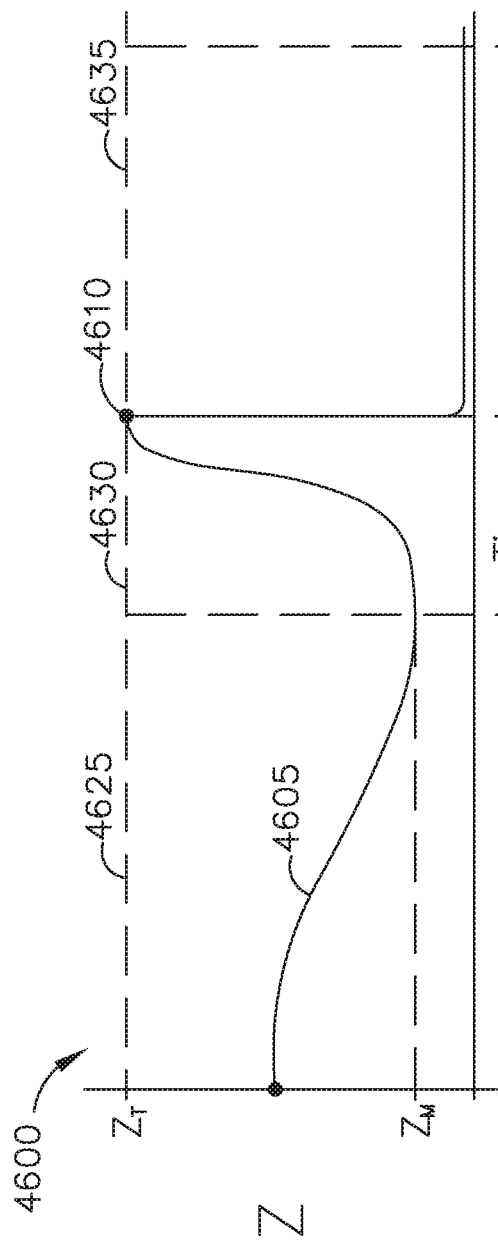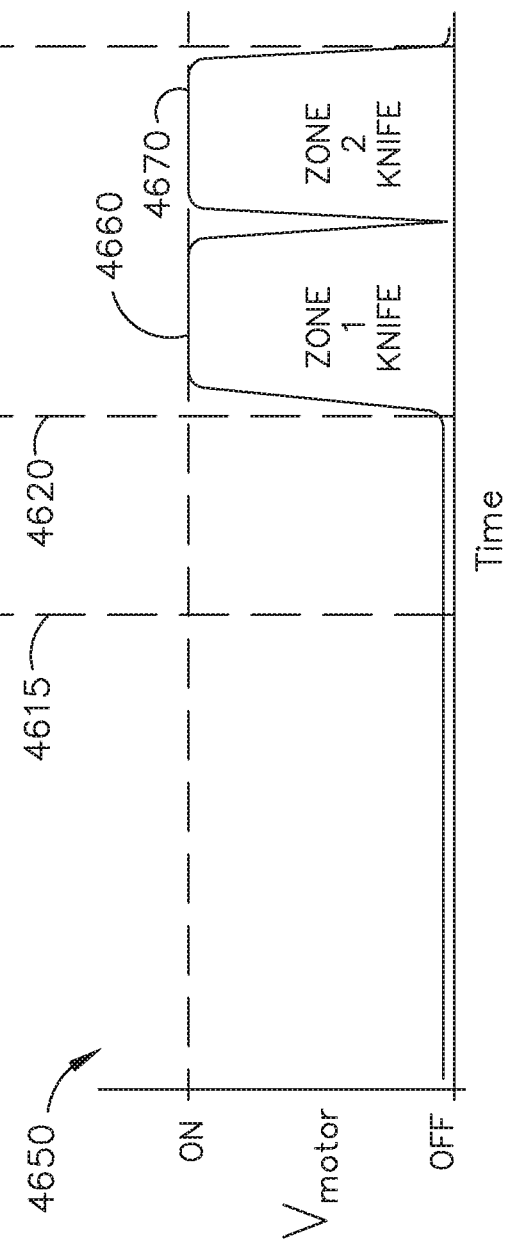

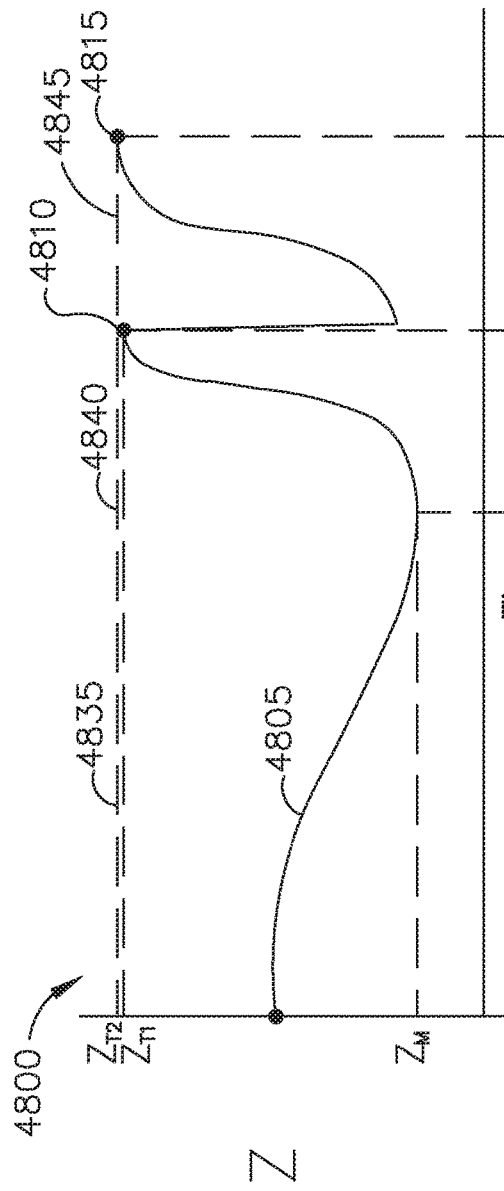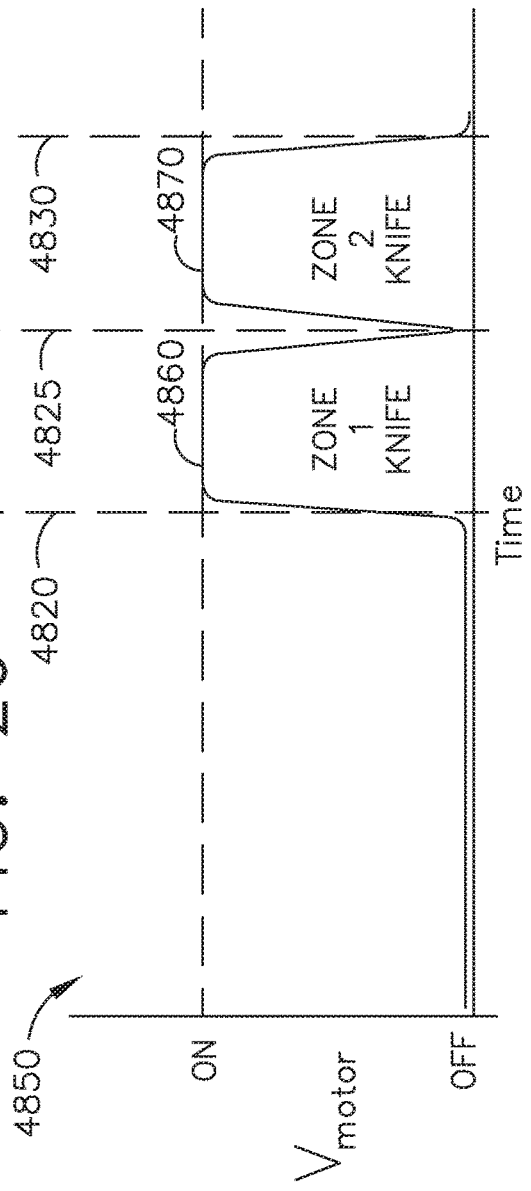

SYSTEMS AND METHODS FOR CONTROLLING CONTROL CIRCUITS FOR INDEPENDENT ENERGY DELIVERY OVER SEGMENTED SECTIONS

TECHNICAL FIELD

The present disclosure relates to surgical instruments and, in various circumstances, to surgical stapling and cutting instruments and staple cartridges therefor that are designed to staple and cut tissue.

BACKGROUND

In various open, endoscopic, and/or laparoscopic surgeries, for example, it may be desirable to coagulate, seal, and/or fuse tissue. One method of sealing tissue relies upon the application of energy, such as electrical energy, for example, to tissue captured or clamped within an end-effector or an end-effector assembly of a surgical instrument in order to cause thermal effects within the tissue. Various mono-polar and bi-polar radio frequency (RF) surgical instruments and surgical techniques have been developed for such purposes. In general, the delivery of RF energy to the captured tissue can elevate the temperature of the tissue and, as a result, the energy can at least partially denature proteins within the tissue. Such proteins, such as collagen, for example, can be denatured into a proteinaceous amalgam that intermixes and fuses, or seals, together as the proteins renature. As the treated region heals over time, this biological seal may be reabsorbed by the body's wound healing process.

In certain arrangements of a bi-polar radiofrequency (RF) surgical instrument, the surgical instrument can comprise opposing first and second jaws, wherein each jaw can comprise an electrode. In use, the tissue can be captured between the jaws such that energy can flow between the electrodes in the opposing jaws and through the tissue positioned therebetween. Such instruments may have to seal many types of tissues, such as anatomic structures having walls with irregular or thick fibrous content, bundles of disparate anatomic structures, and/or substantially thick or thin anatomic structures.

SUMMARY

In one aspect, a surgical instrument includes an end effector having a first jaw with a distal portion and a proximate portion, a second jaw that is movable relative to the first jaw, and at least one electrode in the first jaw. The surgical instrument also includes a control circuit configured to provide electrosurgical energy to the at least one electrode and a electrical conductor electrically connected between the end effector and the control circuit. The control circuit includes a shaft control segment and an electrosurgical energy control segment. The shaft control segment is configured to provide a control signal for operating the end effector to the end effector through the electrical conductor. The electrosurgical energy control segment is configured to provide the electrosurgical energy to the at least one electrode through the electrical conductor.

In an aspect, a surgical system includes a radio frequency (RF) energy generator, a handle body, an end effector, a control circuit, and a electrical conductor electrically connected between the end effector and the control circuit. The end effector includes a first jaw having a distal portion and a proximate portion, a second jaw that is movable relative to the first jaw, and at least one electrode in the first jaw. The control circuit is configured to provide RF energy, from the RF energy generator, to the at least one electrode. The control circuit includes a shaft control segment and an RF control segment. The shaft control segment is configured to provide a control signal for operating the end effector to the end effector through the electrical conductor. The RF control segment is configured to provide the RF energy to the at least one electrode through the electrical conductor.

FIGURES

The novel features of the aspects described herein are set forth with particularity in the appended claims. These aspects, however, both as to organization and methods of operation may be better understood by reference to the following description, taken in conjunction with the accompanying drawings.

FIG. 6 is a partial cross-sectional view of the end effector depicted in FIGS. 1-5 supporting an RF cartridge therein and with tissue clamped between the cartridge and the anvil according to one aspect of this disclosure.

FIG. 7 is a partial cross-sectional view of the anvil of FIG. 6 according to one aspect of this disclosure.

FIG. 23 is a graph of a tissue impedance curve as a function of time according to one aspect of this disclosure.

FIG. 24 is a graph depicting an example motor voltage curve according to one aspect of this disclosure.

FIG. 26 is a graph of a tissue impedance curve as a function of time according to one aspect of this disclosure.

FIG. 27 is a graph depicting an example motor voltage curve according to one aspect of this disclosure.

DESCRIPTION

Figure 1:
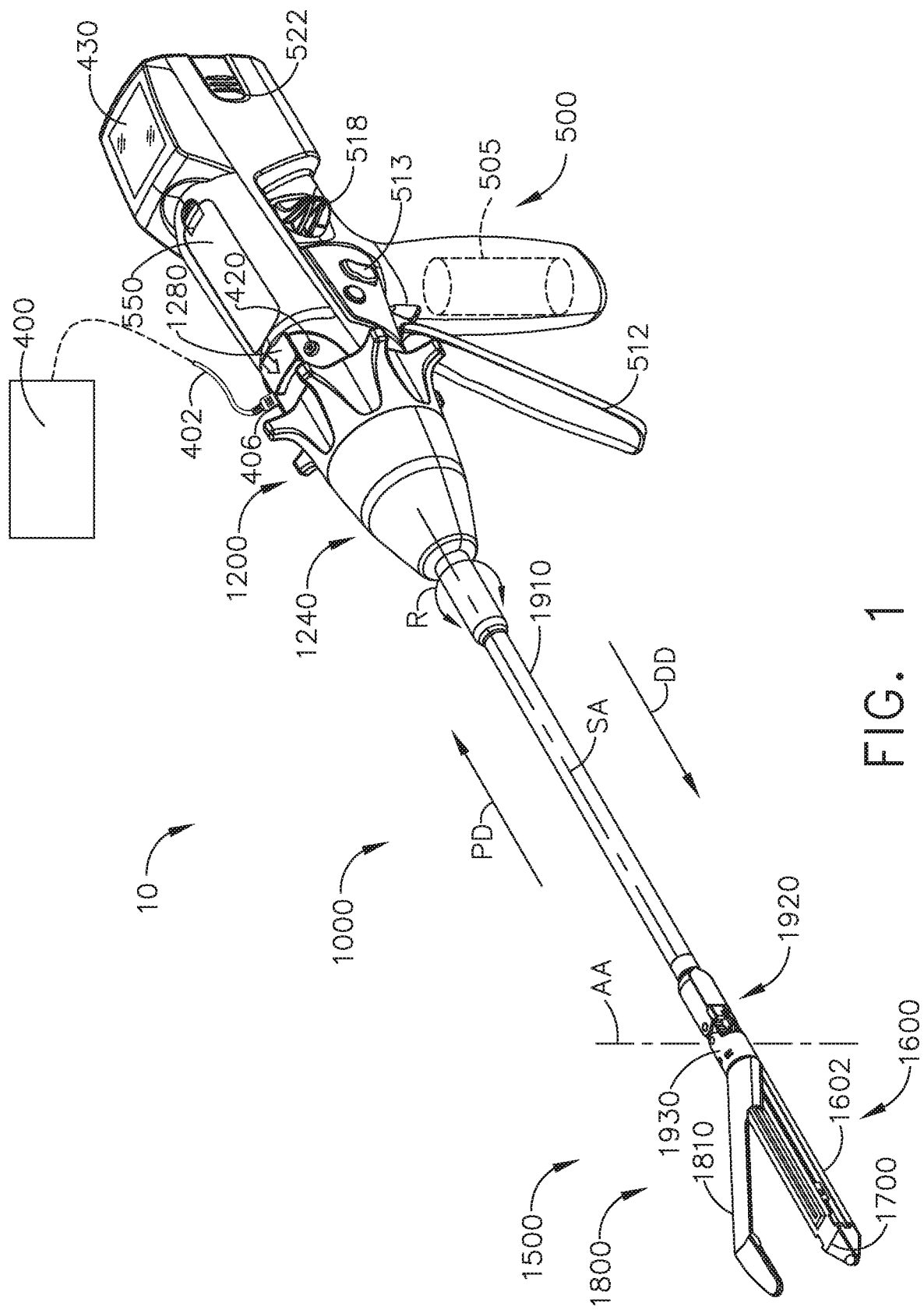
FIG. 1 is a perspective view of a surgical system including a handle assembly coupled to an interchangeable surgical tool assembly that is configured to be used in connection with conventional surgical staple/fastener cartridges and radio frequency (RF) cartridges according to one aspect of this disclosure.

Applicant of the present application owns the following patent applications filed on Jun. 28, 2017 and which are each herein incorporated by reference in their respective entireties:

U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, by inventors Jeffrey D. Messerly et al., filed Jun. 28, 2017, now U.S. Patent Application Publication No. 2019/0000478.

U.S. patent application Ser. No. 15/636,096, titled SYSTEMS AND METHODS OF DISPLAYING SURGICAL INSTRUMENT STATUS, by inventors Jeffrey D. Messerly et al., filed Jun. 28, 2017, now U.S. Patent Application Publication No. 2019/0000478.

U.S. patent application Ser. No. 15/636,110, titled SHAFT MODULE CIRCUITRY ARRANGEMENTS, by inventors Jeffrey D. Messerly et al., filed Jun. 28, 2017, now U.S. Patent Application Publication No. 2019/0000525.

U.S. patent application Ser. No. 15/636,123, titled FLEXIBLE CIRCUIT ARRANGEMENT FOR SURGICAL FASTENING INSTRUMENTS, by inventors Jeffrey D. Messerly et al., filed Jun. 28, 2017, now U.S. Patent Application Publication No. 2019/0000531.

U.S. patent application Ser. No. 15/636,134, titled SURGICAL SYSTEM COUPLEABLE WITH STAPLE CARTRIDGE AND RADIO FREQUENCY CARTRIDGE, AND HAVING A PLURALITY OF RADIO-FREQUENCY ENERGY RETURN PATHS, by inventors Jeffrey D. Messerly et al., filed Jun. 28, 2017, now U.S. Patent Application Publication No. 2019/0000535.

U.S. patent application Ser. No. 15/636,120, titled SYSTEMS AND METHODS FOR CONTROLLING CONTROL CIRCUITS FOR AN INDEPENDENT ENERGY DELIVERY OVER SEGMENTED SECTIONS, by inventors David C. Yates et al., filed Jun. 28, 2017, now U.S. Pat. No. 10,265,120.

U.S. patent application Ser. No. 15/636,150, titled SURGICAL END EFFECTOR FOR APPLYING ELECTROSURGICAL ENERGY TO DIFFERENT ELECTRODES ON DIFFERENT TIME PERIODS, by inventors Tamara Wdenhouse et al., filed Jun. 28, 2017, now U.S. Patent Application Publication No. 2019/0000537.

U.S. patent application Ser. No. 15/636,162, titled ELECTROSURGICAL CARTRIDGE FOR USE IN THIN PROFILE SURGICAL CUTTING AND STAPLING INSTRUMENT, by inventors Tamara Widenhouse et al., filed Jun. 28, 2017, now U.S. Patent Application Publication No. 2019/0000538.

U.S. patent application Ser. No. 15/636,169, titled SURGICAL END EFFECTOR TO ADJUST JAW COMPRESSION, by inventors Frederick E. Shelton, IV et al., filed Jun. 28, 2017, now U.S. Patent Application No. 2019/0000532.

U.S. patent application Ser. No. 15/636,177, titled CARTRIDGE ARRANGEMENTS FOR SURGICAL CUTTING AND FASTENING INSTRUMENTS WITH LOCKOUT DISABLEMENT FEATURES, by inventors Jason L. Harris et al., filed Jun. 28, 2017, now U.S. Patent Application Serial No. 2019/0000479.

U.S. patent application Ser. No. 15/636,1180, titled SURGICAL CUTTING AND FASTENING INSTRUMENTS WITH DUAL POWER SOURCES, by inventors Jeffrey D. Messerly et al., filed Jun. 28, 2017, now U.S. Patent Application Publication No. 2019/0000539.

Electrosurgical devices may be used in many surgical operations. Electrosurgical devices may apply electrical energy to tissue in order to treat tissue. An electrosurgical device may comprise an instrument having a distally mounted end effector comprising one or more electrodes. The end effector can be positioned against tissue such that electrical current may be introduced into the tissue. Electrosurgical devices can be configured for monopolar or bipolar operation. During monopolar operation, current may be introduced into the tissue by an active (or source) electrode on the end effector and returned through a return electrode. The return electrode may be a grounding pad and separately located on a patient's body. During bipolar operation, current may be introduced into and returned from the tissue by the active and return electrodes, respectively, of the end effector.

The end effector may include two or more jaw members. At least one of the jaw members may have at least one electrode. At least one jaw may be movable from a position spaced apart from the opposing jaw for receiving tissues to a position in which the space between the jaw members is less than that of the first position. This movement of the movable jaw may compress the tissue held between. Heat generated by the current flow through the tissue in combination with the compression achieved by the jaw's movement may form hemostatic seals within the tissue and/or between tissues and, thus, may be particularly useful for sealing blood vessels, for example. The end effector may comprise a cutting member. The cutting member may be movable relative to the tissue and the electrodes to transect the tissue.

Electrosurgical devices also may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

Electrical energy applied by electrosurgical devices can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical instrument can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

Figure 2:
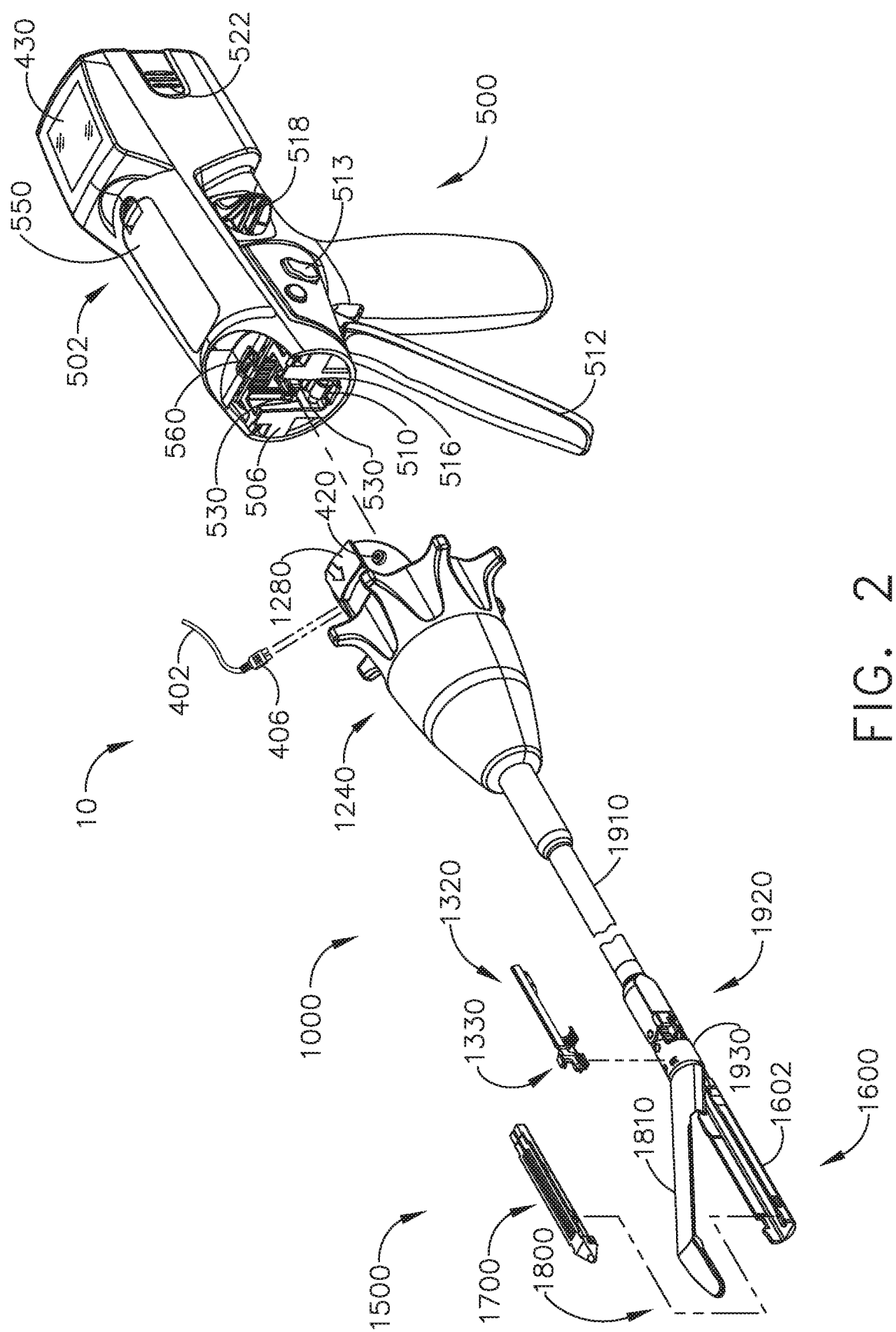
FIG. 2 is an exploded perspective assembly view of the surgical system of FIG. 1 according to one aspect of this disclosure.

FIGS. 1 and 2 depict a motor-driven surgical system 10 that may be used to perform a variety of different surgical procedures. In the illustrated arrangement, the surgical system 10 comprises an interchangeable surgical tool assembly 1000 that is operably coupled to a handle assembly 500. In another surgical system aspect, the interchangeable surgical tool assembly 1000 may also be effectively employed with a tool drive assembly of a robotically controlled or automated surgical system. For example, the surgical tool assembly 1000 disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

In the illustrated aspect, the handle assembly 500 may comprise a handle housing 502 that includes a pistol grip portion 504 that can be gripped and manipulated by the clinician. As will be briefly discussed below, the handle assembly 500 operably supports a plurality of drive systems that are configured to generate and apply various control motions to corresponding portions of the interchangeable surgical tool assembly 1000. As shown in FIG. 2, the handle assembly 500 may further include a handle frame 506 that operably supports the plurality of drive systems. For example, the handle frame 506 can operably support a "first" or closure drive system, generally designated as 510, which may be employed to apply closing and opening motions to the interchangeable surgical tool assembly 1000. In at least one form, the closure drive system 510 may include an actuator in the form of a closure trigger 512 that is pivotally supported by the handle frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, when the clinician fully depresses the closure trigger 512 to attain the full closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger to return to unactuated position. The closure release button assembly 518 may also be configured to interact with various sensors that communicate with a microcontroller in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries connected in series or parallel may be used as the power source 522 for the surgical system 10. In addition, the power source 522 may be replaceable and/or rechargeable.

The electric motor 505 is configured to axially drive a longitudinally movable drive member 540 (FIG. 3) in a distal and proximal directions depending upon the polarity of the motor. For example, when the motor 505 is driven in one rotary direction, the longitudinally movable drive member will be axially driven in a distal direction "DD". When the motor 505 is driven in the opposite rotary direction, the longitudinally movable drive member 540 will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member and/or the direction in which the drive member is being moved. Actuation of the motor 505 can be controlled by a firing trigger (not shown) that is adjacent to the closure trigger 512 and pivotally supported on the handle assembly 500. The firing trigger may be pivoted between an unactuated position and an actuated position. The firing trigger may be biased into the unactuated position by a spring or other biasing arrangement such that when the clinician releases the firing trigger, it may be pivoted or otherwise returned to the unactuated position by the spring or biasing arrangement. In at least one form, the firing trigger can be positioned "outboard" of the closure trigger 512. As discussed in U.S. Patent Application Publication No. 2015/0272575, the handle assembly 500 may be equipped with a firing trigger safety button (not shown) to prevent inadvertent actuation of the firing trigger. When the closure trigger 512 is in the unactuated position, the safety button is contained in the handle assembly 500 where the clinician cannot readily access it and move it between a safety position preventing actuation of the firing trigger and a firing position wherein the firing trigger may be fired. As the clinician depresses the closure trigger, the safety button and the firing trigger pivot down wherein they can then be manipulated by the clinician.

In at least one form, the longitudinally movable drive member 540 may have a rack of teeth 542 formed thereon for meshing engagement with a corresponding drive gear arrangement (not shown) that interfaces with the motor. See FIG. 3. Further details regarding those features may be found in U.S. Patent Application Publication No. 2015/0272575. In at least one arrangement, however, the longitudinally movable drive member is insulated to protect it from inadvertent RF energy. At least one form also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member 540 by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

In the illustrated aspect, the interchangeable surgical tool assembly 1000 includes a surgical end effector 1500 that comprises a first jaw 1600 and a second jaw 1800. In one arrangement, the first jaw comprises an elongate channel 1602 that is configured to operably support a conventional (mechanical) surgical staple/fastener cartridge 1400 (FIG. 4) or a radio frequency (RF) cartridge 1700 (FIGS. 1 and 2) therein. The second jaw 1800 comprises an anvil 1810 that is pivotally supported relative to the elongate channel 1602. The anvil 1810 may be is selectively moved toward and away from a surgical cartridge supported in the elongate channel 1602 between open and closed positions by actuating the closure drive system 510. In the illustrated arrangement, the anvil 1810 is pivotally supported on a proximal end portion of the elongate channel 1602 for selective pivotal travel about a pivot axis that is transverse to the shaft axis SA. Actuation of the closure drive system 510 may result in the distal axial movement of a proximal closure member or proximal closure tube 1910 that is attached to an articulation connector 1920.

Figure 3:
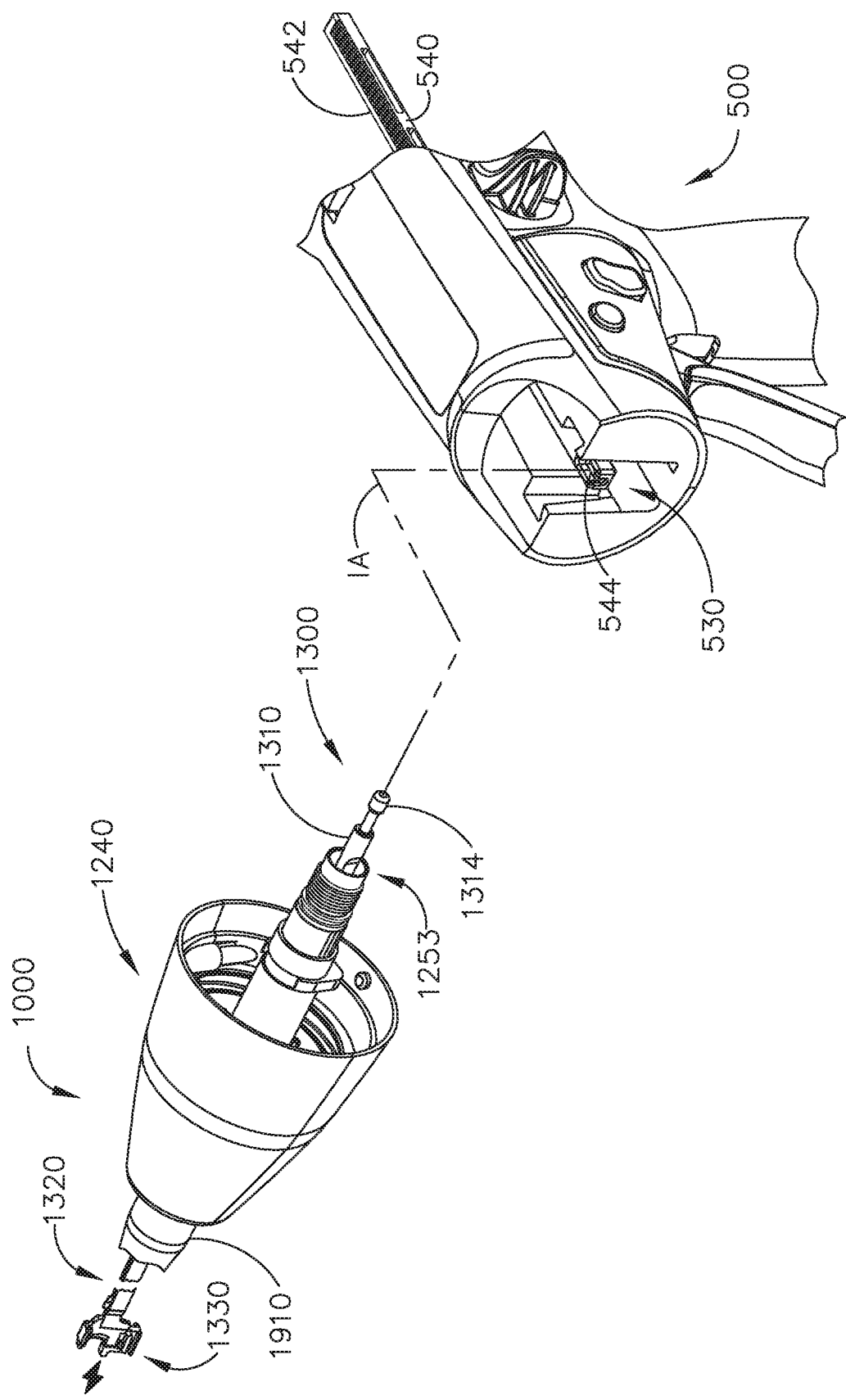
FIG. 3 is another exploded perspective assembly view of portions of the handle assembly and interchangeable surgical tool assembly of FIGS. 1 and 2 according to one aspect of this disclosure.
Figure 4:
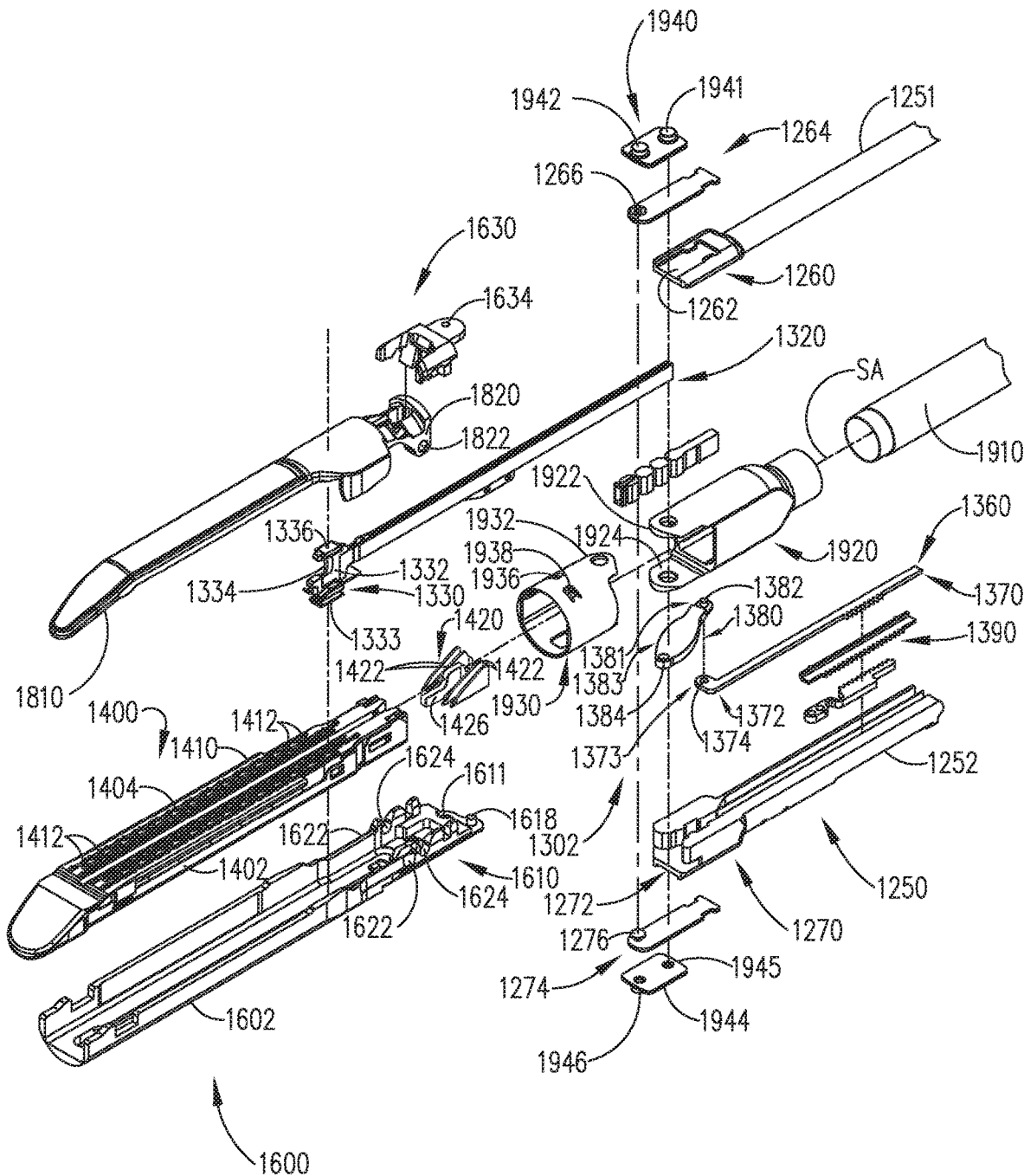
FIG. 4 is an exploded assembly view of a proximal portion of the interchangeable surgical tool assembly of FIGS. 1-3 according to one aspect of this disclosure.

Turning to FIG. 4, the articulation connector 1920 includes upper and lower tangs 1922, 1924 protrude distally from a distal end of the articulation connector 1920 to be movably coupled to an end effector closure sleeve or distal closure tube segment 1930. See FIG. 3. The distal closure tube segment 1930 includes an upper tang 1932 and a lower tang (not shown) that protrude proximally from a proximal end thereof. An upper double pivot link 1940 includes proximal and distal pins 1941, 1942 that engage corresponding holes in the upper tangs 1922, 1932 of the articulation connector 1920 and distal closure tube segment 1930, respectively. Similarly, a lower double pivot link 1944 includes proximal and distal pins 1945, 1946 that engage corresponding holes in the lower tangs 1924 of the articulation connector 1920 and distal closure tube segment 1930, respectively.

Still referring to FIG. 4, in the illustrated example, the distal closure tube segment 1930 includes positive jaw opening features or tabs 1936, 1938 that correspond with corresponding portions of the anvil 1810 to apply opening motions to the anvil 1810 as the distal closure tube segment 1930 is retracted in the proximal direction PD to a starting position. Further details regarding the opening and closing of the anvil 1810 may be found in U.S. patent application Ser. No. 15/635,621 entitled SURGICAL INSTRUMENT WITH POSITIVE JAW OPENING FEATURES, filed on Jun. 28, 2017, now U.S. Patent Application Publication No. 2019/0000463, the entire disclosure of which is hereby incorporated by reference herein.

Figure 5:
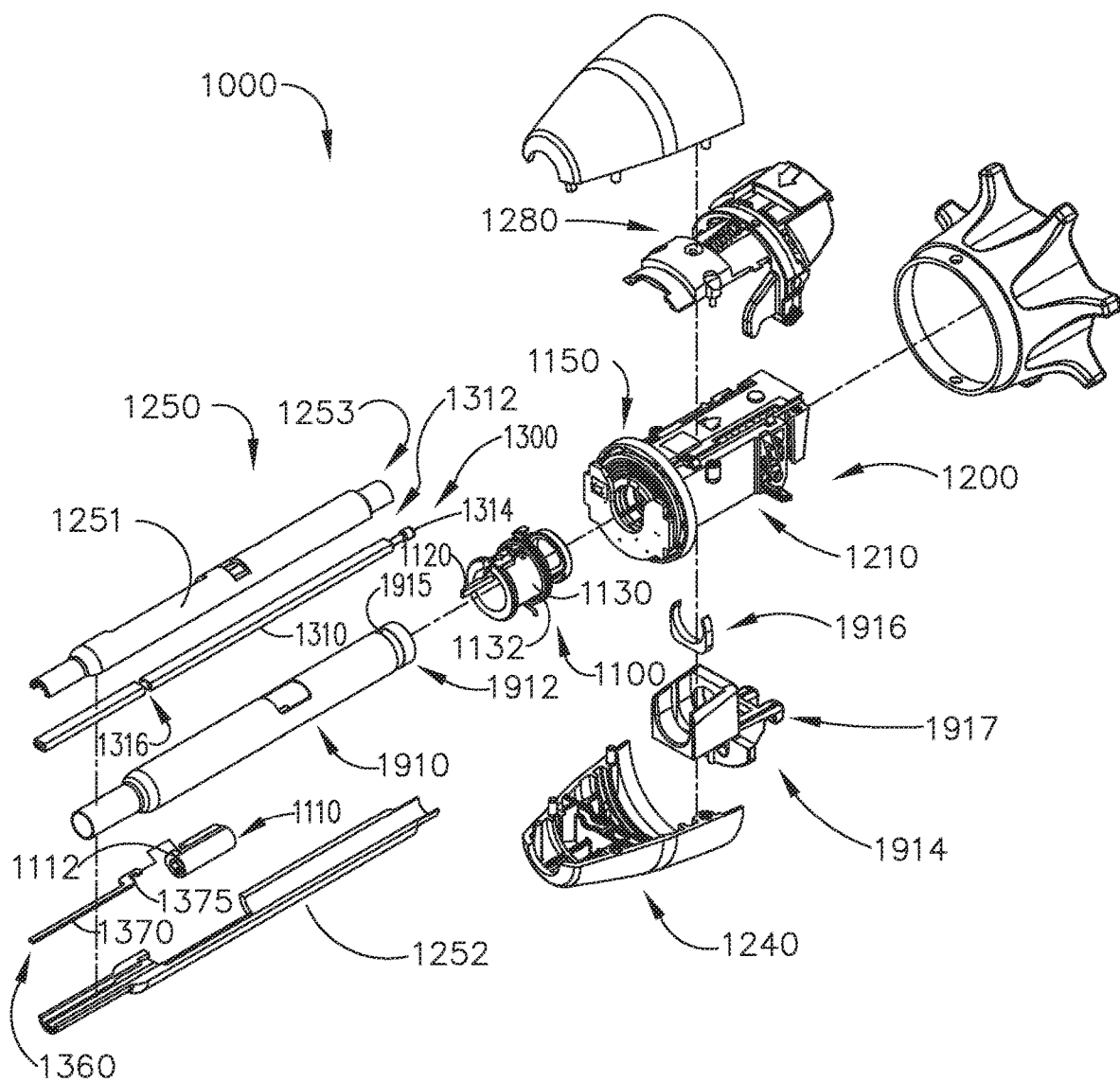
FIG. 5 is another exploded assembly view of a distal portion of the interchangeable surgical tool assembly of FIGS. 1-4 according to one aspect of this disclosure.

As shown in FIG. 5, in at least one arrangement, the interchangeable surgical tool assembly 1000 includes a tool frame assembly 1200 that comprises a tool chassis 1210 that operably supports a nozzle assembly 1240 thereon. As further discussed in detail in U.S. patent application Ser. No. 15/635,631 entitled SURGICAL INSTRUMENT WITH AXIALLY MOVABLE CLOSURE MEMBER, filed on Jun. 28, 2017, now U.S. Patent Application Publication No. 2019/0000464, and which is hereby incorporated by reference in its entirety herein, the tool chassis 1210 and nozzle arrangement 1240 facilitate rotation of the surgical end effector 1500 about a shaft axis SA relative to the tool chassis 1210. Such rotational travel is represented by arrow R in FIG. 1. As also shown in FIGS. 4 and 5, the interchangeable surgical tool assembly 1000 includes a spine assembly 1250 that operably supports the proximal closure tube 1910 and is coupled to the surgical end effector 1500. In various circumstances, for ease of assembly, the spine assembly 1250 may be fabricated from an upper spine segment 1251 and a lower spine segment 1252 that are interconnected together by snap features, adhesive, welding, etc. In assembled form, the spine assembly 1250 includes a proximal end 1253 that is rotatably supported in the tool chassis 1210. In one arrangement, for example, the proximal end 1253 of the spine assembly 1250 is attached to a spine bearing (not shown) that is configured to be supported within the tool chassis 1210. Such arrangement facilitates rotatable attachment of the spine assembly 1250 to the tool chassis such that the spine assembly 1250 may be selectively rotated about a shaft axis SA relative to the tool chassis 1210.

As shown in FIG. 4, the upper spine segment 1251 terminates in an upper lug mount feature 1260 and the lower spine segment 1252 terminates in a lower lug mount feature 1270. The upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis SA. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes lower pivot pin 1276 that adapted to be received within a pivot hole 1611 formed in the proximal end portion 1610 of the elongate channel 1602. The lower pivot pin 1276 as well as the pivot hole 1611 is offset from the shaft axis SA. The lower pivot pin 1276 is vertically aligned with the pivot socket 1266 to define the articulation axis AA about which the surgical end effector 1500 may articulate relative to the shaft axis SA. See FIG. 1. Although the articulation axis AA is transverse to the shaft axis SA, in at least one arrangement, the articulation axis AA is laterally offset therefrom and does not intersect the shaft axis SA.

Turning to FIG. 5, a proximal end 1912 of the proximal closure tube 1910 is rotatably coupled to a closure shuttle 1914 by a connector 1916 that is seated in an annular groove 1915 in the proximal closure tube segment 1910. The closure shuttle 1914 is supported for axial travel within the tool chassis 1210 and has a pair of hooks 1917 thereon configured to engage the closure drive system 510 when the tool chassis 1210 is coupled to the handle frame 506. The tool chassis 1210 further supports a latch assembly 1280 for releasably latching the tool chassis 1210 to the handle frame 506. Further details regarding the tool chassis 1210 and latch assembly 1280 may be found in U.S. patent application Ser. No. 15/635,631, entitled SURGICAL INSTRUMENT WITH AXIALLY MOVABLE CLOSURE MEMBER, filed on Jun. 28, 2017, now U.S. Patent Application Publication No. 2019/0000464 and which is the entire disclosure of which is hereby incorporated by reference herein.

The firing drive system 530 in the handle assembly 500 is configured to be operably coupled to a firing system 1300 that is operably supported in the interchangeable surgical tool assembly 1000. The firing system 1300 may include an intermediate firing shaft portion 1310 that is configured to be axially moved in the distal and proximal directions in response to corresponding firing motions applied thereto by the firing drive system 530. See FIG. 4. As shown in FIG. 5, a proximal end 1312 of the intermediate firing shaft portion 1310 has a firing shaft attachment lug 1314 formed thereon that is configured to be seated into an attachment cradle 544 (FIG. 3) that is on the distal end of the longitudinally movable drive member 540 of the firing drive system 530 within the handle assembly 500. Such arrangement facilitates the axial movement of the intermediate firing shaft portion 1310 upon actuation of the firing drive system 530. In the illustrated example, the intermediate firing shaft portion 1310 is configured for attachment to a distal cutting portion or knife bar 1320. As shown in FIG. 4, the knife bar 1320 is connected to a firing member or knife member 1330. The knife member 1330 comprises a knife body 1332 that operably supports a tissue cutting blade 1334 thereon. The knife body 1332 may further include anvil engagement tabs or features 1336 and channel engagement features or a foot 1338. The anvil engagement features 1336 may serve to apply additional closure motions to the anvil 1810 as the knife member 1330 is advanced distally through the end effector 1500.

In the illustrated example, the surgical end effector 1500 is selectively articulatable about the articulation axis AA by an articulation system 1360. In one form, the articulation system 1360 includes proximal articulation driver 1370 that is pivotally coupled to an articulation link 1380. As can be most particularly seen in FIG. 4, an offset attachment lug 1373 is formed on a distal end 1372 of the proximal articulation driver 1370. A pivot hole 1374 is formed in the offset attachment lug 1373 and is configured to pivotally receive therein a proximal link pin 1382 formed on the proximal end 1381 of the articulation link 1380. A distal end 1383 of the articulation link 1380 includes a pivot hole 1384 that is configured to pivotally receive therein a channel pin 1618 formed on the proximal end portion 1610 of the elongate channel 1602. Thus, axial movement of proximal articulation driver 1370 will thereby apply articulation motions to the elongate channel 1602 to thereby cause the surgical end effector 1500 to articulate about the articulation axis AA relative to the spine assembly 1250. In various circumstances, the proximal articulation driver 1370 can be held in position by an articulation lock 1390 when the proximal articulation driver 1370 is not being moved in the proximal or distal directions. Further details regarding an example form of articulation lock 1390 may be found in U.S. patent application Ser. No. 15/635,837, entitled SURGICAL INSTRUMENT COMPRISING AN ARTICULATION SYSTEM LOCKABLE TO A FRAME, filed on Jun. 28, 2017, now U.S. Patent Application Publication No. 2019/0000472, the entire disclosure of which is hereby incorporated by reference herein.

Further to the above, the interchangeable surgical tool assembly 1000 can include a shifter assembly 1100 which can be configured to selectively and releasably couple the proximal articulation driver 1310 to the firing system 1300. As illustrated in FIG. 5, for example, in one form, the shifter assembly 1100 includes a lock collar, or lock sleeve 1110, positioned around the intermediate firing shaft portion 1310 of the firing system 1300 wherein the lock sleeve 1110 can be rotated between an engaged position in which the lock sleeve 1110 operably couples the proximal articulation driver 1370 to the firing member assembly 1300 and a disengaged position in which the proximal articulation driver 1370 is not operably coupled to the firing member assembly 1300. When lock sleeve 1110 is in its engaged position, distal movement of the firing member assembly 1300 can move the proximal articulation driver 1370 distally and, correspondingly, proximal movement of the firing member assembly 1300 can move the proximal articulation driver 1370 proximally. When lock sleeve 1110 is in its disengaged position, movement of the firing member assembly 1300 is not transmitted to the proximal articulation driver 1370 and, as a result, the firing member assembly 1300 can move independently of the proximal articulation driver 1370. In various circumstances, the proximal articulation driver 1370 can be held in position by the articulation lock 1390 when the proximal articulation driver 1370 is not being moved in the proximal or distal directions by the firing member assembly 1300.

In the illustrated arrangement, the intermediate firing shaft portion 1310 of the firing member assembly 1300 is formed with two opposed flat sides with a drive notch 1316 formed therein. See FIG. 5. As can also be seen in FIG. 5, the lock sleeve 1110 comprises a cylindrical, or an at least substantially cylindrical, body that includes a longitudinal aperture that is configured to receive the intermediate firing shaft portion 1310 therethrough. The lock sleeve 1110 can comprise diametrically-opposed, inwardly-facing lock protrusions that, when the lock sleeve 1110 is in one position, are engagingly received within corresponding portions of the drive notch 1316 in the intermediate firing shaft portion 1310 and, when in another position, are not received within the drive notch 1316 to thereby permit relative axial motion between the lock sleeve 1110 and the intermediate firing shaft 1310. As can be further seen in FIG. 5, the lock sleeve 1110 further includes a lock member 1112 that is sized to be movably received within a notch 1375 in a proximal end of the proximal articulation driver 1370. Such arrangement permits the lock sleeve 1110 to slightly rotate into and out of engagement with the intermediate firing shaft portion 1310 while remaining in position for engagement or in engagement with the notch 1375 in the proximal articulation driver 1370. For example, when the lock sleeve 1110 is in its engaged position, the lock protrusions are positioned within the drive notch 1316 in the intermediate firing shaft portion 1310 such that a distal pushing force and/or a proximal pulling force can be transmitted from the firing member assembly 1300 to the lock sleeve 1110. Such axial pushing or pulling motion is then transmitted from the lock sleeve 1110 to the proximal articulation driver 1370 to thereby articulate the surgical end effector 1500. In effect, the firing member assembly 1300, the lock sleeve 1110, and the proximal articulation driver 1370 will move together when the lock sleeve 1110 is in its engaged (articulation) position. On the other hand, when the lock sleeve 1110 is in its disengaged position, the lock protrusions are not received within the drive notch 1316 in the intermediate firing shaft portion 1310 and, as a result, a distal pushing force and/or a proximal pulling force may not be transmitted from the firing member assembly 1300 to the lock sleeve 1110 (and the proximal articulation driver 1370).

In the illustrated example, relative movement of the lock sleeve 1110 between its engaged and disengaged positions may be controlled by the shifter assembly 1100 that interfaces with the proximal closure tube 1910. Still referring to FIG. 5, the shifter assembly 1100 further includes a shifter key 1120 that is configured to be slidably received within a key groove formed in the outer perimeter of the lock sleeve 1110. Such arrangement enables the shifter key 1120 to move axially with respect to the lock sleeve 1110. As discussed in further detail in U.S. patent application Ser. No. 15/635,631, entitled SURGICAL INSTRUMENT WITH AXIALLY MOVABLE CLOSURE MEMBER, filed on Jun. 28, 2017, now U.S. Patent Application Publication No. 2019/0000464, the entire disclosure of which is hereby incorporated by reference herein, a portion of the shifter key 1120 is configured to cammingly interact with a cam opening (not shown) in the proximal closure tube portion 1910. Also in the illustrated example, the shifter assembly 1100 further includes a switch drum 1130 that is rotatably received on a proximal end portion of the proximal closure tube portion 1910. A portion of the shifter key 1120 extends through an axial slot segment in the switch drum 1130 and is movably received within an arcuate slot segment in the switch drum 1130. A switch drum torsion spring 1132 is mounted on the switch drum 1130 and engages a portion of the nozzle assembly 1240 to apply a torsional bias or rotation which serves to rotate the switch drum 1130 until the portion of the shifter key 1120 reaches an end portion of the cam opening in the proximal closure tube portion 1910. When in this position, the switch drum 1130 may provide a torsional bias to the shifter key 1120 which thereby causes the lock sleeve 1110 to rotate into its engaged position with the intermediate firing shaft portion 1310. This position also corresponds to the unactuated configuration of the proximal closure tube 1910 (and distal closure tube segment 1930).

In one arrangement, for example, when the proximal closure tube 1910 is in an unactuated configuration (anvil 1810 is in an open position spaced away from the cartridge mounted in the elongate channel 1602) actuation of the intermediate firing shaft portion 1310 will result in the axial movement of the proximal articulation driver 1370 to facilitate articulation of the end effector 1500. Once the user has articulated the surgical end effector 1500 to a desired orientation, the user may then actuate the proximal closure tube portion 1910. Actuation of the proximal closure tube portion 1910 will result in the distal travel of the distal closure tube segment 1930 to ultimately apply a closing motion to the anvil 1810. This distal travel of the proximal closure tube portion 1910 will result in the cam opening therein cammingly interacting with a cam portion of the shifter key 1120 to thereby cause the shifter key 1120 to rotate the lock sleeve 1110 in an actuation direction. Such rotation of the lock sleeve 1110 will result in the disengagement of the lock protrusions from the drive notch 1316 in the intermediate firing shaft portion 1310. When in such configuration, the firing drive system 530 may be actuated to actuate the intermediate firing shaft portion 1310 without actuating the proximal articulation driver 1370. Further details concerning the operation of the switch drum 1130 and lock sleeve 1110, as well as alternative articulation and firing drive arrangements that may be employed with the various interchangeable surgical tool assemblies described herein, may be found in U.S. patent application Ser. No. 13/803,086, now U.S. Patent Application Publication No. 2014/0263541, and U.S. patent application Ser. No. 15/019,196, the entire disclosures of which are hereby incorporated by reference herein.

Figure 15:
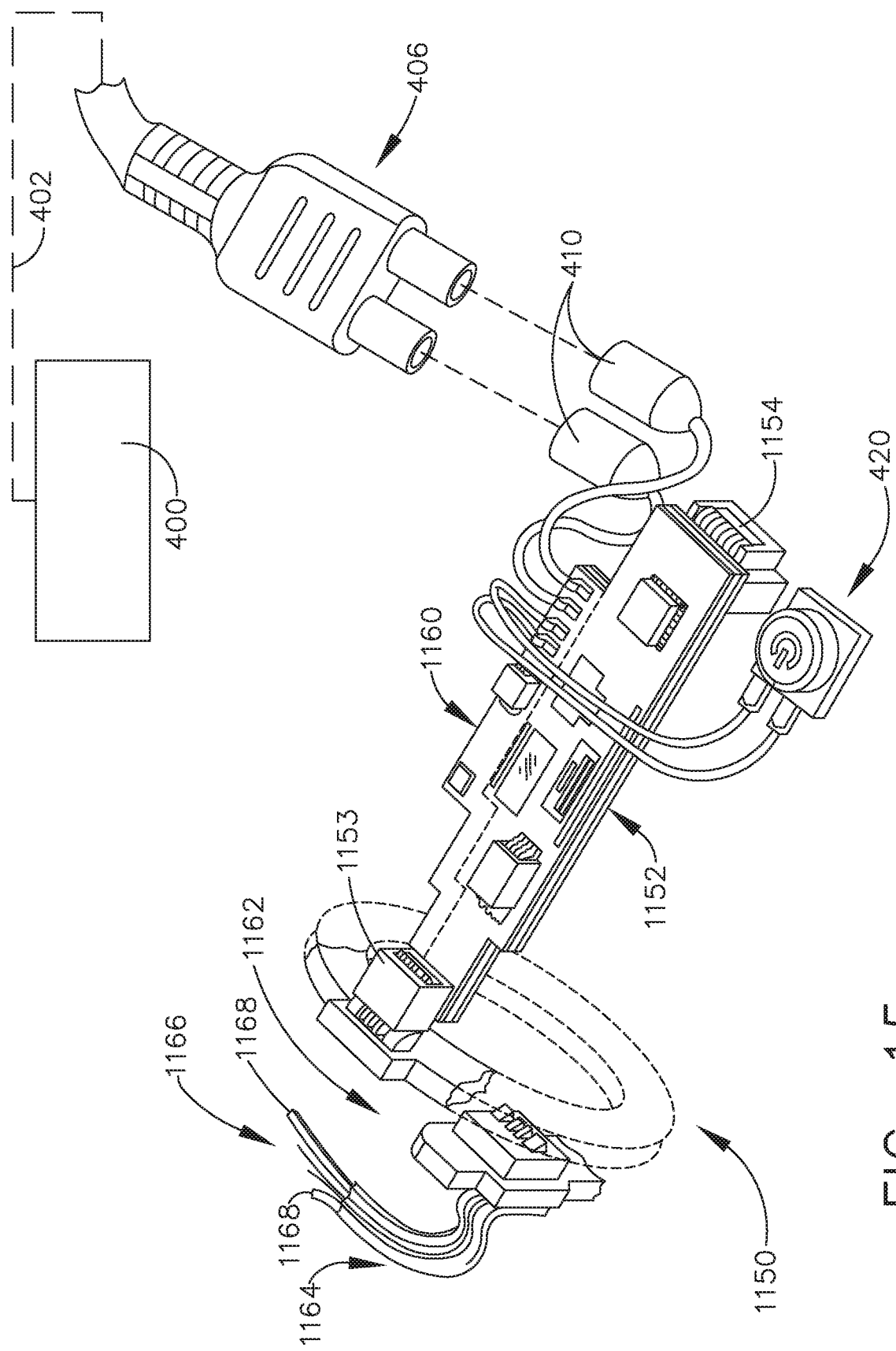
FIG. 15 is a perspective view of an onboard circuit board arrangement and RF generator plus configuration according to one aspect of this disclosure.

As also illustrated in FIGS. 5 and 15, the interchangeable surgical tool assembly 1000 can comprise a slip ring assembly 1150 which can be configured to conduct electrical power to and/or from the surgical end effector 1500 and/or communicate signals to and/or from the surgical end effector 1500, back to an onboard circuit board 1152, while facilitating rotational travel of the shaft and end effector 1500 about the shaft axis SA relative to the tool chassis 1210 by rotating the nozzle assembly 1240. As shown in FIG. 15, in at least one arrangement, the onboard circuit board 1152 includes an onboard connector 1154 that is configured to interface with a housing connector 562 (FIG. 9) communicating with a microprocessor 560 that is supported in the handle assembly 500 or robotic system controller, for example. The slip ring assembly 1150 is configured to interface with a proximal connector 1153 that interfaces with the onboard circuit board 1152. Further details concerning the slip ring assembly 1150 and associated connectors may be found in U.S. patent application Ser. No. 13/803,086, now U.S. Patent Application Publication No. 2014/0263541, and U.S. patent application Ser. No. 15/019,196 which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

An example version of the interchangeable surgical tool assembly 1000 disclosed herein may be employed in connection with a standard (mechanical) surgical fastener cartridge 1400 or a cartridge 1700 that is configured to facilitate cutting of tissue with the knife member and seal the cut tissue using radio frequency (RF) energy. Turning again to FIG. 4, a conventional or standard mechanical-type cartridge 1400 is depicted. Such cartridge arrangements are known and may comprise a cartridge body 1402 that is sized and shaped to be removably received and supported in the elongate channel 1602. For example, the cartridge body 1402 may be configured to be removably retained in snap engagement with the elongate channel 1602. The cartridge body 1402 includes an elongate slot 1404 to accommodate axial travel of the knife member 1330 therethrough. The cartridge body 1402 operably supports therein a plurality of staple drivers (not shown) that are aligned in rows on each side of the centrally disposed elongate slot 1404. The drivers are associated with corresponding staple/fastener pockets 1412 that open through the upper deck surface 1410 of the cartridge body 1402. Each of the staple drivers supports one or more surgical staple or fastener (not shown) thereon. A sled assembly 1420 is supported within a proximal end of the cartridge body 1402 and is located proximal to the drivers and fasteners in a starting position when the cartridge 1400 is new and unfired. The sled assembly 1420 includes a plurality of sloped or wedge-shaped cams 1422 wherein each cam 1422 corresponds to a particular line of fasteners or drivers located on a side of the slot 1404. The sled assembly 1420 is configured to be contacted and driven by the knife member 1330 as the knife member is driven distally through the tissue that is clamped between the anvil and the cartridge deck surface 1410. As the drivers are driven upward toward the cartridge deck surface 1410, the fastener(s) supported thereon are driven out of their staple pockets 1412 and through the tissue that is clamped between anvil and the cartridge.

Still referring to FIG. 4, the anvil 1810 in at least one form includes an anvil mounting portion 1820 that has a pair of anvil trunnions 1822 protruding laterally therefrom to be pivotally received in corresponding trunnion cradles 1614 formed in the upstanding walls 1622 of the proximal end portion 1610 of the elongate channel 1602. The anvil trunnions 1822 are pivotally retained in their corresponding trunnion cradle 1614 by the channel cap or anvil retainer 1630. The anvil mounting portion 1820 is movably or pivotably supported on the elongate channel 1602 for selective pivotal travel relative thereto about a fixed anvil pivot axis that is transverse to the shaft axis SA. As shown in FIGS. 6 and 7, in at least one form, the anvil 1810 includes an anvil body portion 1812 that is fabricated from an electrically conductive metal material for example and has a staple forming undersurface 1813 that has a series of fastener forming pockets 1814 formed therein on each side of a centrally disposed anvil slot 1815 that is configured to slidably accommodate the knife member 1330 therein. The anvil slot 1815 opens into an upper opening 1816 that extends longitudinally through the anvil body 1812 to accommodate the anvil engagement features 1336 on the knife member 1330 during firing. When a conventional mechanical surgical staple/fastener cartridge 1400 is installed in the elongate channel 1602, the staples/fasteners are driven through the tissue T and into forming contact with the corresponding fastener forming pockets 1814. The anvil body 1812 may have an opening in the upper portion thereof to facilitate ease of installation for example. An anvil cap 1818 may be inserted therein and welded to the anvil body 1812 to enclose the opening and improve the overall stiffness of the anvil body 1812. As shown in FIG. 7, to facilitate use of the end effector 1500 in connection with RF cartridges 1700, the tissue facing segments 1817 of the fastener forming undersurface 1813 may have electrically insulative material 1819 thereon.

Figure 8:
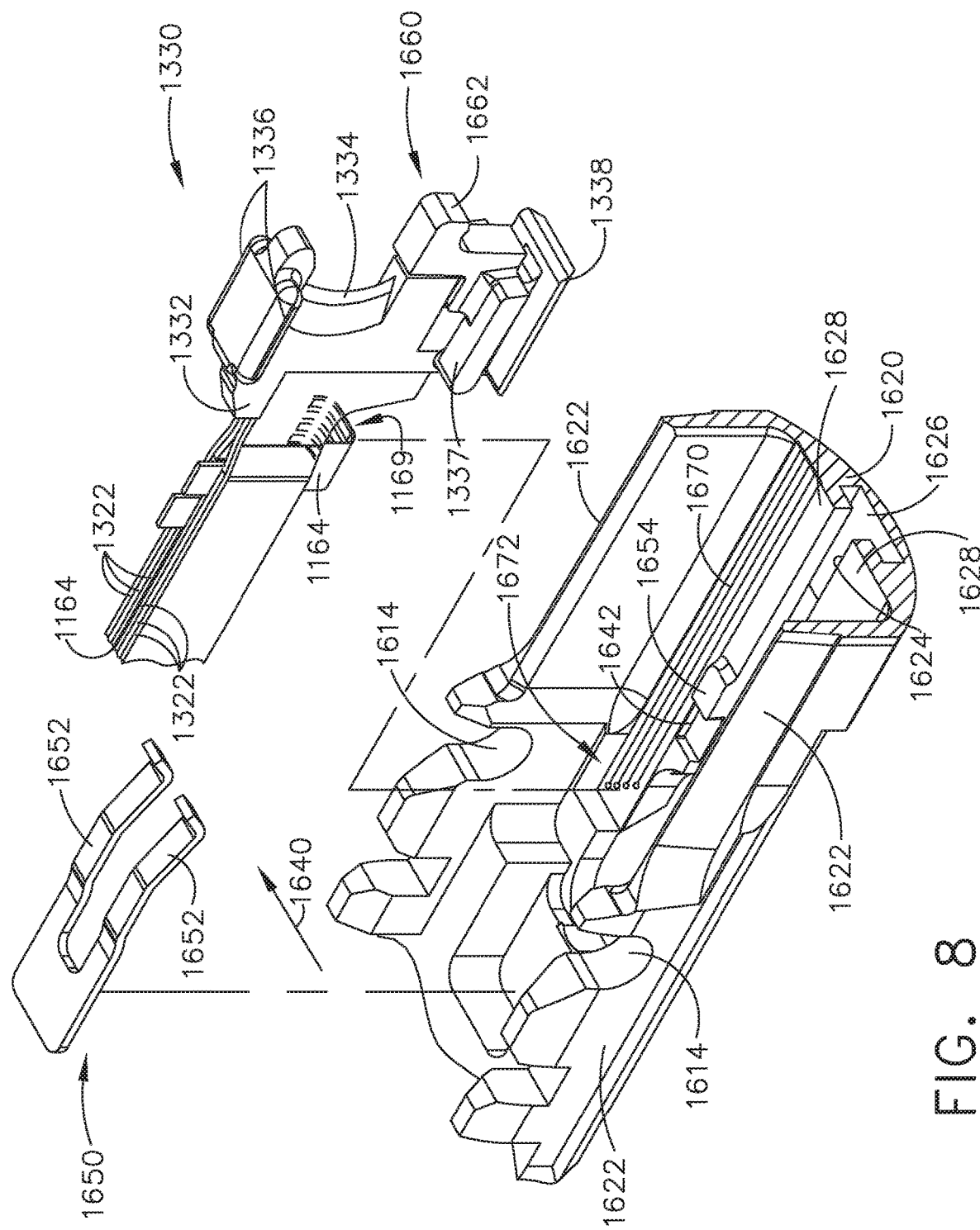
FIG. 8 is another exploded assembly view of a portion of the interchangeable surgical tool assembly of FIGS. 1-5 according to one aspect of this disclosure.

In the illustrated arrangement, the interchangeable surgical tool assembly 1000 is configured with a firing member lockout system, generally designated as 1640. See FIG. 8. As shown in FIG. 8, the elongate channel 1602 includes a bottom surface or bottom portion 1620 that has two upstanding side walls 1622 protruding therefrom. A centrally disposed longitudinal channel slot 1624 is formed through the bottom portion 1620 to facilitate the axial travel of the knife member 1330 therethrough. The channel slot 1624 opens into a longitudinal passage 1626 that accommodates the channel engagement feature or foot 1338 on the knife member 1330. The passage 1626 serves to define two inwardly extending ledge portions 1628 that serve to engage corresponding portions of the channel engagement feature or foot 1338. The firing member lockout system 1640 includes proximal openings 1642 located on each side of the channel slot 1624 that are each configured to receive corresponding portions of the channel engagement feature or foot 1338 when the knife member 1330 is in a starting position. A knife lockout spring 1650 is supported in the proximal end 1610 of the elongate channel 1602 and serves to bias the knife member 1330 downward. As shown in FIG. 8, the knife lockout spring 1650 includes two distally ending spring arms 1652 that are configured to engage corresponding central channel engagement features 1337 on the knife body 1332. The spring arms 1652 are configured to bias the central channel engagement features 1337 downward. Thus, when in the starting (unfired position), the knife member 1330 is biased downward such that the channel engagement features or foot 1338 is received within the corresponding proximal openings 1642 in the elongate 1602 channel. When in that locked position, if one were to attempt to distally advance the knife 1330, the central channel engagement features 1137 and/or foot 1338 would engage upstanding ledges 1654 on the elongate channel 1602 (FIGS. 8 and 11) and the knife 1330 could not be fired.

Still referring to FIG. 8, the firing member lockout system 1640 also includes an unlocking assembly 1660 formed or supported on a distal end of the firing member body 1332. The unlocking assembly 1660 includes a distally extending ledge 1662 that is configured to engage an unlocking feature 1426 formed on the sled assembly 1420 when the sled assembly 1420 is in its starting position in an unfired surgical staple cartridge 1400. Thus, when an unfired surgical staple cartridge 1400 is properly installed in the elongate channel 1602, the ledge 1662 on the unlocking assembly 1660 contacts the unlocking feature 1426 on the sled assembly 1420 which serves to bias the knife member 1330 upward such that the central channel engagement features 1137 and/or foot 1338 clear the upstanding ledges 1654 in the channel bottom 1620 to facilitate axial passage of the knife member 1330 through the elongate channel 1602. If a partially fired cartridge 1400 is unwittingly installed in the elongate channel, the sled assembly 1420 will not be in the starting position and the knife member 1330 will remain in the locked position.

Figure 9:
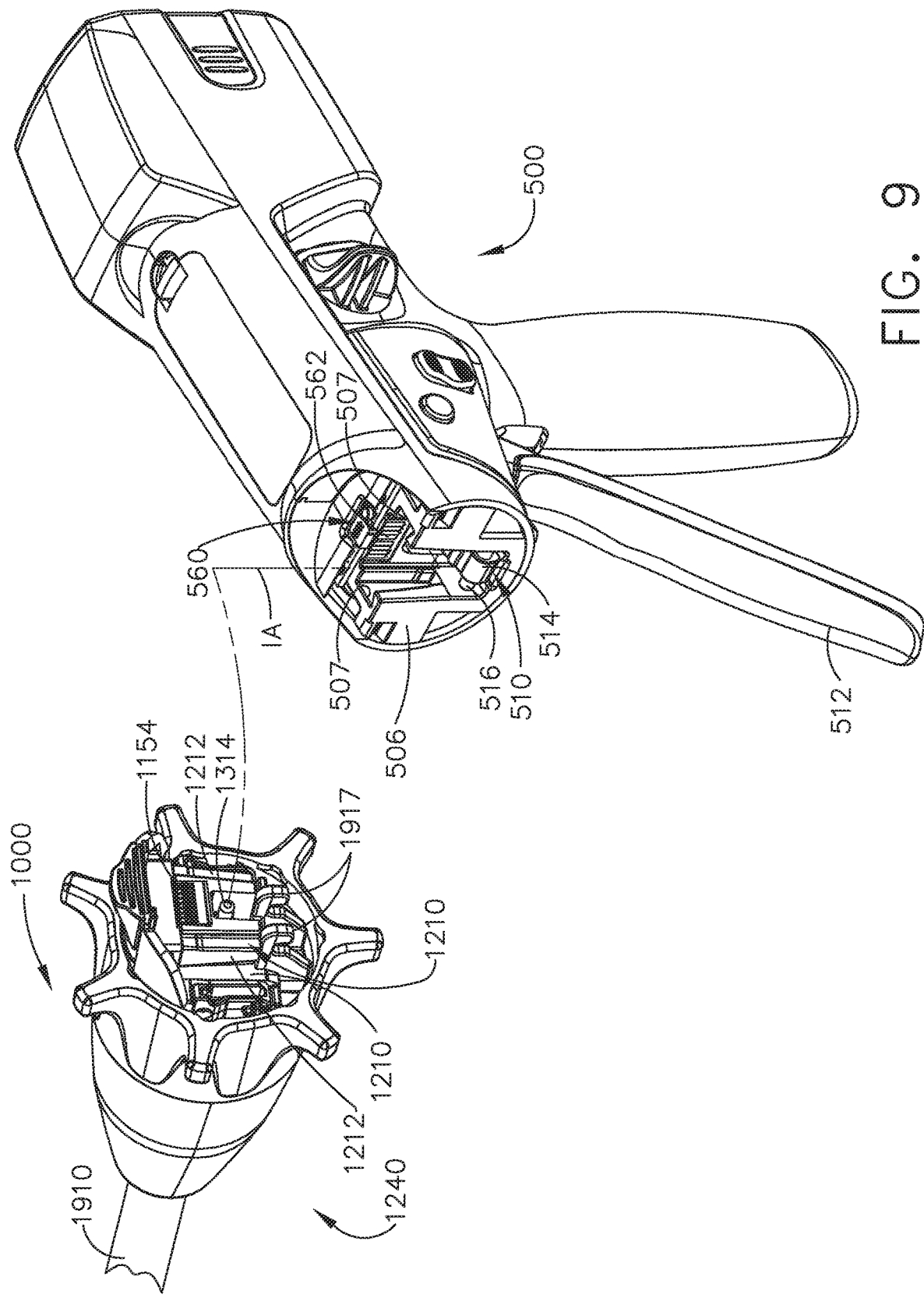
FIG. 9 is another exploded assembly view of the interchangeable surgical tool assembly and handle assembly of FIGS. 1 and 2 according to one aspect of this disclosure.

Attachment of the interchangeable surgical tool assembly 1000 to the handle assembly 500 will now be described with reference to FIGS. 3 and 9. To commence the coupling process, the clinician may position the tool chassis 1210 of the interchangeable surgical tool assembly 1000 above or adjacent to the distal end of the handle frame 506 such that tapered attachment portions 1212 formed on the tool chassis 1210 are aligned with dovetail slots 507 in the handle frame 506. The clinician may then move the surgical tool assembly 1000 along an installation axis IA that is perpendicular to the shaft axis SA to seat the tapered attachment portions 1212 in "operable engagement" with the corresponding dovetail receiving slots 507 in the distal end of the handle frame 506. In doing so, the firing shaft attachment lug 1314 on the intermediate firing shaft portion 1310 will also be seated in the cradle 544 in the longitudinally movable drive member 540 within the handle assembly 500 and the portions of a pin 516 on a closure link 514 will be seated in the corresponding hooks 1917 in the closure shuttle 1914. As used herein, the term "operable engagement" in the context of two components means that the two components are sufficiently engaged with each other so that upon application of an actuation motion thereto, the components may carry out their intended action, function and/or procedure. Also during this process, the onboard connector 1154 on the surgical tool assembly 1000 is coupled to the housing connector 562 that communicates with the microprocessor 560 that is supported in the handle assembly 500 or robotic system controller, for example.

During a typical surgical procedure, the clinician may introduce the surgical end effector 1500 into the surgical site through a trocar or other opening in the patient to access the target tissue. When doing so, the clinician typically axially aligns the surgical end effector 1500 along the shaft axis SA (unarticulated state). Once the surgical end effector 1500 has passed through the trocar port, for example, the clinician may need to articulate the end effector 1500 to advantageously position it adjacent the target tissue. This is prior to closing the anvil 1810 onto the target tissue, so the closure drive system 510 would remain unactuated. When in this position, actuation of the firing drive system 530 will result in the application of articulation motions to the proximal articulation driver 1370. Once the end effector 1500 has attained the desired articulated position, the firing drive system 530 is deactivated and the articulation lock 1390 may retain the surgical end effector 1500 in the articulated position. The clinician may then actuate the closure drive system 510 to close the anvil 1810 onto the target tissue. Such actuation of the closure drive system 510 may also result in the shifter assembly 1100 delinking the proximal articulation driver 1370 from the intermediate firing shaft portion 1310. Thus, once the target tissue has been captured in the surgical end effector 1500, the clinician may once again actuate the firing drive system 530 to axially advance the firing member 1330 through the surgical staple/fastener cartridge 1400 or RF cartridge 1700 to cut the clamped tissue and fire the staples/fasteners into the cut tissue T. Other closure and firing drive arrangements, actuator arrangements (both handheld, manual and automated or robotic) may also be employed to control the axial movement of the closure system components, the articulation system components and/or the firing system components of the surgical tool assembly 1000 without departing from the scope of the present disclosure.

As indicated above, the surgical tool assembly 1000 is configured to be used in connection with conventional mechanical surgical staple/fastener cartridges 1400 as well as with RF cartridges 1700. In at least one form, the RF cartridge 1700 may facilitate mechanical cutting of tissue that is clamped between the anvil 1810 and the RF cartridge 1700 with the knife member 1330 while coagulating electrical current is delivered to the tissue in the current path. Alternative arrangements for mechanically cutting and coagulating tissue using electrical current are disclosed in, for example, U.S. Pat. Nos. 5,403,312; 7,780,663 and U.S. patent application Ser. No. 15/142,609, entitled ELECTROSURGICAL INSTRUMENT WITH ELECTRICALLY CONDUCTIVE GAP SETTING AND TISSUE ENGAGING MEMBERS, the entire disclosures of each said references being incorporated by reference herein. Such instruments, may, for example, improve hemostasis, reduce surgical complexity as well as operating room time.

Figure 10:
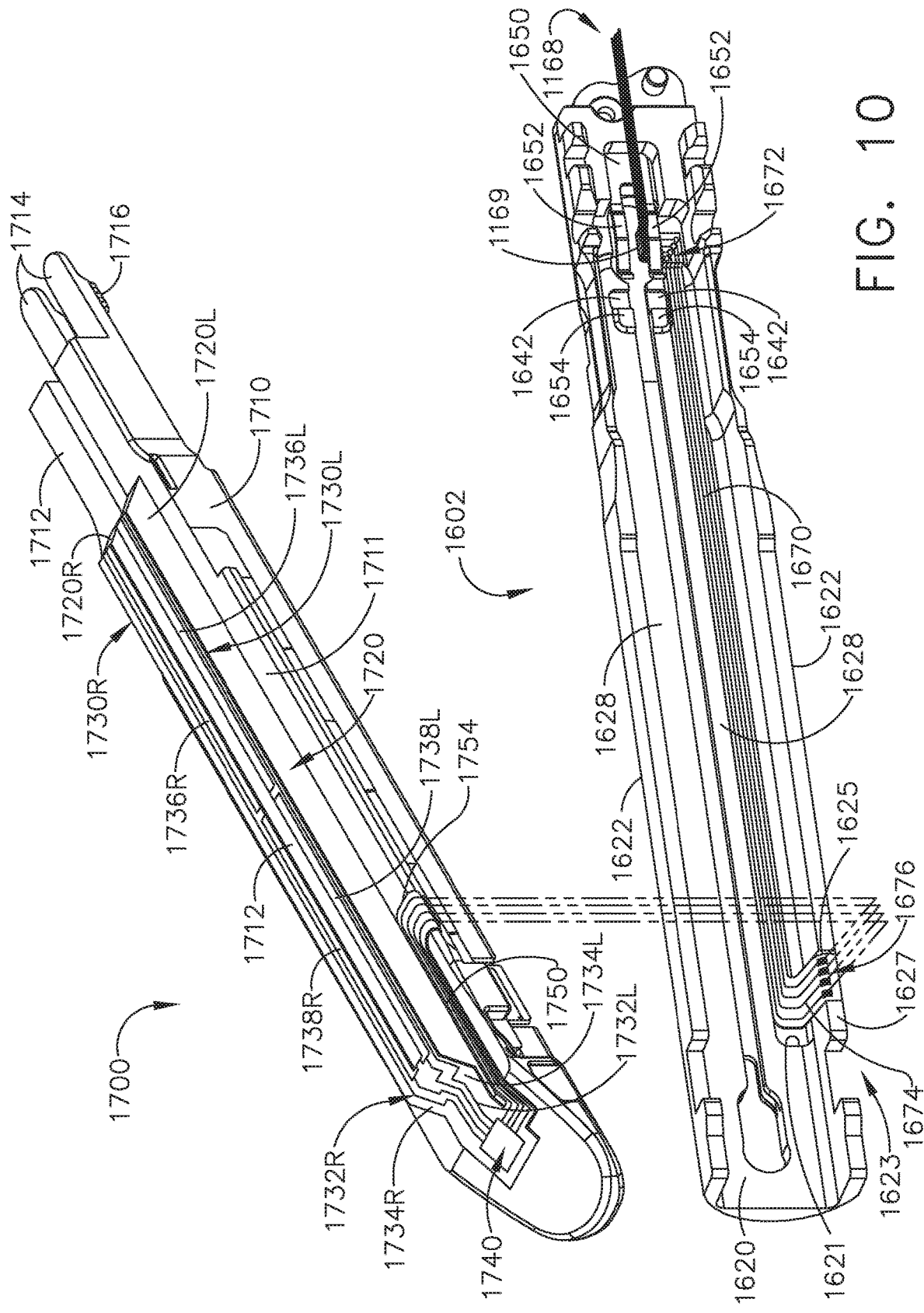
FIG. 10 is a perspective view of an RF cartridge and an elongate channel of the interchangeable surgical tool assembly of FIGS. 1-5 according to one aspect of this disclosure.
Figure 11:
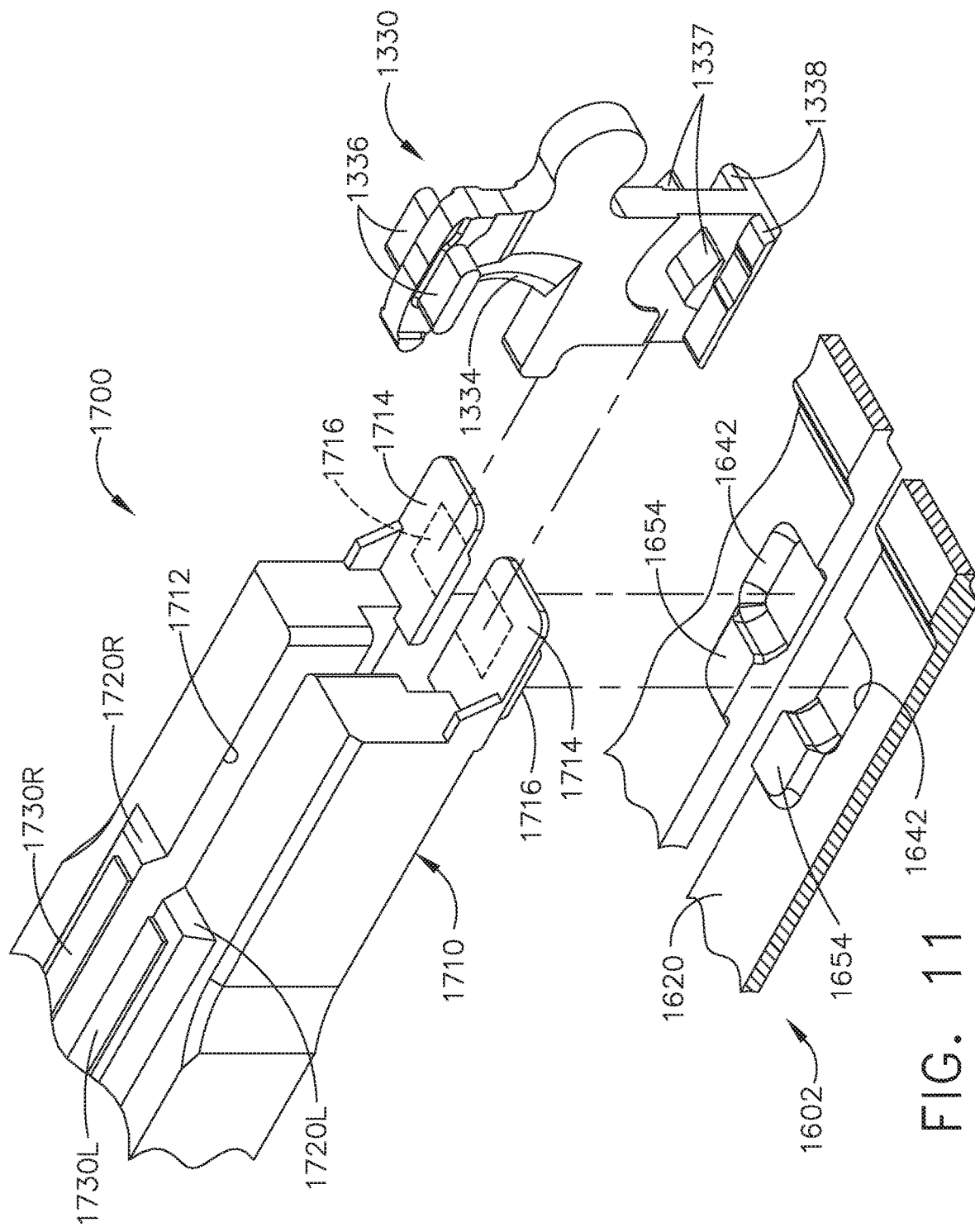
FIG. 11 is a partial perspective view of portions of the RF cartridge and elongate channel of FIG. 10 with a knife member according to one aspect of this disclosure.
Figure 12:
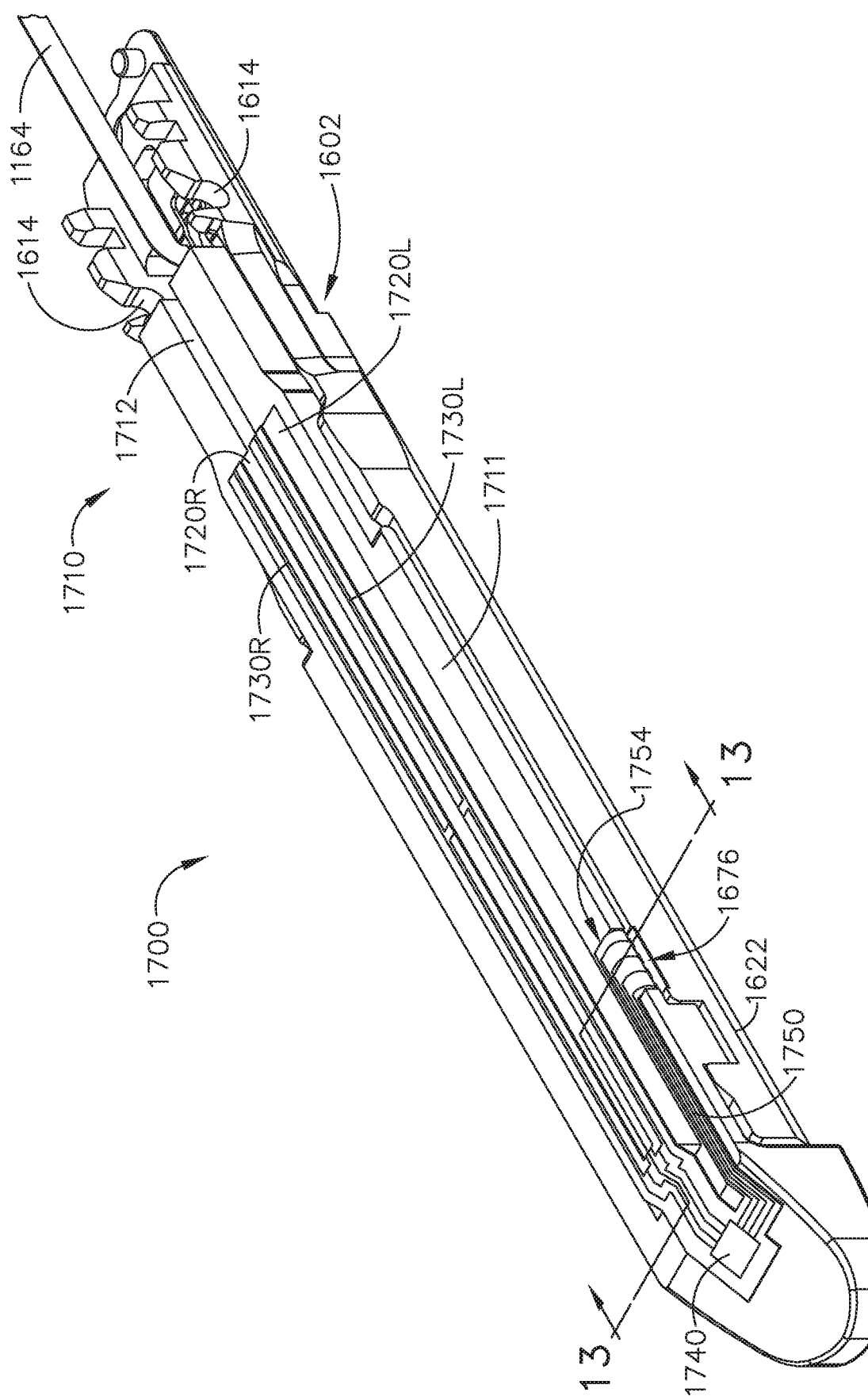
FIG. 12 is another perspective view of the RF cartridge installed in the elongate channel of FIG. 10 and illustrating a portion of a flexible shaft circuit arrangement according to one aspect of this disclosure.
Figure 13:
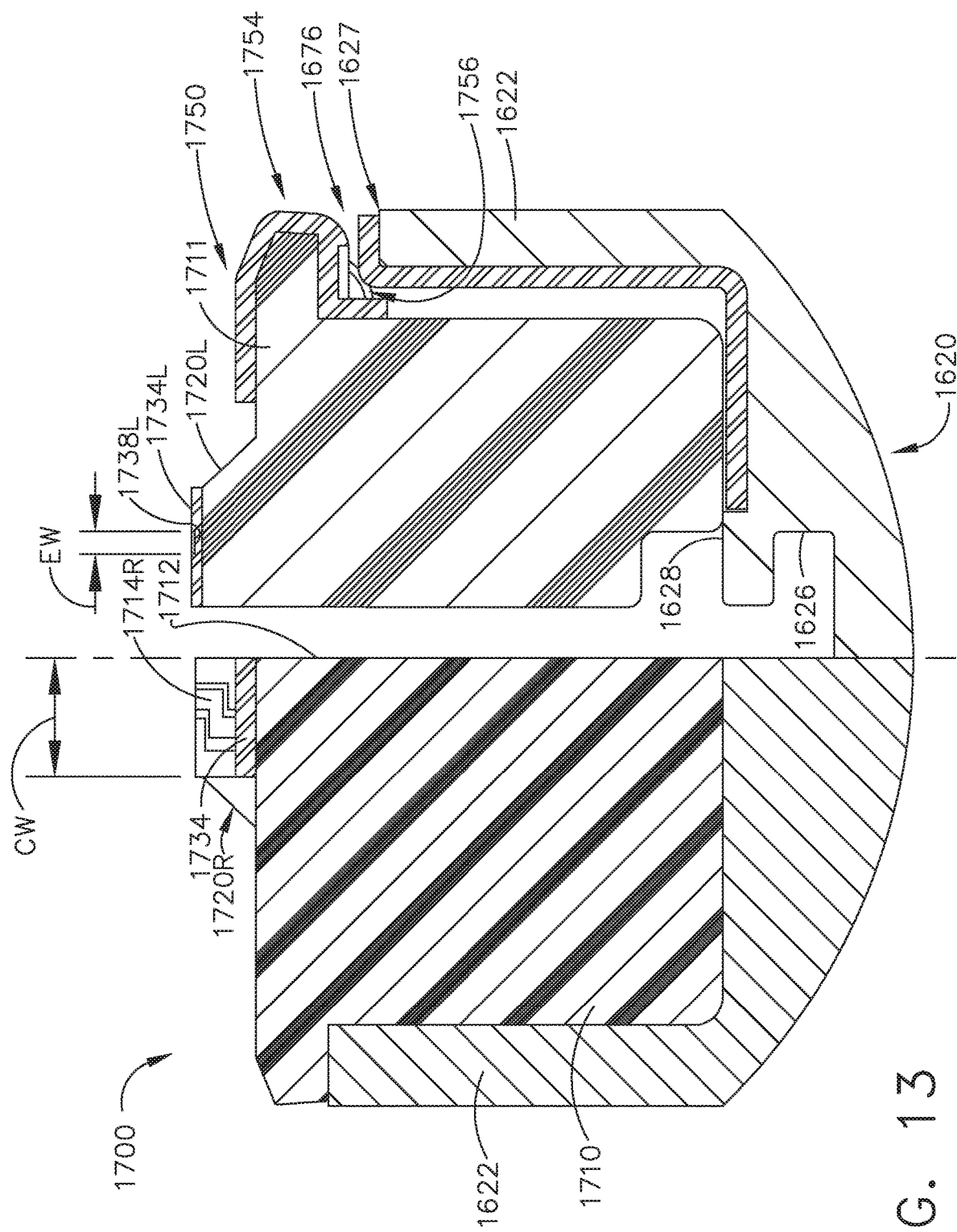
FIG. 13 is a cross-sectional end view of the RF cartridge and elongate channel of FIG. 12 taken along lines 13-13 in FIG. 12 according to one aspect of this disclosure.

As shown in FIGS. 10-12, in at least one arrangement, the RF surgical cartridge 1700 includes a cartridge body 1710 that is sized and shaped to be removably received and supported in the elongate channel 1602. For example, the cartridge body 1710 may be configured to be removably retained in snap engagement with the elongate channel 1602. In various arrangements, the cartridge body 1710 may be fabricated from a polymer material, such as, for example, an engineering thermoplastic such as the liquid crystal polymer (LCP) VECTRA™ and the elongate channel 1602 may be fabricated from metal. In at least one aspect, the cartridge body 1710 includes a centrally disposed elongate slot 1712 that extends longitudinally through the cartridge body to accommodate longitudinal travel of the knife 1330 therethrough. As shown in FIGS. 10 and 11, a pair of lockout engagement tails 1714 extend proximally from the cartridge body 1710. Each lockout engagement tail 1714 has a lockout pad 1716 formed on the underside thereof that are sized to be received within a corresponding proximal opening portion 1642 in the channel bottom 1620. Thus, when the cartridge 1700 is properly installed in the elongate channel 1602, the lockout engagement tails 1714 cover the openings 1642 and ledges 1654 to retain the knife 1330 in an unlocked position ready for firing.

Turning now to FIGS. 10-13, in the illustrated example, the cartridge body 1710 is formed with a centrally disposed raised electrode pad 1720. As can be most particularly seen in FIG. 6, the elongate slot 1712 extends through the center of the electrode pad 1720 and serves to divide the pad 1720 into a left pad segment 1720L and a right pad segment 1720R. A right flexible circuit assembly 1730R is attached to the right pad segment 1720R and a left flexible circuit assembly 1730L is attached to the left pad segment 1720L. In at least one arrangement for example, the right flexible circuit 1730R comprises a plurality of electrical conductors 1732R that may include, for example, wider electrical conductors/conductors for RF purposes and thinner electrical conductors for conventional stapling purposes that are supported or attached or embedded into a right insulator sheath/member 1734R that is attached to the right pad 1720R. In addition, the right flexible circuit assembly 1730R includes a "phase one", proximal right electrode 1736R and a "phase two" distal right electrode 1738R. Likewise, the left flexible circuit assembly 1730L comprises a plurality of electrical conductors 1732L that may include, for example, wider electrical conductors/conductors for RF purposes and thinner electrical conductors for conventional stapling purposes that are supported or attached or embedded into a left insulator sheath/member 1734L that is attached to the left pad 1720L. In addition, the left flexible circuit assembly 1730L includes a "phase one", proximal left electrode 1736L and a "phase two" distal left electrode 1738L. The left and right electrical conductors 1732L, 1732R are attached to a distal micro-chip 1740 mounted to the distal end portion of the cartridge body 1710. In one arrangement, for example, each of the right and left flexible circuits 1730R, 1730L may have an overall width "CW" of approximately 0.025 inches and each of the electrodes 1736R, 1736L, 1738R, 1738R has a width "EW" of approximately 0.010 inches for example. See FIG. 13. However, other widths/sizes are contemplated and may be employed in alternative aspects.

Figure 14:
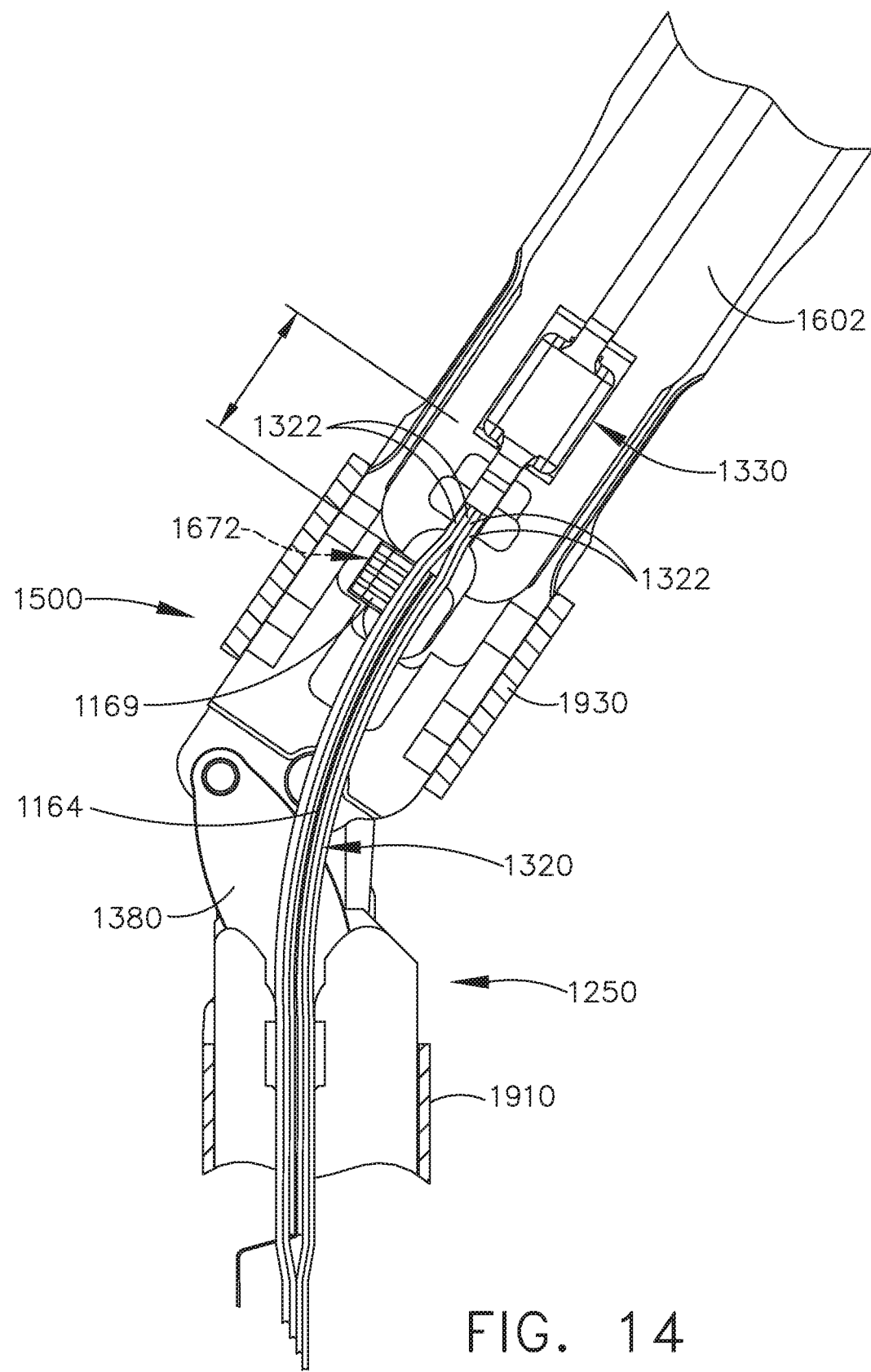
FIG. 14 is a top cross-sectional view of a portion of the interchangeable surgical tool assembly of FIGS. 1 and 5 with the end effector thereof in an articulated position according to one aspect of this disclosure.

In at least one arrangement, RF energy is supplied to the surgical tool assembly 1000 by a conventional RF generator 400 through a supply lead 402. In at least one arrangement, the supply lead 402 includes a male plug assembly 406 that is configured to be plugged into corresponding female connectors 410 that are attached to a segmented RF circuit 1160 on the an onboard circuit board 1152. See FIG. 15. Such arrangement facilitates rotational travel of the shaft and end effector 1500 about the shaft axis SA relative to the tool chassis 1210 by rotating the nozzle assembly 1240 without winding up the supply lead 402 from the generator 400. An onboard on/off power switch 420 is supported on the latch assembly 1280 and tool chassis 1210 for turning the RF generator on and off. When the tool assembly 1000 is operably coupled to the handle assembly 500 or robotic system, the onboard segmented RF circuit 1160 communicates with the microprocessor 560 through the connectors 1154 and 562. As shown in FIG. 1, the handle assembly 500 may also include a display screen 430 for viewing information about the progress of sealing, stapling, knife location, status of the cartridge, tissue, temperature, etc. As can also be seen FIG. 15, the slip ring assembly 1150 interfaces with a distal connector 1162 that includes a flexible shaft circuit strip or assembly 1164 that may include a plurality of narrow electrical conductors 1166 for stapling related activities and wider electrical conductors 1168 used for RF purposes. As shown in FIGS. 14 and 15, the flexible shaft circuit strip 1164 is centrally supported between the laminated plates or bars 1322 that form the knife bar 1320. Such arrangement facilitates sufficient flexing of the knife bar 1320 and flexible shaft circuit strip 1164 during articulation of the end effector 1500 while remaining sufficiently stiff so as to enable the knife member 1330 to be distally advanced through the clamped tissue.

Turning again to FIG. 10, in at least one illustrated arrangement, the elongate channel 1602 includes a channel circuit 1670 supported in a recess 1621 that extends from the proximal end 1610 of the elongate channel 1602 to a distal location 1623 in the elongate channel bottom portion 1620. The channel circuit 1670 includes a proximal contact portion 1672 that contacts a distal contact portion 1169 of the flexible shaft circuit strip 1164 for electrical contact therewith. A distal end 1674 of the channel circuit 1670 is received within a corresponding wall recess 1625 formed in one of the channel walls 1622 and is folded over and attached to an upper edge 1627 of the channel wall 1622. A series of corresponding exposed contacts 1676 are provided in the distal end 1674 of the channel circuit 1670 As shown in FIG. 10. As can also be seen in FIG. 10, an end 1752 of a flexible cartridge circuit 1750 is attached to the distal micro-chip 1740 and is affixed to the distal end portion of the cartridge body 1710. Another end 1754 is folded over the edge of the cartridge deck surface 1711 and includes exposed contacts 1756 configured to make electrical contact with the exposed contacts 1676 of the channel circuit 1670. Thus, when the RF cartridge 1700 is installed in the elongate channel 1602, the electrodes as well as the distal micro-chip 1740 are powered and communicate with the onboard circuit board 1152 through contact between the flexible cartridge circuit 1750, the flexible channel circuit 1670, the flexible shaft circuit 1164 and the slip ring assembly 1150.

Figure 16A:
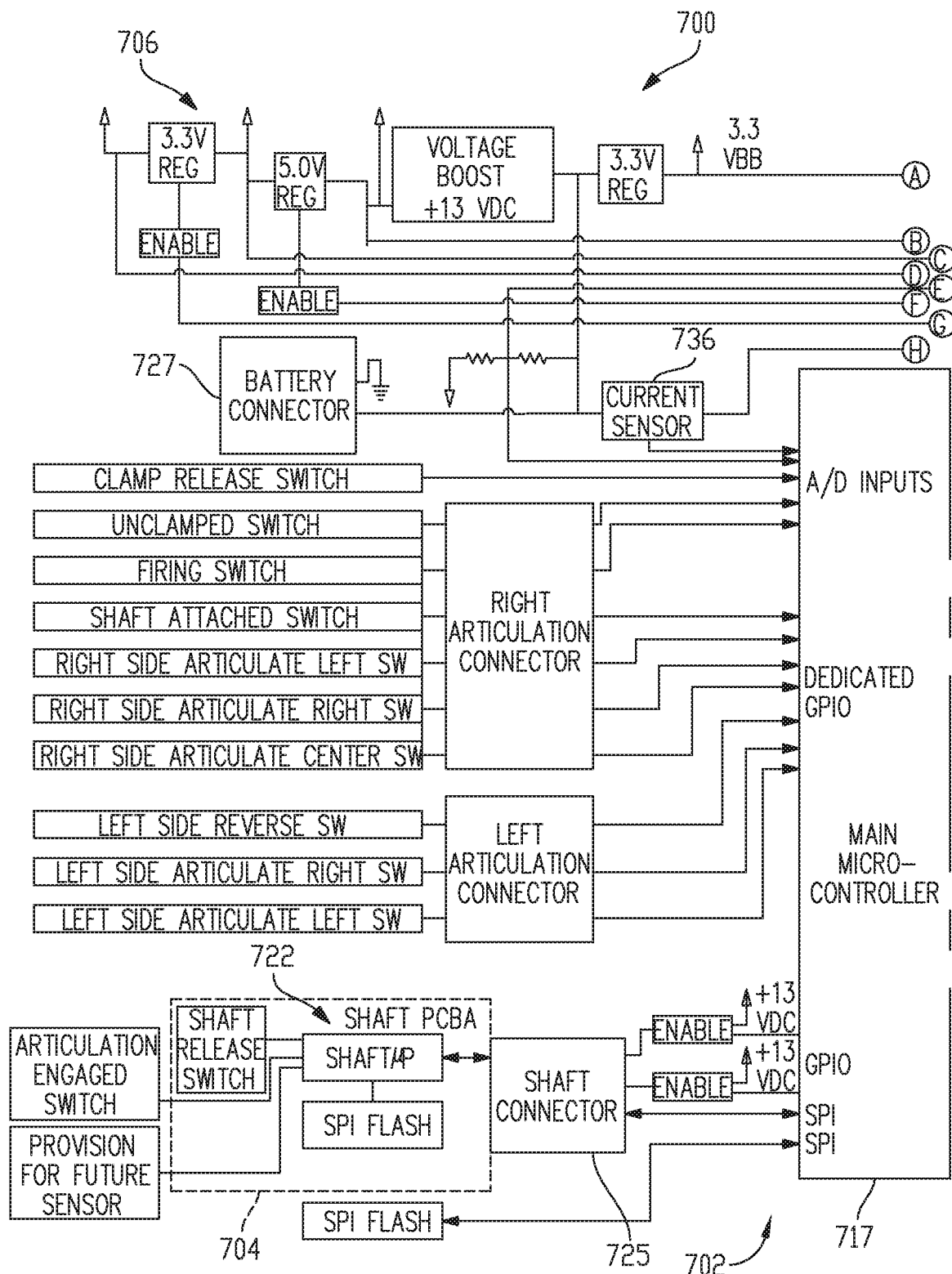
FIGS. 16A-16B is a block diagram of a control circuit of the surgical instrument of FIG. 1 spanning two drawing sheets according to one aspect of this disclosure.
Figure 16B:
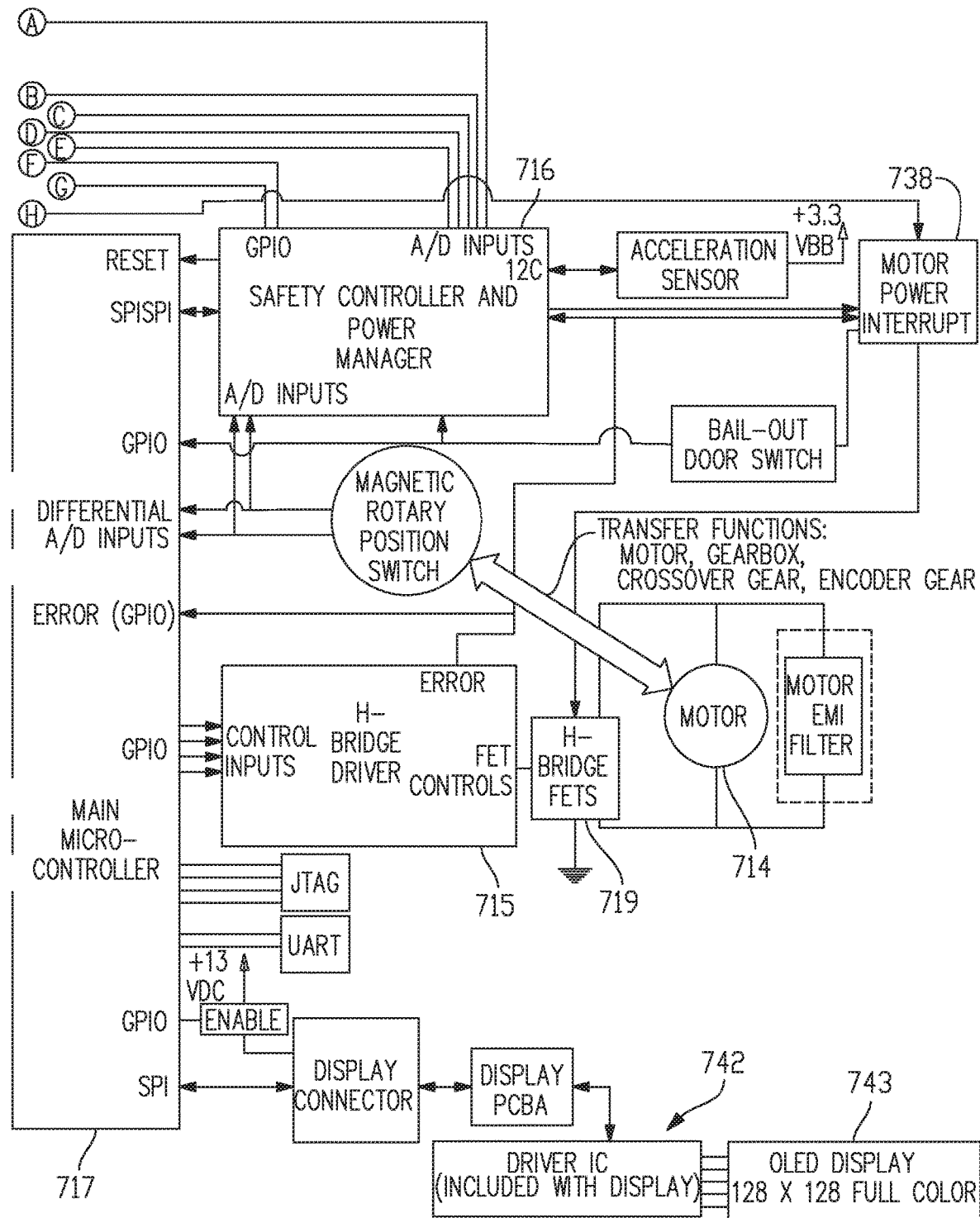

FIGS. 16A-16B is a block diagram of a control circuit 700 of the surgical instrument 10 of FIG. 1 spanning two drawing sheets according to one aspect of this disclosure. Referring primarily to FIGS. 16A-16B, a handle assembly 702 may include a motor 714 which can be controlled by a motor driver 715 and can be employed by the firing system of the surgical instrument 10. In various forms, the motor 714 may be a DC brushed driving motor having a maximum rotational speed of approximately 25,000 RPM. In other arrangements, the motor 714 may include a brushless motor, a cordless motor, a synchronous motor, a stepper motor, or any other suitable electric motor. The motor driver 715 may comprise an H-Bridge driver comprising field-effect transistors (FETs) 719, for example. The motor 714 can be powered by the power assembly 706 releasably mounted to the handle assembly 500 for supplying control power to the surgical instrument 10. The power assembly 706 may comprise a battery which may include a number of battery cells connected in series that can be used as the power source to power the surgical instrument 10. In certain circumstances, the battery cells of the power assembly 706 may be replaceable and/or rechargeable. In at least one example, the battery cells can be Lithium-Ion batteries which can be separably couplable to the power assembly 706.

The shaft assembly 704 may include a shaft assembly controller 722 which can communicate with a safety controller and power management controller 716 through an interface while the shaft assembly 704 and the power assembly 706 are coupled to the handle assembly 702. For example, the interface may comprise a first interface portion 725 which may include one or more electric connectors for coupling engagement with corresponding shaft assembly electric connectors and a second interface portion 727 which may include one or more electric connectors for coupling engagement with corresponding power assembly electric connectors to permit electrical communication between the shaft assembly controller 722 and the power management controller 716 while the shaft assembly 704 and the power assembly 706 are coupled to the handle assembly 702. One or more communication signals can be transmitted through the interface to communicate one or more of the power requirements of the attached interchangeable shaft assembly 704 to the power management controller 716. In response, the power management controller may modulate the power output of the battery of the power assembly 706, as described below in greater detail, in accordance with the power requirements of the attached shaft assembly 704. The connectors may comprise switches which can be activated after mechanical coupling engagement of the handle assembly 702 to the shaft assembly 704 and/or to the power assembly 706 to allow electrical communication between the shaft assembly controller 722 and the power management controller 716.

The interface can facilitate transmission of the one or more communication signals between the power management controller 716 and the shaft assembly controller 722 by routing such communication signals through a main controller 717 residing in the handle assembly 702, for example. In other circumstances, the interface can facilitate a direct line of communication between the power management controller 716 and the shaft assembly controller 722 through the handle assembly 702 while the shaft assembly 704 and the power assembly 706 are coupled to the handle assembly 702.

The main controller 717 may be any single core or multicore processor such as those known under the trade name ARM Cortex by Texas Instruments. In one aspect, the main controller 717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 706 may include a power management circuit which may comprise the power management controller 716, a power modulator 738, and a current sense circuit 736. The power management circuit can be configured to modulate power output of the battery based on the power requirements of the shaft assembly 704 while the shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery so that the power management controller 716 may adjust the power output of the power assembly 706 to maintain a desired output. The power management controller 716 and/or the shaft assembly controller 722 each may comprise one or more processors and/or memory units which may store a number of software modules.

The surgical instrument 10 (FIGS. 1-5) may comprise an output device 742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 742 may comprise a display 743 which may be included in the handle assembly 702. The shaft assembly controller 722 and/or the power management controller 716 can provide feedback to a user of the surgical instrument 10 through the output device 742. The interface can be configured to connect the shaft assembly controller 722 and/or the power management controller 716 to the output device 742. The output device 742 can instead be integrated with the power assembly 706. In such circumstances, communication between the output device 742 and the shaft assembly controller 722 may be accomplished through the interface while the shaft assembly 704 is coupled to the handle assembly 702.

The control circuit 700 comprises circuit segments configured to control operations of the powered surgical instrument 10. A safety controller segment (Segment 1) comprises a safety controller and the main controller 717 segment (Segment 2). The safety controller and/or the main controller 717 are configured to interact with one or more additional circuit segments such as an acceleration segment, a display segment, a shaft segment, an encoder segment, a motor segment, and a power segment. Each of the circuit segments may be coupled to the safety controller and/or the main controller 717. The main controller 717 is also coupled to a flash memory. The main controller 717 also comprises a serial communication interface. The main controller 717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The main controller 717 is a multipurpose, programmable device that accepts digital data as input, processes it according to instructions stored in its memory, and provides results as output. It is an example of sequential digital logic, as it has internal memory. The control circuit 700 can be configured to implement one or more of the processes described herein.

The acceleration segment (Segment 3) comprises an accelerometer. The accelerometer is configured to detect movement or acceleration of the powered surgical instrument 10. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 717.

The display segment (Segment 4) comprises a display connector coupled to the main controller 717. The display connector couples the main controller 717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 500 coupled to the surgical instrument 10 (FIGS. 1-5) and/or one or more controls for an end effector 1500 coupled to the interchangeable shaft assembly 500. The shaft segment comprises a shaft connector configured to couple the main controller 717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 500 and/or the shaft PCBA. The shaft PCBA may be coupled to the interchangeable shaft assembly 500 and/or integral with the surgical instrument 10. In some examples, the shaft segment comprises a second shaft EEPROM. The second shaft EEPROM comprises a plurality of algorithms, routines, parameters, and/or other data corresponding to one or more shaft assemblies 500 and/or end effectors 1500 that may be interfaced with the powered surgical instrument 10.

The position encoder segment (Segment 6) comprises one or more magnetic angle rotary position encoders. The one or more magnetic angle rotary position encoders are configured to identify the rotational position of the motor 714, an interchangeable shaft assembly 500, and/or an end effector 1500 of the surgical instrument 10 (FIGS. 1-5). In some examples, the magnetic angle rotary position encoders may be coupled to the safety controller and/or the main controller 717.

The motor circuit segment (Segment 7) comprises a motor 714 configured to control movements of the powered surgical instrument 10 (FIGS. 1-5). The motor 714 is coupled to the main microcontroller processor 717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 717 and/or the safety controller. In some examples, the motor 714 is coupled to a motor electromagnetic interference (EMI) filter.

The motor controller controls a first motor flag and a second motor flag to indicate the status and position of the motor 714 to the main controller 717. The main controller 717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 717. The switches may be configured to control operations of the surgical instrument 10 (FIGS. 1-5), of the segmented circuit, and/or indicate a status of the surgical instrument 10. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 500 (FIGS. 1 and 3) and/or the end effector 300 (FIGS. 1 and 4). A left side reverse switch and a right side reverse switch are coupled to the main controller 717. The left side switches comprising the left side articulation left switch, the left side articulation right switch, the left side articulation center switch, and the left side reverse switch are coupled to the main controller 717 by a left flex connector. The right side switches comprising the right side articulation left switch, the right side articulation right switch, the right side articulation center switch, and the right side reverse switch are coupled to the main controller 717 by a right flex connector. A firing switch, a clamp release switch, and a shaft engaged switch are coupled to the main controller 717.

Any suitable mechanical, electromechanical, or solid state switches may be employed to implement the plurality of switches, in any combination. For example, the switches may be limit switches operated by the motion of components associated with the surgical instrument 10 (FIGS. 1-5) or the presence of an object. Such switches may be employed to control various functions associated with the surgical instrument 10. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include electrical conductorless switches, ultrasonic switches, accelerometers, inertial sensors, among others.

Figure 17:
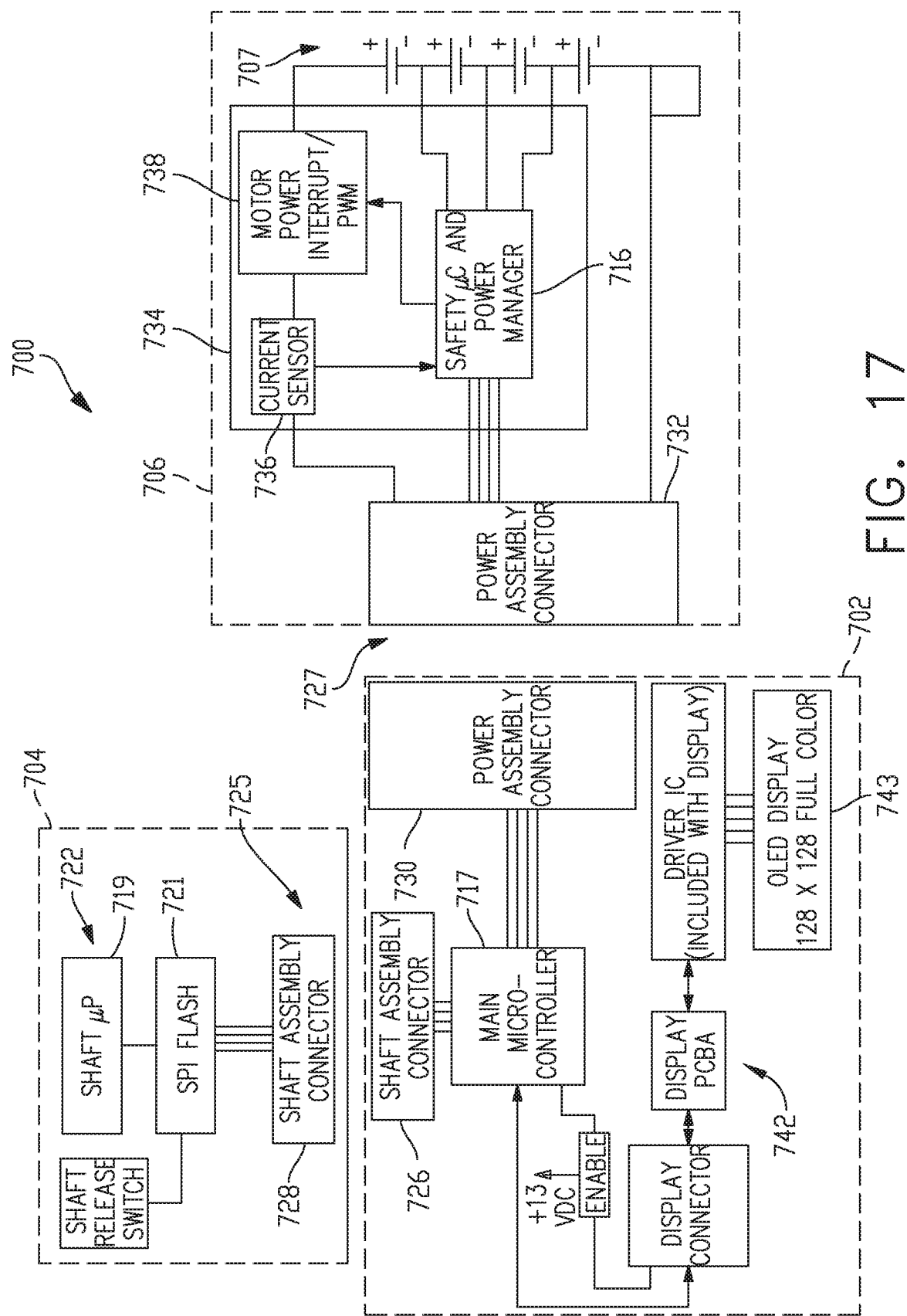
FIG. 17 is a block diagram of the control circuit of the surgical instrument of FIG. 1 illustrating interfaces between the handle assembly, the power assembly, and the handle assembly and the interchangeable shaft assembly according to one aspect of this disclosure.

FIG. 17 is another block diagram of the control circuit 700 of the surgical instrument of FIG. 1 illustrating interfaces between the handle assembly 702 and the power assembly 706 and between the handle assembly 702 and the interchangeable shaft assembly 704 according to one aspect of this disclosure. The handle assembly 702 may comprise a main controller 717, a shaft assembly connector 726 and a power assembly connector 730. The power assembly 706 may include a power assembly connector 732, a power management circuit 734 that may comprise the power management controller 716, a power modulator 738, and a current sense circuit 736. The shaft assembly connectors 730, 732 form an interface 727. The power management circuit 734 can be configured to modulate power output of the battery 707 based on the power requirements of the interchangeable shaft assembly 704 while the interchangeable shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery 707 so that the power management controller 716 may adjust the power output of the power assembly 706 to maintain a desired output. The shaft assembly 704 comprises a shaft processor 719 coupled to a non-volatile memory 721 and shaft assembly connector 728 to electrically couple the shaft assembly 704 to the handle assembly 702. The shaft assembly connectors 726, 728 form interface 725. The main controller 717, the shaft processor 719, and/or the power management controller 716 can be configured to implement one or more of the processes described herein.

The surgical instrument 10 (FIGS. 1-5) may comprise an output device 742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 742 may comprise a display 743 that may be included in the handle assembly 702. The shaft assembly controller 722 and/or the power management controller 716 can provide feedback to a user of the surgical instrument 10 through the output device 742. The interface 727 can be configured to connect the shaft assembly controller 722 and/or the power management controller 716 to the output device 742. The output device 742 can be integrated with the power assembly 706. Communication between the output device 742 and the shaft assembly controller 722 may be accomplished through the interface 725 while the interchangeable shaft assembly 704 is coupled to the handle assembly 702. Having described a control circuit 700 (FIGS. 16A-16B and 6) for controlling the operation of the surgical instrument 10 (FIGS. 1-5), the disclosure now turns to various configurations of the surgical instrument 10 (FIGS. 1-5) and control circuit 700.

Figure 18:
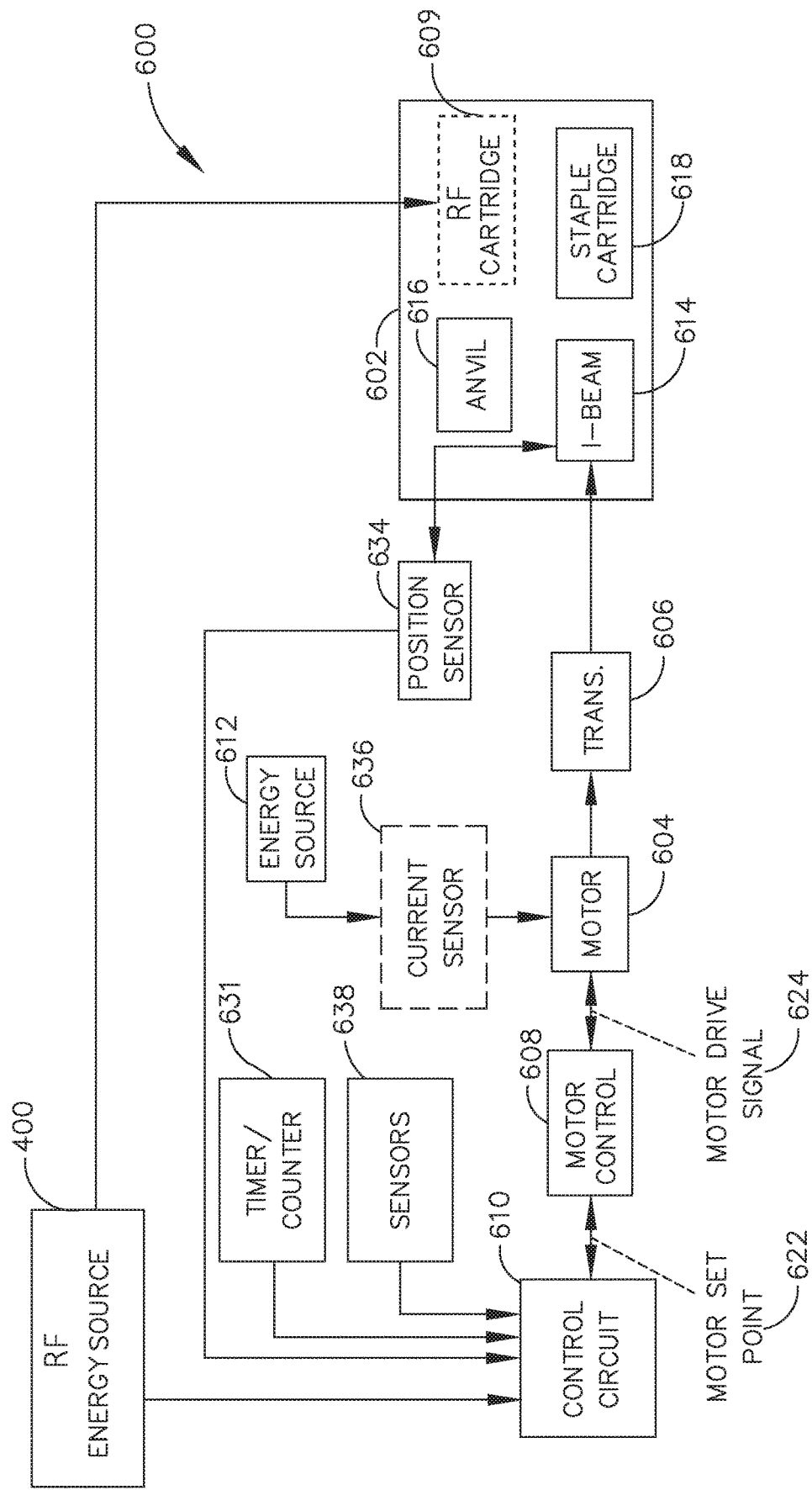
FIG. 18 is a schematic diagram of a surgical instrument configured to control various functions according to one aspect of this disclosure.

FIG. 18 is a schematic diagram of a surgical instrument 600 configured to control various functions according to one aspect of this disclosure. In one aspect, the surgical instrument 600 is programmed to control distal translation of a displacement member such as the I-beam 614. The surgical instrument 600 comprises an end effector 602 that may comprise an anvil 616, an I-beam 614, and a removable staple cartridge 618 which may be interchanged with an RF cartridge 609 (shown in dashed line). The end effector 602, anvil 616, I-beam 614, staple cartridge 618, and RF cartridge 609 may be configured as described herein, for example, with respect to FIGS. 1-15. For conciseness and clarity of disclosure, several aspects of the present disclosure may be described with reference to FIG. 18. It will be appreciated that the components shown schematically in FIG. 18 such as the control circuit 610, sensors 638, position sensor 634, end effector 602, I-beam 614, staple cartridge 618, RF cartridge 609, anvil 616, are described in connection with FIGS. 1-17 of this disclosure.

Accordingly, the components represented schematically in FIG. 18 may be readily substituted with the physical and functional equivalent components described in connection with FIGS. 1-17. For example, in one aspect, the control circuit 610 may be implemented as the control circuit 700 shown and described in connection with FIGS. 16-17. In one aspect, the sensors 638 may be implemented as a limit switch, electromechanical device, solid state switches, Hall-effect devices, magneto-resistive (MR) devices, giant magneto-resistive (GMR) devices, magnetometers, among others. In other implementations, the sensors 638 may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). In other implementations, the sensors 638 may include electrical conductorless switches, ultrasonic switches, accelerometers, inertial sensors, among others. In one aspect, the position sensor 634 may be implemented as an absolute positioning system comprising a magnetic rotary absolute positioning system implemented as an AS5055EQFT single-chip magnetic rotary position sensor available from Austria Microsystems, AG. The position sensor 634 may interface with the control circuit 700 to provide an absolute positioning system. The position may include multiple Hall-effect elements located above a magnet and coupled to a CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. In one aspect, the end effector 602 may be implemented as surgical end effector 1500 shown and described in connection with FIGS. 1, 2, and 4. In one aspect, the I-beam 614 may be implemented as the knife member 1330 comprising a knife body 1332 that operably supports a tissue cutting blade 1334 thereon and may further include anvil engagement tabs or features 1336 and channel engagement features or a foot 1338 as shown and described in connection with FIGS. 2-4, 8, 11 and 14. In one aspect, the staple cartridge 618 may be implemented as the standard (mechanical) surgical fastener cartridge 1400 shown and described in connection with FIG. 4. In one aspect, the RF cartridge 609 may be implemented as the radio frequency (RF) cartridge 1700 shown and described in connection with FIGS. 1, 2, 6, and 10-13. In one aspect, the anvil 616 may be implemented the anvil 1810 shown and described in connection with FIGS. 1, 2, 4, and 6. These and other sensors arrangements are described in commonly owned U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is incorporated herein by reference in its entirety.

The position, movement, displacement, and/or translation of a liner displacement member, such as the I-beam 614, can be measured by an absolute positioning system, sensor arrangement, and position sensor represented as position sensor 634. Because the I-beam 614 is coupled to the longitudinally movable drive member 540, the position of the I-beam 614 can be determined by measuring the position of the longitudinally movable drive member 540 employing the position sensor 634. Accordingly, in the following description, the position, displacement, and/or translation of the I-beam 614 can be achieved by the position sensor 634 as described herein. A control circuit 610, such as the control circuit 700 described in FIGS. 16A and 16B, may be programmed to control the translation of the displacement member, such as the I-beam 614, as described herein. The control circuit 610, in some examples, may comprise one or more microcontrollers, microprocessors, or other suitable processors for executing instructions that cause the processor or processors to control the displacement member, e.g., the I-beam 614, in the manner described. In one aspect, a timer/counter circuit 631 provides an output signal, such as elapsed time or a digital count, to the control circuit 610 to correlate the position of the I-beam 614 as determined by the position sensor 634 with the output of the timer/counter circuit 631 such that the control circuit 610 can determine the position of the I-beam 614 at a specific time (t) relative to a starting position. The timer/counter circuit 631 may be configured to measure elapsed time, count external evens, or time external events.

The control circuit 610 may generate a motor set point signal 622. The motor set point signal 622 may be provided to a motor controller 608. The motor controller 608 may comprise one or more circuits configured to provide a motor drive signal 624 to the motor 604 to drive the motor 604 as described herein. In some examples, the motor 604 may be a brushed DC electric motor, such as the motor 505 shown in FIG. 1. For example, the velocity of the motor 604 may be proportional to the motor drive signal 624. In some examples, the motor 604 may be a brushless direct current (DC) electric motor and the motor drive signal 624 may comprise a pulse-width-modulated (PWM) signal provided to one or more stator windings of the motor 604. Also, in some examples, the motor controller 608 may be omitted and the control circuit 610 may generate the motor drive signal 624 directly.

The motor 604 may receive power from an energy source 612. The energy source 612 may be or include a battery, a super capacitor, or any other suitable energy source 612. The motor 604 may be mechanically coupled to the I-beam 614 via a transmission 606. The transmission 606 may include one or more gears or other linkage components to couple the motor 604 to the I-beam 614. A position sensor 634 may sense a position of the I-beam 614. The position sensor 634 may be or include any type of sensor that is capable of generating position data that indicates a position of the I-beam 614. In some examples, the position sensor 634 may include an encoder configured to provide a series of pulses to the control circuit 610 as the I-beam 614 translates distally and proximally. The control circuit 610 may track the pulses to determine the position of the I-beam 614. Other suitable position sensor may be used, including, for example, a proximity sensor. Other types of position sensors may provide other signals indicating motion of the I-beam 614. Also, in some examples, the position sensor 634 may be omitted. Where the motor 604 is a stepper motor, the control circuit 610 may track the position of the I-beam 614 by aggregating the number and direction of steps that the motor 604 has been instructed to execute. The position sensor 634 may be located in the end effector 602 or at any other portion of the instrument.

The control circuit 610 may be in communication with one or more sensors 638. The sensors 638 may be positioned on the end effector 602 and adapted to operate with the surgical instrument 600 to measure the various derived parameters such as gap distance versus time, tissue compression versus time, and anvil strain versus time. The sensors 638 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 602. The sensors 638 may include one or more sensors.

The one or more sensors 638 may comprise a strain gauge, such as a micro-strain gauge, configured to measure the magnitude of the strain in the anvil 616 during a clamped condition. The strain gauge provides an electrical signal whose amplitude varies with the magnitude of the strain. The sensors 638 may comprise a pressure sensor configured to detect a pressure generated by the presence of compressed tissue between the anvil 616 and the staple cartridge 618. The sensors 638 may be configured to detect impedance of a tissue section located between the anvil 616 and the staple cartridge 618 that is indicative of the thickness and/or fullness of tissue located therebetween.

The sensors 638 may be is configured to measure forces exerted on the anvil 616 by the closure drive system. For example, one or more sensors 638 can be at an interaction point between the closure tube 1910 (FIGS. 1-4) and the anvil 616 to detect the closure forces applied by the closure tube 1910 to the anvil 616. The forces exerted on the anvil 616 can be representative of the tissue compression experienced by the tissue section captured between the anvil 616 and the staple cartridge 618. The one or more sensors 638 can be positioned at various interaction points along the closure drive system to detect the closure forces applied to the anvil 616 by the closure drive system. The one or more sensors 638 may be sampled in real time during a clamping operation by a processor as described in FIGS. 16A-16B. The control circuit 610 receives real-time sample measurements to provide analyze time based information and assess, in real time, closure forces applied to the anvil 616.

A current sensor 636 can be employed to measure the current drawn by the motor 604. The force required to advance the I-beam 614 corresponds to the current drawn by the motor 604. The force is converted to a digital signal and provided to the control circuit 610.

The RF energy source 400 is coupled to the end effector 602 and is applied to the RF cartridge 609 when the RF cartridge 609 is loaded in the end effector 602 in place of the staple cartridge 618. The control circuit 610 controls the delivery of the RF energy to the RF cartridge 609.

Generally, it is difficult to provide electrosurgical energy to low impedance tissue continuously until welding of the tissue is substantially completed. For example, when providing the electrosurgical energy to low impedance tissue, there is a point where the tissue impedance becomes too low, acting like a short circuit so that the tissue merely draws a lot of current while providing no or little electrosurgical energy to the tissue. This can result in several undesirable outcomes including, for example, incomplete tissue welding, excessive heating of the electrodes, a delay of the surgery, clinician inconvenience or frustration, etc.

Aspects of the present disclosure may address the above noted deficiency by controlling control circuits for an independent energy delivery over segmented sections. In an example aspect, a surgical instrument may include an end effector having a first jaw with a distal portion and a proximate portion, a second jaw that is movable relative to the first jaw, a first set of electrodes located in the distal portion of the first jaw, and a second set of electrodes located in the proximate portion of the first jaw. The surgical instrument also may include a control circuit configured to provide electrosurgical energy (e.g., RF energy) to the first set of electrodes and the second set of electrodes. The electrosurgical energy provided to the first set of electrodes and the second set of electrodes may repeatedly alternate between the first set of electrodes and the second set of electrodes at a predetermined time interval. For example, the electrosurgical energy may be provided to the first set of electrodes for a first period of time (e.g., 0.25 seconds), to the second set of electrodes for a second period of time (e.g., 0.25 seconds) after the first period of time and, then, to the first set of electrodes for a third period of time (0.25 seconds), and so on. The alternation of the electrosurgical energy between the first set of electrodes and the second set of electrodes may be repeated, for example, until the welding of the tissue starts to complete or is substantially completed. The alternation of the electrosurgical energy at a very short period of time interval (e.g., 0.25 seconds) between the first set of electrodes and the second set of electrodes may facilitate the complete welding of low impedance tissue without excessive heating of the electrodes or a delay of the surgery. In an example, this alternation of the electrosurgical energy may be carried out by a microchip in the first jaw or a processor in the body of the surgical instrument using the RF energy provided from a conventional RF energy generator.

In this way, aspects of the present disclosure may enable the surgical instrument to provide the electrosurgical energy to the tissue having low impedance until the welding of the low impedance tissue is substantially completed. Moreover, aspects of the present disclosure may advantageously use the microchip in the first jaw or a processor in the body of the surgical instrument to alternate the electrosurgical energy between the two sets of electrodes using the RF energy from a conventional RF energy generator.

Figure 19:
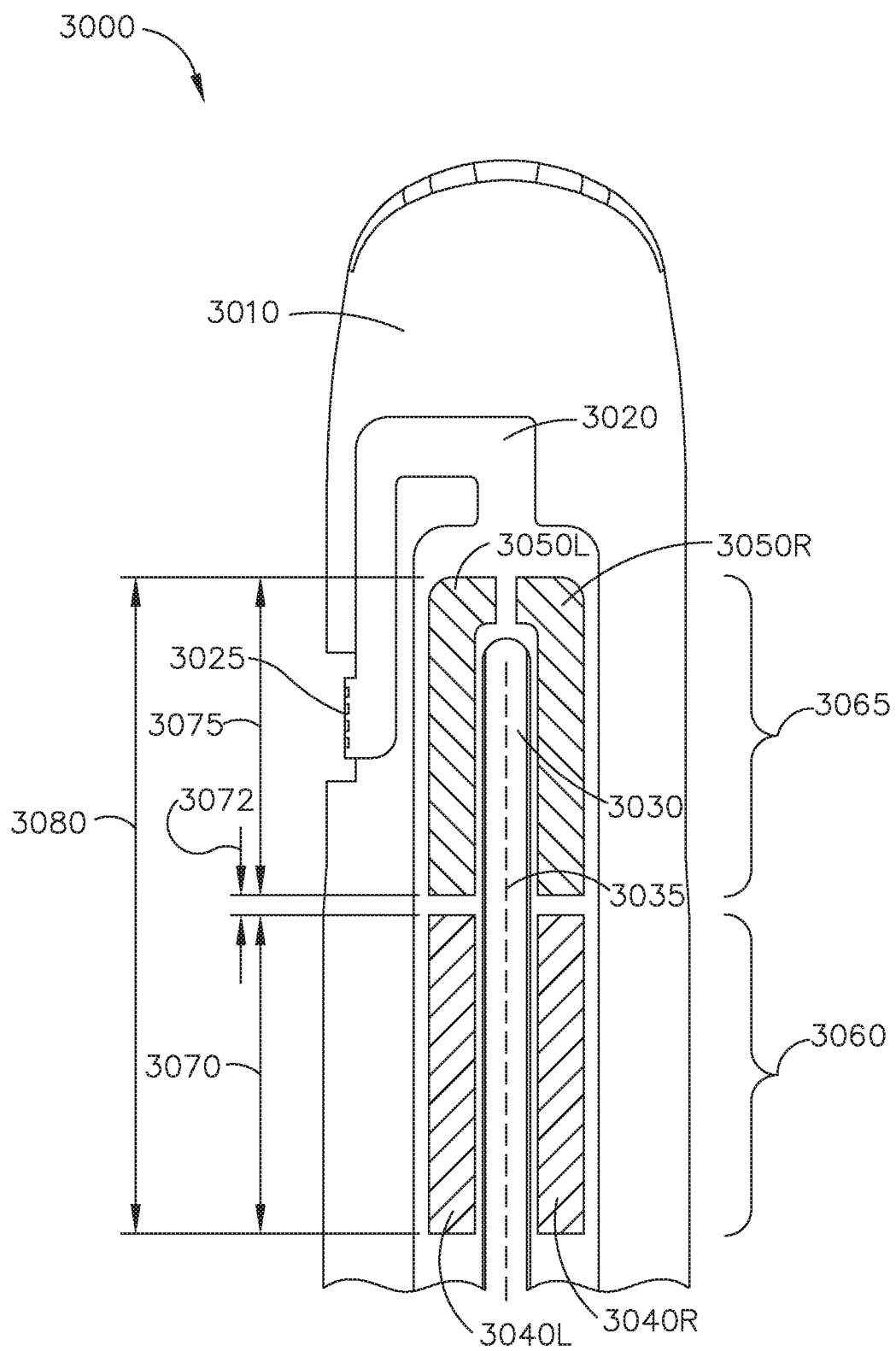
FIG. 19 is a schematic top view of a jaw in an end effector according to one aspect of this disclosure.

FIG. 19 shows a schematic top view of a jaw 3000 in an end effector (e.g., end effector 1500) of a surgical instrument (e.g., surgical system 10 or surgical tool assembly 1000) according to one aspect of this disclosure. The jaw 3000 may include a cartridge 3010, a flex circuit 3020 having flex circuit contacts 3025 (e.g., exposed contacts 1756), and an elongate slot 3030, within which a cutting member (e.g., knife member 1330) is slidably receivable to cut tissue clamped within the end effector along a cutting line 3035. The elongate slot may extend from a proximate end of the jaw 3000. In an example aspect, the flex circuit 3020 also may include a microchip (e.g., distal micro-chip 1740) and, then, the cartridge 3010 may be referred to as a smart cartridge. The jaw 3000 also may include a first set of electrodes 3040L, 3040R in a first zone 3060, and a second set of electrodes 3050L, 3050R in a second zone 3065. In an example aspect, the first zone 3060 may be located in a proximate portion of the jaw 3000 and the second zone 3065 may be located in a distal portion of the jaw 3000. In another example aspect, the first zone 3060 and the second zone 3065 may be located in any other suitable places of the jaw 3000.

The first and second set of electrodes 3040L, 3040R, 3050L, 3050R may be in communication with and/or deposited on the flex circuit 3020. In an example, the elongate slot 3030 may be disposed in the center of the jaw 3000. In another example, the elongate slot 3000 may be disposed in any other suitable places in the jaw 3000. As seen in FIG. 16, the electrodes 3040L and 3050L may be located on the left side of the elongate slot 3030 and the electrodes 3040R and 3050R may be located on the right side of the elongate slot 3030. In an example aspect, a control circuit (e.g., microprocessor 560, segmented RF circuit 1160, or distal micro-chip 1740) may be configured to provide electrosurgical energy to the first set of electrodes 3040L, 3040R and the second set of electrodes 3050L, 3050R.

The electrosurgical energy may be in the form of radio frequency (RF) energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat. The first set of electrodes 3040L, 3040R and the second set of electrodes 3050L, 3050R may be electronically connected to the control circuit through the flex circuit 3020. The first set of electrodes 3040L, 3040R and the second set of electrodes 3050L, 3050R may be configured to emit RF energy to form a hemostatic (or a coagulation) line on the tissue adjacent the electrodes 3040L, 3040R, 3050L, 3050R along the cutting line 3035.

In an example aspect, the length 3070 of the first set of electrodes 3040L, 3040R may be in the range of about 10 mm to about 100 mm, preferably in the range of about 20 mm to about 50 mm, more preferably in the range of about 25 mm to about 35 mm. Similarly, in an example aspect, the length 3075 of the second set of electrodes 3050L, 3050R may be in the range of about 10 mm to about 100 mm, preferably in the range of about 20 mm to about 50 mm, more preferably in the range of about 25 mm to about 35 mm. In another example aspect, the first set of electrodes 3040L, 3040R and the second set of electrodes 3050L, 3050R may have any other suitable length. In an example aspect, a gap between the first set of electrodes 3040L, 3040R and the second set of electrodes 3050L, 3050R may be very small so that the claimed tissue may be welded from the first zone 3060 to the second zone 3065 continuously with no tissue located between the two zones 3060 and 3065 being unsealed/welded. In an example aspect, the length 3072 of the gap between the first set of electrodes 3040L, 3040R and the second set of electrodes 3050L, 3050R may be in the range of about 0.1 mm to about 20 mm, preferably in the range of about 0.5 mm to about 5 mm, more preferably in the range of about 1 mm to about 3 mm. In another example aspect, the length 3072 of the gap between the first set of electrodes 3040L, 3040R and the second set of electrodes 3050L, 3050R may have any other suitable length. The total length 3080 of the first set of electrodes 3040L, 3040R, the second set of electrodes 3050L, 3050R, and the gap may be in the range of about 20 mm to about 210 mm, preferably in the range of about 60 mm to about 100 mm, more preferably in the range of about 50 mm to about 70 mm.

In an example aspect, the first set of electrodes 3040L, 3040R and the second set of electrodes 3050L, 3050R may be electrically coupled to the wider electrical conductors 1168 from which the first set of electrodes 3040L, 3040R and the second set of electrodes 3050L, 3050R may receive the electrosurgical energy (e.g., RF energy). The first set of electrodes 3040L, 3040R and the second set of electrodes 3050L, 3050R may be electronically coupled to a plurality of electrical conductors (e.g., electrical conductors 1732L and 1732R) on the flex circuit 3020 through which the wider electrical conductors 1168 may provide the RF energy to the electrodes 3040L, 3040R, 3050L, 3050R. In an example aspect, each of the electrodes 3040L, 3040R, 3050L, 3050R may be separately connected to the control circuit (e.g., micro-chip 1740) through a different electrical conductor. For example, a first electrical conductor of the left electrical conductors 1732L may be connected to the electrode 3040L and a second electrical conductor of the left electrical conductors 1732L may be connected to the electrode 3050L. Similarly, a first electrical conductor of the right electrical conductors 1732R may be connected to the electrode 3040R and a second electrical conductor of the right electrical conductors 1732R may be connected to the electrode 3050R.

In an example aspect, the jaw 3000 may include a multiplexer to individually address the electrodes 3040L, 3040R, 3050L, 3050R. The multiplexer may be included in the control circuit (e.g., microprocessor 560, segmented RF circuit 1160, or distal micro-chip 1740) or located between the control circuit and the electrodes 3040L, 3040R, 3050L, 3050R. The multiplexer may distribute the electrosurgical energy to the electrodes 3040L, 3040R, 3050L, 3050R under the control of the control circuit. In an example aspect, the multiplexer may be configured to detect a short of the electrodes 3040L, 3040R, 3050L, 3050R, for example, caused by a metal staple line or other electrically conductive object left in the tissue from a previous instrument firing or surgical procedure, and the electrosurgical energy could be modulated in a manner appropriate for the short circuit. In an example aspect, the electrical conductors 1168, 1732L, 1732R may be insulated to protect components (e.g., a microchip 1740, a spine assembly 1250, laminated plates 1322, a flex circuit 3020) adjacent the electrical conductors 1168, 1732L, 1732R from inadvertent RF energy. In an example aspect, the cartridge 3010 may be interchangeable. When changing the cartridge, the narrow and wider electrical conductors 1166, 1168 in the surgical instrument may be connected to the new electrical conductors and electrodes in the new cartridge.

In an example aspect, the cutting member (e.g., knife member 1330) may be directly or indirectly coupled with a motor (e.g., motor 505). When the control circuit provides voltage to the motor, the cutting member may be advanced to the first zone 3060 or the second zone 3065 to cut the tissue in the first and second zones 3060, 3065.

Figure 20:
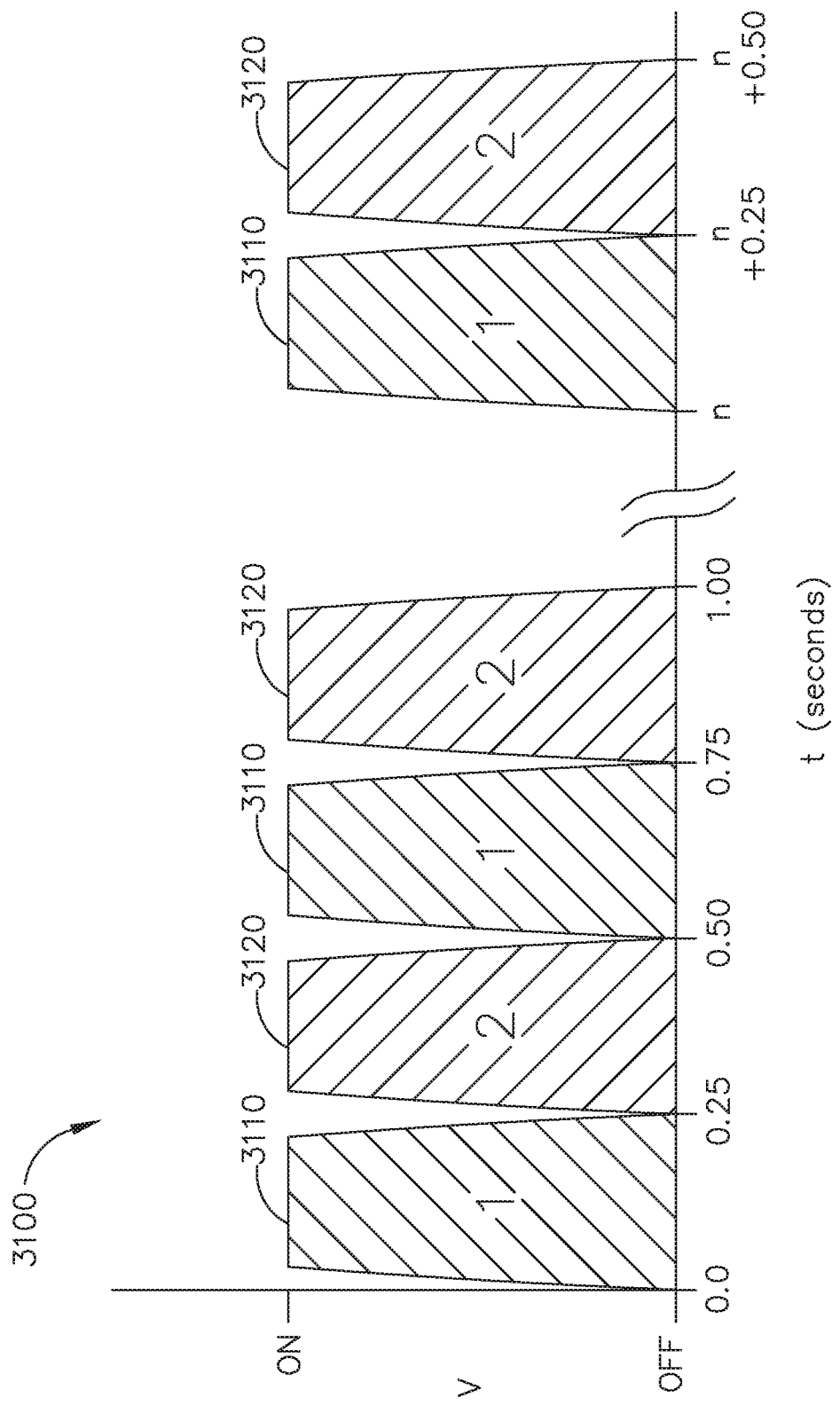
FIG. 20 is a graph depicting voltage applied to electrodes as a function of time according to one aspect of this disclosure.

FIG. 20 shows a graph 3100 depicting voltage applied to electrodes 3040L, 3040R, 3050L, 3050R as a function of time in accordance with a non-limiting aspect. The pulses 3110 may represent the voltage applied to the electrodes 3040L, 3040R in the first zone 3060. The pulses 3120 may represent the voltage applied to the electrodes 3050L, 3050R in the second zone 3065. When the voltage is on for the first zone 3060, electrosurgical energy may be applied to the tissue adjacent to the first set of electrodes 3040L, 3040R to form a coagulation/welding line there. Similarly, when the voltage is on for the second zone 3065, electrosurgical energy may be applied to the tissue adjacent to the second set of electrodes 3050L, 3050R to form a coagulation/welding line there. As shown in FIG. 20, in an example aspect, the control circuit may apply a set voltage alternatively throughout the alternation cycles. Then, the power/energy applied to the tissue may change as the tissue impedance changes. In another example aspect, the control circuit or the generator 400 may change the voltage applied to the electrodes (e.g., 30 volts for the first 5 cycles, 50 volts for the next 5 cycles, 80 volts for the next 5 cycles). In another example aspect, the control circuit or the generator 400 may change the voltage applied to the electrodes to provide a constant power to the tissue. In this case, the voltage may change as the tissue impedance changes.

In an example aspect, the electrosurgical energy may repeatedly alternate between the first set of electrodes 3040L, 3040R and the second set of electrodes 3050L, 3050R at a predetermined time interval. For example, the electrosurgical energy may be provided to the first set of electrodes 3040L, 3040R for a first period of time (e.g., 0.25 seconds) and, then, to the second set of electrodes 3050L, 3050R for a second period of time (e.g., 0.25 seconds). Then, it may be switched back to the first set of electrodes 3040L, 3040R and the alternation of the electrosurgical energy between the first set of electrodes 3040L, 3040R and the second set of electrodes 3050L, 3050R may be repeated, for example, until the impedance of the clamped tissue reaches a predetermined impedance value. In an example aspect, the predetermined time interval may be in the range of from about 0.05 seconds to about 0.5 seconds, preferably in the range of about 0.1 seconds to about 0.4 seconds, more preferably in the range of about 0.2 seconds to about 0.3 seconds. In another example aspect, the predetermined time interval may have any other suitable time period. In an example aspect, the predetermined time interval for the alternation of the electrosurgical energy may be sufficiently fast enough that the providing of the electrosurgical energy to the first set of electrodes 3040L, 3040R and the second set of electrodes 3050L, 3050R may appear to be simultaneous.

In an example aspect, the alternation of the electrosurgical energy may be started once the onboard on/off power switch 420 is turned on and may continue the alternation without an input from a user of the electrosurgical device until the onboard on/off power switch 420 is turned off. The onboard on/off power switch 420 may be automatically turned off when the measured tissue impedance reaches a predetermined impedance value (e.g., an impedance value indicating that the clamped tissue is completely sealed). The number of cycles (e.g., n times) of the alternation of the electrosurgical energy that is necessary for reaching the predetermined impedance value may vary depending on various parameters, including tissue type, tissue thickness, how much moisture is in the tissue, etc.

In an example aspect, as shown in FIG. 20, the time interval for the first set of electrodes 3040L, 3040R may be the same as the time interval for the second set of electrodes 3050L, 3050R. In another example aspect, the time interval for the first set of electrodes 3040L, 3040R may be different from the time interval for the second set of electrodes 3050L, 3050R. For example, the time interval for the first set of electrodes 3040L, 3040R may be 0.3 seconds, while the time interval for the second set of electrodes 3050L, 3050R may be 0.2 seconds. That is, in this case, the electrosurgical energy may be provided to the first set of electrodes 3040L, 3040R for 0.3 seconds, then to the second set of electrodes 3050L, 3050R for 0.2 seconds, then repeat this alternation. In an example aspect, the predetermined time interval may decrease over time. For example, the predetermined time interval may be 0.3 seconds in the beginning (e.g., for a couple of cycles), 0.2 seconds after then (for the next couple of cycles), 0.1 seconds after then (for the next couple of cycles before the tissue starts to complete to weld or is welded). In another example aspect, the predetermined time interval may increase over time.

Figure 21:
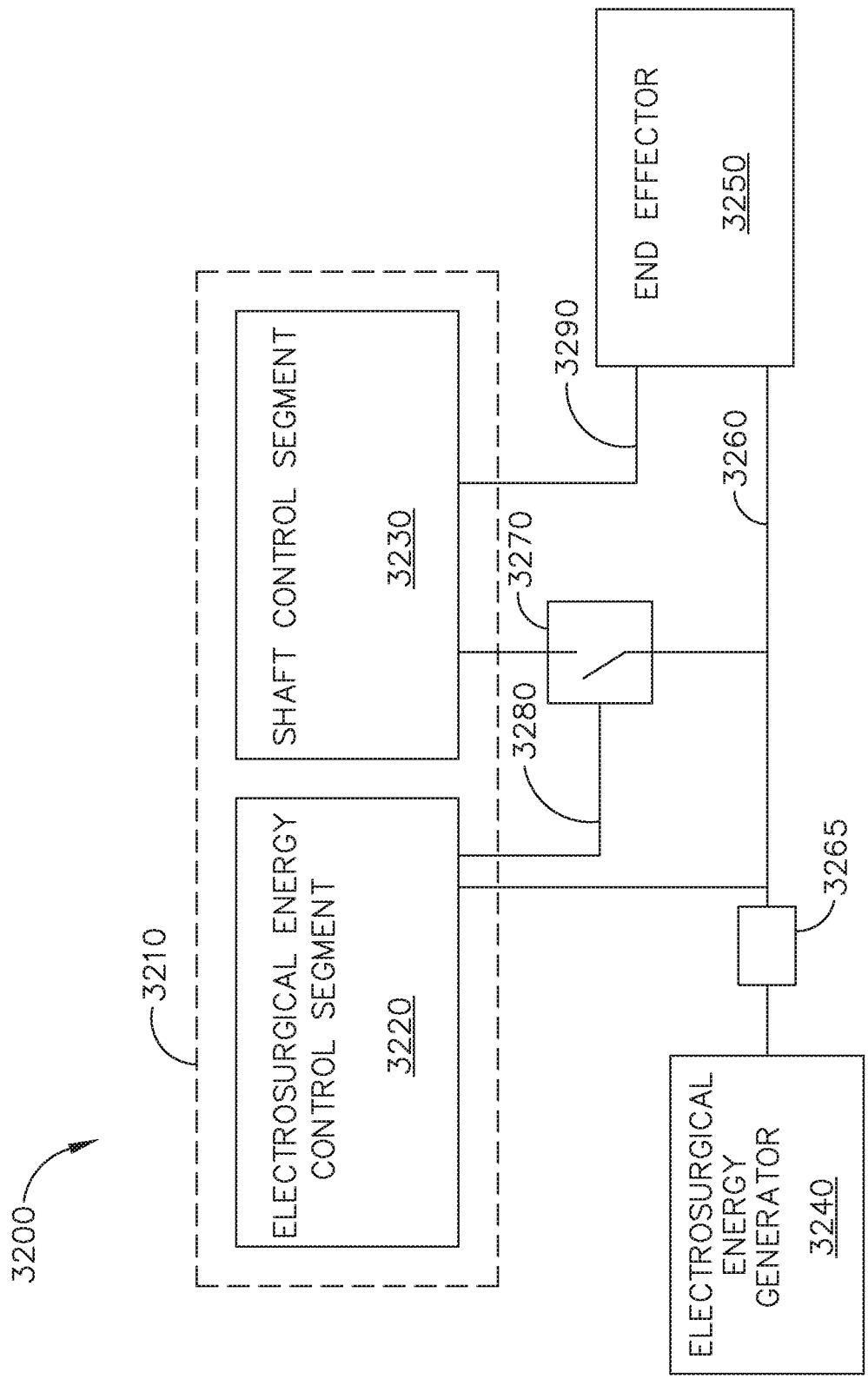
FIG. 21 illustrates a block diagram of a surgical system programmed to communicate power and control signals with an end effector according to one aspect of this disclosure.

FIG. 21 illustrates a block diagram of a surgical system 3200 programmed to communicate power and control signals with an end effector 3250 according to one aspect of this disclosure. In an example aspect, the surgical system 3200 may include a control circuit 3210 (e.g., microprocessor 560, segmented RF circuit 1160, or distal micro-chip 1740) having an electrosurgical energy control segment (or an RF energy control segment) 3220 and a shaft control segment 3230 (e.g., shaft segment (Segment 5), motor circuit segment (Segment 7), or power segment (Segment 8)). The control circuit 3210 may be configured to provide electrosurgical energy (e.g., RF energy) to the electrodes (e.g., electrodes 3040L, 3040R, 3050L, 3050R) in the end effector 3250 (e.g., end effector 1500). The surgical system 3200 may include one or more electrical conductors 3260 (e.g., electrical conductors 1168) used for providing the electrosurgical energy, from an electrosurgical energy generator 3240 (e.g., RF generator 400), to the effector 3250. The one or more electrical conductors 3260 may be electrically connected between the end effector 3250 and the control circuit 3210 (e.g., the electrosurgical energy control segment 3220 and the shaft control segment 3230). The shaft control segment 3230 may store shaft control programs in a memory and controls sensors and outputs, for example.

The electrosurgical energy control segment 3220 may be configured to provide the electrosurgical energy to the electrodes through the one or more electrical conductors 3260. In an example aspect, the shaft control segment 3230 may be configured to provide and/or receive a control signal to/from the end effector 3250 (and/or the surgical tool assembly 1000, the shaft assembly 704) through the one or more electrical conductors 3260. That is, the one or more electrical conductors 3260 may be used not only for providing the electrosurgical energy to the end effector 3250, but also for communicating control signals with the end effector 3250. In an example aspect, at least some portions of the electrosurgical energy control segment 3220 and the shaft control segment 3230 may be electrically isolated from each other.

In an example aspect, the electrosurgical energy control segment 3220 may electrically isolate the one or more electrical conductors 3260 from the shaft control segment 3230, for example, when providing the electrosurgical energy to the electrodes in the end effector 3250 through the one or more electrical conductors 3260. In an example aspect, the electrosurgical energy control segment 3220 may control a switch 3270 located between the one or more electrical conductors 3260 and the shaft control segment 3230 by providing a signal through a control line 3280 to electrically isolate the one or more electrical conductors 3260 from the shaft control segment 3230. The switch 3270 may be configured to switch between an open state and a closed state. The shaft control segment 3230 and the one or more electrical conductors 3260 may be electrically isolated when the switch 3270 is in the open state, and may be in electrical communication when the switch 3270 is in the closed state. In another example aspect, the electrosurgical energy control segment 3220 may electrically isolate the one or more electrical conductors 3260 from the shaft control segment 3230 in any other suitable manner. Other configurations of the switch 3270 may enable electrical isolation of the one or more electrical conductors 3260 from the shaft control segment 3230 by closing the switch 3270.

In an example aspect, the electrosurgical energy control segment 3220 may electrically isolate the one or more electrical conductors 3260 from the shaft control segment 3230 when the control circuit 3210 detects that the electrosurgical energy generator 3240 is connected to the connector 3265 (e.g., female connectors 410), for example, by continuously checking the connector 3265 or sensing the application of the electrosurgical energy. For example, when the male plug assembly 406 is plugged into the female connectors 410, the electrosurgical energy control segment 3220 may isolate the electrical conductors 3260 from the shaft control segment 3230. In another example aspect, the electrosurgical energy control segment 3220 may electrically isolate the one or more electrical conductors 3260 from the shaft control segment 3230 when the electrosurgical energy is provided to the end effector 3250 or at any other suitable moment.

In an example aspect, the surgical system may include one or more electrical conductors 3290 (e.g., electrical conductors 1166) used for operating the end effector 3250 (and/or the surgical tool assembly 1000, the shaft assembly 704). In an example aspect, the one or more electrical conductors 3290 may not be used to deliver the electrosurgical energy to the end effector 3250. The shaft control segment 3230 may be programmed to provide and/or receive a control signal to/from the end effector 3250 through the one or more electrical conductors 3290. In an example aspect, the shaft control segment 3230 may use the one or more electrical conductors 3290 to provide and/or receive the control signal to/from the end effector 3250 while the switch 3270 is in an open state (e.g., while the electrosurgical energy control segment 3220 is providing the electrosurgical energy to the end effector 3250 through the one or more electrical conductors 3260). In an example aspect, the shaft control segment 3230 also may use the one or more electrical conductors 3290 to provide and/or receive the control signal to/from the end effector 3250 while the switch 3270 is in a closed state.

The switch 3270 may be a transistor switch, a mechanical switch, electromechanical, relay, or any other suitable switch. In an example aspect, the control signals communicated between the control circuit 3210 and the end effector 3250 (and/or the surgical tool assembly 1000, the shaft assembly 704) through the electrical conductors 3260, 3290 include, but are not limited to, signals for driving the end effector 3250 (and/or the surgical tool assembly 1000, the shaft assembly 704) in cutting and/or coagulation operating modes, measuring electrical characteristics of the surgical system 3200 and/or the tissue clamped in the end effector 3250, providing feedback to use, communicating sensor signals, and identifying certain characteristics of the end effector 3250 (e.g., used/unused status).

Accordingly, aspects of the present disclosure may advantageously reduce the number of electrical conductors necessary for communicating control signals between the control circuit 3210 and the end effector 3250 (and/or the surgical tool assembly 1000, the shaft assembly 704) by using some of the electrical conductors (e.g., electrical conductors 3260) used for the delivery of the electrosurgical energy to communicate the control signals when those electrical conductors are not used for the electrosurgical energy. Moreover, by isolating those electrical conductors from other circuit segments (e.g., shaft control segment 3230) when providing the electrosurgical energy through those electrical conductors, aspects of the present disclosure may prevent the electrosurgical energy from flowing into the other circuit segments and/or electrical conductors (e.g., electrical conductors 3290) connected to those circuit segments, preventing damages to those circuit segments and/ore electrical conductors.

In an example aspect, the control circuit may include two operation modes, Mode I and Mode II. In Mode I, the control circuit may cut the tissue when or after the welding of the tissue is completed. In Mode 2, the control circuit may cut the tissue while the welding of the tissue is in progress. Examples of these modes are described in greater detail below and as shown in FIGS. 22-27.

Figure 22:
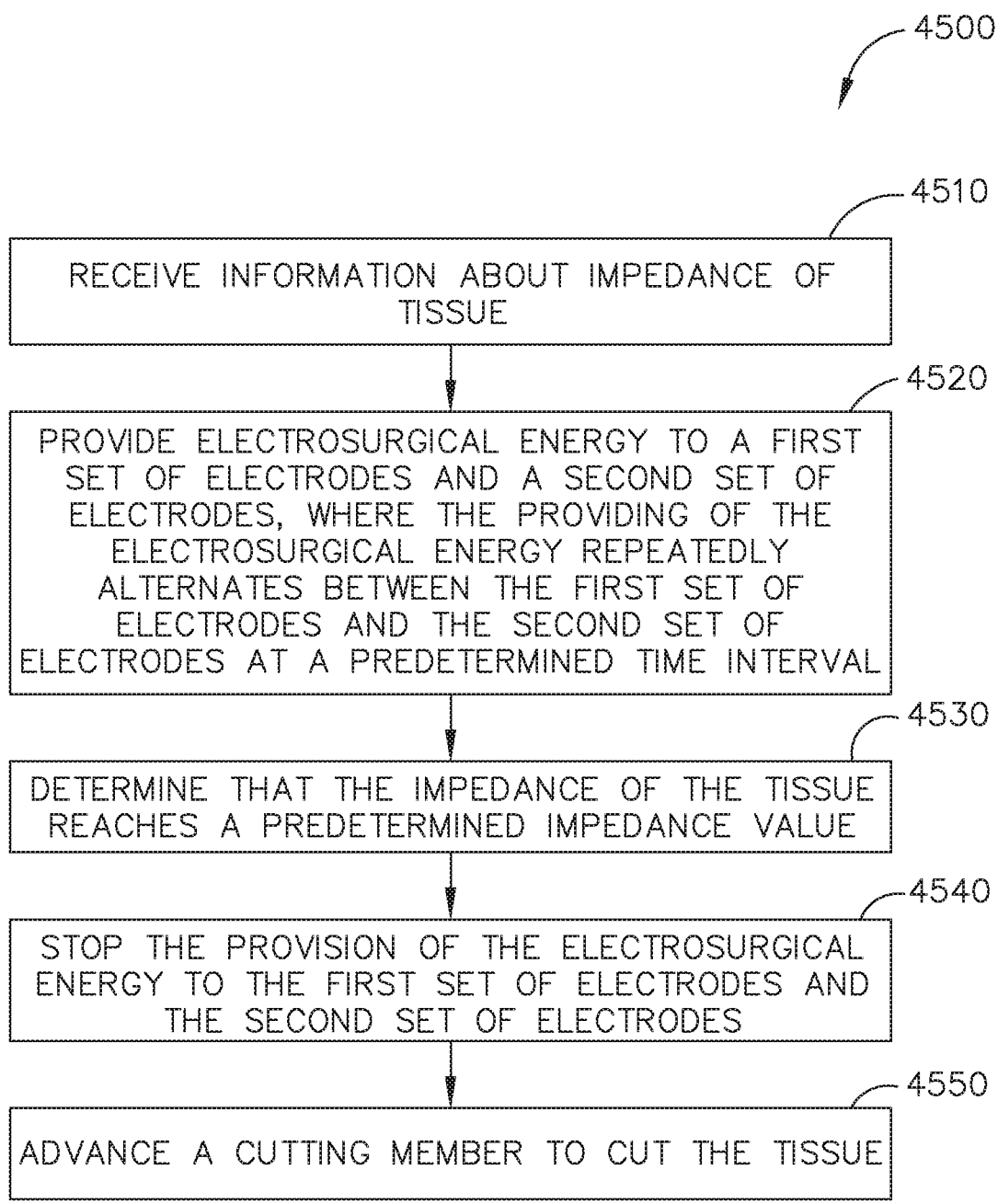
FIG. 22 is a logic flow diagram depicting a process of a control program or a logic configuration for operating the surgical instrument according to one aspect of this disclosure.

FIG. 22 s a logic flow diagram depicting a process 4500 of a control program or a logic configuration for operating the surgical instrument in accordance with Mode I. Although the example process 4500 is described with reference to the logic flow diagram illustrated in FIG. 22, it will be appreciated that many other methods of performing the acts associated with the method may be used. For example, the order of some of the blocks may be changed, certain blocks may be combined with other blocks, and some of the blocks described are optional.

In the illustrated example and with reference also to FIG. 18, a control circuit 610 (FIG. 18), may receive 4510 information about impedance of tissue. For example, the control circuit 610 may include an impedance feedback circuit and measure the impedance of the tissue clamped in the end effector 602 (e.g., end effector 1500) such as, for example, the tissue adjacent the first set of electrodes 3040L, 3040R and the second set of electrodes 3050L, 3050R. In an example aspect, the control circuit 610 may measure the tissue impedance periodically (e.g., every 0.1 seconds, every 0.5 seconds, or every second). In another example aspect, the control circuit 610 may measure the tissue impedance randomly or in any other suitable manner. The control circuit 610 may provide 4520 electrosurgical energy to a first set of electrodes and a second set of electrodes, where the providing of the electrosurgical energy repeatedly alternates between the first set of electrodes and the second set of electrodes at a predetermined time interval. For example, the control circuit 610 may provide electrosurgical energy to the first set of electrodes 3040L, 3040R and a second set of electrodes 3050L, 3050R alternatively at a predetermined time interval as described above with regard to FIG. 20.

Then, at some points, the control circuit 610 may determine 4530 that the impedance of the tissue reaches a predetermined impedance value. For example, the predetermined impedance value may be a value indicating that the tissue adjacent the first set of electrodes 3040L, 3040R and the second set of electrodes 3050L, 3050R is substantially or completely welded or coagulated. The control circuit 610 may determine that the welding of the tissue is substantially completed by comparing the measured tissue impedance with the predetermined termination impedance value. Then, the control circuit 610 may stop 4540 the provision of the electrosurgical energy to the first set of electrodes and the second set of electrodes. Then, the control circuit 610 may advance 4550 a cutting member, such as the I-beam 614, to cut the tissue. In an example aspect, the control circuit 610 may advance the cutting member (e.g., I-beam 614) to the first zone 3060 to cut the tissue in the first zone 3060 and, then, to the second zone 3065 to cut the tissue in the second zone 3065. In another example aspect, the control circuit 610 may cut the tissue in the first zone 3060 and the second zone 3065 at the same time.

FIG. 23 shows a graph 4600 of a tissue impedance curve 4605 as a function of time. The tissue impedance curve 4605 may represent a change in the impedance of the tissue claimed in the end effector 1500 when the control circuit 610 (FIG. 18) is operating in Mode I. As shown in FIG. 23, the tissue impedance tends to follow a common "bathtub" pattern, decreasing in the beginning of the energy alternation for a first time period 4625 (e.g., 0.3-1.5 seconds), reaching a minimum impedance value $(Z_M)$ at a first time $(t_1)$ 4615 and, then, increasing during a second time period 4630 (e.g., 0.3-1.5 seconds) as the clamped tissue is being welded. Then, the tissue impedance may reach a point 4610 at a second time $(t_2)$ 4620, where the tissue impedance at the point 4610 is equal to a predetermined termination impedance $(Z_T)$.

In the first period of time 4625, the tissue impedance drops from an initial value and decreases, e.g., has a negative slope, until it reaches the minimum impedance value $(Z_M)$ because after energy is applied to the tissue for a certain period the moisture content of the tissue evaporates causing the tissue to dry out and causes the tissue impedance to begin rising, e.g., positive slope, after then in the second period of time 4630 until the tissue impedance reaches the predetermined termination impedance $Z_T$, at which point in time the energy to the end effector may be shut off. In an example aspect, the tissue impedance may maintain the minimum impedance $Z_M$ for a certain period of time (e.g., 0.5-5 seconds), where the tissue impedance curve 4605 almost flattens out for that period of time. If the electrosurgical energy (e.g., RF energy) were to be applied continuously instead of being shut off at the termination impedance point 4610, the tissue impedance may increase continuously passing the point 4610.

In an example aspect, the predetermined termination impedance $(Z_T)$ may correspond to a point where the tissue adjacent the electrodes 3040L, 3040R, 3050L, 3050R may be substantially or completely welded so as to cut the tissue (e.g., blood vessel) without bleeding. The predetermined termination impedance may be stored in a memory device of the surgical instrument (e.g., surgical system 10 or surgical tool assembly 1000).

When the tissue impedance reaches the predetermined termination impedance, the control circuit may stop providing the electrosurgical energy to the first set of electrodes 3040L, 3040R and the second set of electrodes 3050L, 3050R, resulting in the sudden drop of the tissue impedance at $t_2$ 4620. In an example aspect, this sudden drop of the tissue impedance may occur because the control circuit stops measuring the tissue impedance when the provision of the electrosurgical energy is stopped. As shown in FIG. 24 depicting a graph 4650 of an example motor voltage curve, when or after the provision of the electrosurgical energy is stopped at $t_2$, the control circuit may provide voltage 4660 to the motor (e.g., motor 505) to cut the tissue in the first zone 3060. Then, the control circuit also may provide voltage 4670 to the motor to cut the tissue in the second zone 3065. As shown in FIGS. 22 and 23, in Mode I, the cutting of the clamped tissue may start during a third time period 4635 after the tissue impedance reaches the predetermined termination impedance value (e.g., completion of the tissue welding).

Figure 25:
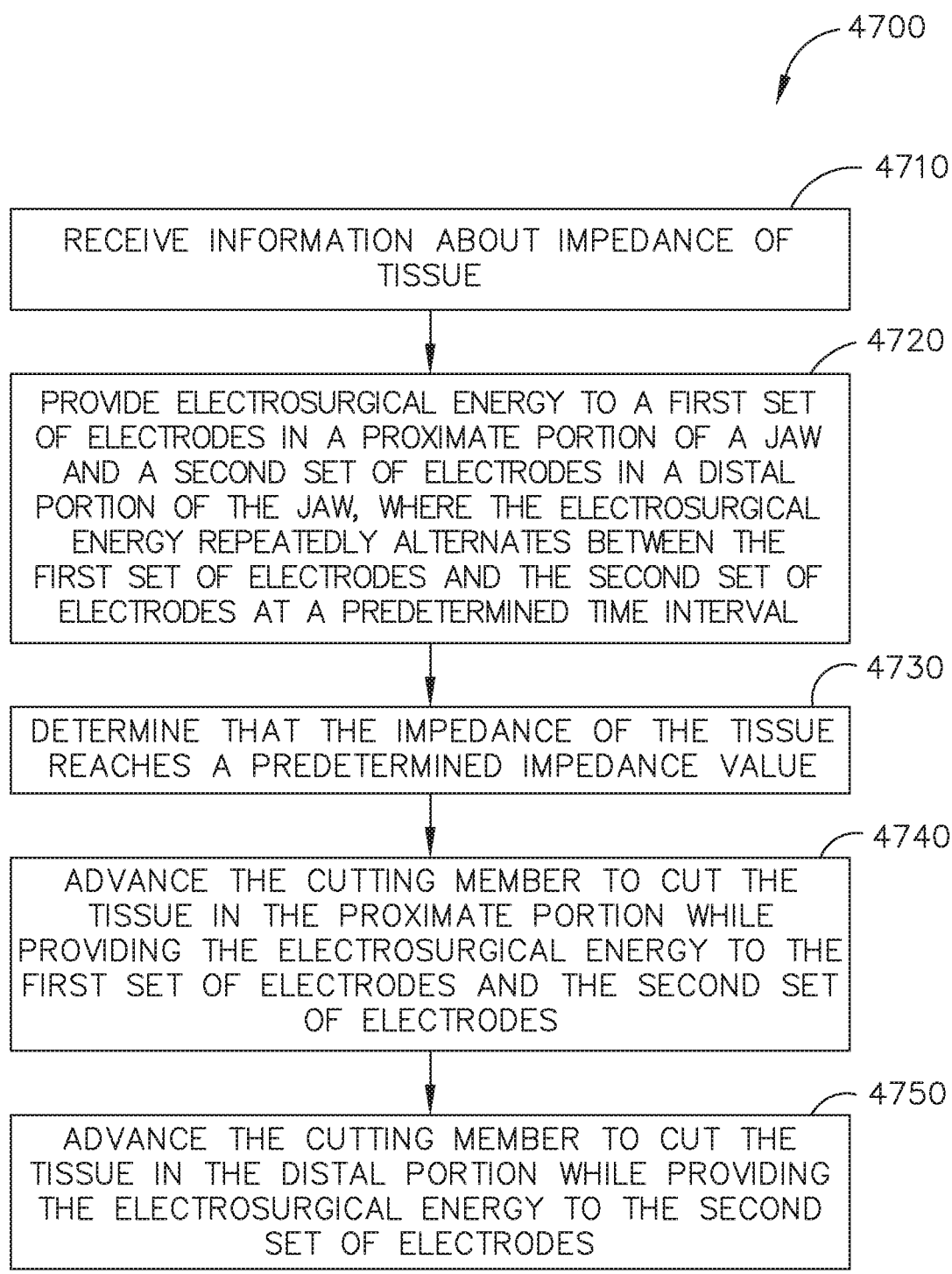
FIG. 25 is a logic flow diagram depicting a process of a control program or a logic configuration for operating the surgical instrument according to one aspect of this disclosure.

FIG. 25 is a logic flow diagram depicting a process 4700 of a control program or a logic configuration for operating the surgical instrument in accordance with Mode II. Although the example process 4700 is described with reference to the logic flow diagram illustrated in FIG. 24, it will be appreciated that many other methods of performing the acts associated with the method may be used. For example, the order of some of the blocks may be changed, certain blocks may be combined with other blocks, and some of the blocks described are optional.

In the illustrated example and with reference also to FIG. 18, a control circuit 610 may receive 4710 information about impedance of tissue. For example, the control circuit 610 may measure the impedance of the tissue clamped in the end effector 602 (e.g., end effector 1500). In an example aspect, the control circuit 610 may measure the tissue impedance periodically (e.g., every 0.1 seconds, every 0.5 seconds, or every second). In another example aspect, the control circuit 610 may measure the tissue impedance randomly or in any other suitable manner. The control circuit 610 may provide 4720 electrosurgical energy to a first set of electrodes in a proximate portion of a jaw and a second set of electrodes in a distal portion of the jaw, where the providing of the electrosurgical energy repeatedly alternates between the first set of electrodes and the second set of electrodes at a predetermined time interval. For example, the control circuit 610 may provide electrosurgical energy to the first set of electrodes 3040L, 3040R and the second set of electrodes 3050L, 3050R alternatively at a predetermined time interval as described above with regard to FIG. 20.

Then, at some points, the control circuit 610 may determine 4730 that the impedance of the tissue reaches a predetermined impedance value. For example, the predetermined impedance value may be a value indicating that welding of the tissue adjacent the first set of electrodes 3040L, 3040R and the second set of electrodes 3050L, 3050R starts to complete. Then, the control circuit 610 may advance 4740 the cutting member such as the I-beam 614 to cut the tissue in the proximate portion while providing the electrosurgical energy to the first set of electrodes and the second set of electrodes. After cutting the tissue in the proximate portion of the jaw, the control circuit 610 may advance 4740 the cutting member (e.g., I-beam 614) to cut the tissue in the distal portion while providing the electrosurgical energy to the second set of electrodes.

In an example aspect, the control circuit 610 may advance 4750 the cutting member (e.g., I-beam 614) to cut the tissue in the distal portion while providing the electrosurgical energy to both the first set of electrodes 3040L, 3040R and the second set of electrodes 3050L, 3050R. In another example aspect, the control circuit 610 may stop providing the electrosurgical energy to the first set of electrodes after cutting the tissue in the proximate portion, and provide the electrosurgical energy only to the second set of electrodes while cutting the tissue in the distal portion. In this case, the provision of the electrosurgical energy to the second set of electrodes 3050L, 3050R may still be discontinuous. For example, the electrosurgical energy may be provided to the second set of electrodes 3050L, 3050R for a set period of time (e.g., 0.25 seconds) and, then, no electrosurgical energy may be provided to the second set of electrodes 3050L, 3050R for the next set period of time (e.g., 0.25 seconds) and, then the electrosurgical energy may be provided to the second set of electrodes 3050L, 3050R for the next set period of time (e.g., 0.25 seconds). This may be repeated while cutting the tissue in the distal portion of the jaw (e.g., the second zone 3065).

In another example aspect, the control circuit 610 may stop providing the electrosurgical energy to the first set of electrodes 3040L, 3040R and the second set of electrodes 3050L, 3050R after cutting the tissue in the first zone. In this case, no electrosurgical energy may be provided to the tissue while cutting the tissue in the second zone 3065. In an example aspect, the control circuit 610 may stop providing the electrosurgical energy to the first set of electrodes 3040L, 3040R and the second set of electrodes 3050L, 3050R when the tissue impedance reaches a predetermined termination impedance value while cutting the tissue in the first zone 3060 and/or the second zone 3065.

FIG. 26 shows a graph 4800 of a tissue impedance curve 4805 as a function of time. The tissue impedance curve 4805 may represent a change in the impedance of the tissue claimed in the end effector 1500 when the control circuit is operating in Mode II. As seen in FIG. 23, the tissue impedance here also tends to follow a common "bathtub" pattern, decreasing in the beginning of the energy alternation (e.g., between the first set of electrodes 3040L, 3040R and the second set of electrodes 3050L, 3050R) for a first time period 4835 (e.g. 0.3-1.5 seconds), reaching a minimum impedance value $(Z_M)$ at a first time $(t_1)$ 4820 and, then, increasing during a second time period 4840 (e.g., 0.3-1.5 seconds). As explained above, in the first period of time 4835, the tissue impedance drops from an initial value and decreases, e.g., has a negative slope, until it reaches the minimum impedance value $(Z_M)$ because after energy is applied to the tissue for a certain period the moisture content of the tissue evaporates causing the tissue to dry out and causes the tissue impedance to begin rising, e.g., positive slope, after then in the second period of time 4840 until the tissue impedance reaches the termination impedance $Z_{T1}$. In an example aspect, the tissue impedance may maintain the minimum impedance for a period of time (e.g., 0.5-5 seconds), where the tissue impedance curve 4805 almost flattens out for that period of time.

In an example aspect, when the tissue impedance reaches the minimum impedance value $(Z_M)$, a rate of impedance change (e.g., decrease) may become approximately zero as shown in FIG. 23. The welding of the clamped tissue may start to complete at this point. In an example aspect, in Mode II, the control circuit may start advancing the cutting member when the tissue impedance reaches the minimum impedance value $(Z_M)$. For example, the control circuit may determine that the tissue impedance reaches the minimum impedance value $(Z_M)$ when the rate of impedance change (e.g., decrease) becomes approximately zero. In another example aspect, in Mode II, the control circuit may start advancing the cutting member at any other suitable time before the clamped tissue is completely welded. If the tissue impedance maintains the minimum impedance for a period of time (e.g., 0.5-5 seconds), the control circuit may start advancing the cutting member at any suitable moment during that period of time (e.g., in the beginning/middle/end of the flat curve).

As shown in FIG. 27, and with reference also to FIG. 18, the control circuit 610 may provide voltage 4860 to the motor 604 (e.g., motor 505) to cut the tissue in the first zone 3060 when or after the tissue impedance reaches the minimum impedance value $(Z_M)$ before the tissue welding is completed. The termination impedance $Z_{T1}$ may represent the tissue impedance at the completion of the cutting at a second time $(t_2)$ 4825. Then, the control circuit may provide voltage 4870 to the motor 604 (e.g., motor 505) to cut the tissue in the second zone 3065 after cutting the tissue in the first zone 3060. The termination impedance $Z_{T2}$ may represent the tissue impedance at the completion of the cutting at a third time $(t_3)$ 4830. The impedance curve 4805 may drop near at the second time 4825 right after the cutting of the tissue in the first zone 3060 because the clamped tissue may be wet with some fluids (e.g., blood or any other body fluids) that are produced while cutting the tissue in the first zone 3060. Thus, although the measured impedance value 4805 may appear to drop after the cutting of the tissue in the first zone 3060, the actual tissue impedance may not drop, but may be similar to or higher than $Z_{T1}$ throughout the third time period 4845. As the moisture content of the tissue evaporates causing the tissue to dry out because of the electrosurgical energy applied to the clamped tissue during the third time period 4845, the measured impedance value also may increase quickly to reflect the actual tissue impedance.

In an example aspect, the control circuit 610 may consider the amount of time required to cut the clamped tissue in the end effector 602 in determining when to start advancing the cutting member such as the I-beam 614. For example, if it takes 1 second to cut the tissue in the first zone 3060, the control circuit 610 may start advancing the cutting member (e.g. I-beam 614) around 1 second before the tissue impedance reaches a predetermined termination impedance value (where around this time the tissue welding is normally completed) such that the tissue welding is substantially completed by the time the cutting of the tissue in the first zone 3060 is completed. In another example aspect, the cutting speed may be adjusted so that the tissue welding is substantially completed by the end of the cutting. For example, if it takes 0.5 seconds from the moment the tissue impedance reaches the minimum impedance to the moment it reaches the termination impedance (e.g., where the tissue welding is completed), the cutting speed may be adjusted so that it would take 0.5 seconds to cut the tissue in the first or second zones 3060, 3065.

As explained above, in an example aspect, the control circuit 610 may provide the electrosurgical energy to both the first set of electrodes 3040L, 3040R and the second set of electrodes 3050L, 3050R while cutting the tissue in the second zone 3065 during the third time period 4845. In this case, since the clamped tissue received additional electrosurgical energy for the third time period 4845, the termination impedance $Z_{T2}$ at the third time 4830 may be higher than the termination impedance $Z_{T1}$ at the second time 4825 as seen in FIG. 26.

In an example aspect, the control circuit 610 may stop providing the electrosurgical energy to the first set of electrodes after cutting the tissue in the first zone 3060 and provide the electrosurgical energy only to the second set of electrodes while cutting the tissue in the second zone 3065. In this case, the termination impedance of the tissue in the second zone 3065 may be higher than the termination impedance of the tissue in the first zone 3060 since the tissue in the second zone 3065 received more electrosurgical energy for the third time period 4845 than the tissue in the first zone 3060, assuming that the predetermined time intervals for the two sets of electrodes are the same.

The functions or processes 4500, 4700 described herein may be executed by any of the processing circuits described herein, such as the control circuit 700 described in connection with FIGS. 16-17, the control circuit 610 described in connection with FIG. 18.

Aspects of the surgical instrument may be practiced without the specific details disclosed herein. Some aspects have been shown as block diagrams rather than detail. Parts of this disclosure may be presented in terms of instructions that operate on data stored in a computer memory. Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program, which at least partially carries out processes and/or devices described herein), electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components, logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a electrical conductor communications link, a electrical conductorless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

Various aspects of the subject matter described herein are set out in the following examples:

Example 1

A surgical instrument comprising: an end effector comprising: a first jaw comprising a distal portion and a proximate portion; a second jaw that is movable relative to the first jaw; and at least one electrode in the first jaw; a control circuit configured to provide electrosurgical energy to the at least one electrode, wherein the control circuit comprises a shaft control segment and an electrosurgical energy control segment; and a first electrical conductor electrically connected between the end effector and the control circuit; wherein the shaft control segment is configured to provide a control signal for operating the end effector to the end effector through the first electrical conductor; wherein the electrosurgical energy control segment is configured to provide the electrosurgical energy to the at least one electrode through the first electrical conductor.

Example 2

The surgical instrument of Example 1, wherein the electrosurgical energy control segment is electrically isolated from the shaft control segment.

Example 3

The surgical instrument of one or more of Example 1 through Example 2, wherein the electrosurgical energy control segment is configured to electrically isolate the first electrical conductor from the shaft control segment when providing the electrosurgical energy to the at least one electrode.

Example 4

The surgical instrument of Example 3, further comprising a switch electrically coupled between the electrosurgical energy control segment and the shaft control segment, wherein the electrosurgical energy control segment is configured to electrically isolate the first electrical conductor from the shaft control segment by controlling the switch.

Example 5

The surgical instrument of Example 4, wherein the electrosurgical energy control segment is configured to electrically isolate a first electrical conductor from the shaft control segment by opening a switch located between the first electrical conductor and the shaft control segment.

Example 6

The surgical instrument of one or more of Example 1 through Example 5, further comprising a second electrical conductor, wherein the shaft control segment is configured to provide the control signal to the end effector through the second electrical conductor and wherein the shaft control segment is configured to provide the control signal to the end effector through the second electrical conductor when the electrosurgical energy control segment is providing the electrosurgical energy to the at least one electrode through the first electrical conductor.

Example 7

The surgical instrument of one or more of Example 1 through Example 6, wherein the second jaw comprises an anvil.

Example 8

The surgical instrument of one or more of Example 1 through Example 7, wherein the electrosurgical energy comprises radio frequency (RF) energy.

Example 9

The surgical instrument of one or more of Example 1 through Example 8, wherein the at least one electrode comprises a first set of electrodes located in the proximate portion of the first jaw and a second set of electrodes located in the distal portion of the first jaw, and wherein electrosurgical energy segment is configured to repeatedly alternate electrosurgical energy between the first set of electrodes and the second set of electrodes at a predetermined time interval.

Example 10

The surgical instrument of Example 9, further comprising a cutting member, wherein the first jaw and the second jaw define an elongate slot therebetween extending from the proximate portion of the first jaw and wherein the cutting member is slidably receivable within the elongate slot to cut tissue located between the first jaw and the second jaw.

Example 11

The surgical instrument of Example 10, wherein the first set of electrodes comprises a first electrode and a second electrode, wherein the first electrode is located on the left side of the elongate slot and the second electrode is located on the right side of the elongate slot.

Example 12

The surgical instrument of one or more of Example 10 through Example 11, wherein the second set of electrodes comprise a third electrode and a fourth electrode, wherein the third electrode is located on the left side of the elongate slot and the fourth electrode is located on the right side of the elongate slot.

Example 13

The surgical instrument of one or more of Example 9 through Example 12, wherein the predetermined time interval comprises a first time interval for the first set of electrodes and a second time interval for the second set of electrodes, wherein the first time interval is different from the second time interval.

Example 14

The surgical instrument of one or more of Example 9 through Example 12, wherein the predetermined time interval for the alternation is sufficiently fast enough that the providing of the electrosurgical energy to the first set of electrodes and the second set of electrodes appears to be simultaneous.

Example 15

The surgical instrument of one or more of Example 9 through Example 14, wherein the predetermined time interval is in the range of from about 0.1 to 0.5 seconds.

Example 16

A surgical system comprising: a radio frequency (RF) energy generator; a handle body; an end effector comprising: a first jaw comprising a distal portion and a proximate portion; a second jaw that is movable relative to the first jaw; and at least one electrode in the first jaw; a control circuit configured to provide RF energy, from the RF energy generator, to the at least one electrode, wherein the control circuit comprises a shaft control segment and an RF control segment; and a first electrical conductor electrically connected between the end effector and the control circuit; wherein the shaft control segment is configured to provide a control signal for operating the end effector to the end effector through the first electrical conductor; wherein the RF control segment is configured to provide the RF energy to the at least one electrode through the first electrical conductor.

Example 17

The surgical system of Example 16, wherein the RF control segment is electrically isolated from the shaft control segment.

Example 18

The surgical system of one or more of Example 16 through Example 17, wherein the RF control segment is configured to electrically isolate the first electrical conductor from the shaft control segment when providing the RF energy to the at least one electrode.

Example 19

The surgical system of Example 18, further comprising a switch electrically coupled between the first electrical conductor and the shaft control segment, wherein the RF control segment is configured to electrically isolate the first electrical conductor from the shaft control segment by controlling the switch.

Example 20

The surgical instrument of Example 19, wherein the electrosurgical energy control segment is configured to electrically isolate a first electrical conductor from the shaft control segment by opening a switch located between the first electrical conductor and the shaft control segment.

Example 21

The surgical system of one or more of Example 16 through Example 20, further comprising a second electrical conductor, wherein the shaft control segment is configured to provide the control signal to the end effector through the second electrical conductor, and wherein the shaft control segment is configured to provide the control signal to the end effector to the second electrical conductor when the RF control segment is providing the RF energy to the at least one electrode through the first electrical conductor.

Example 22

The surgical system of one or more of Example 16 through Example 21, wherein the at least one electrode comprises a first set of electrodes located in the proximate portion of the first jaw and a second set of electrodes located in the distal portion of the first jaw, and wherein electrosurgical energy segment is configured to repeatedly alternate RF energy between the first set of electrodes and the second set of electrodes at a predetermined time interval.

The invention claimed is:

1. A surgical instrument comprising:
an end effector comprising:
a first jaw comprising a distal portion and a proximate portion;
a second jaw that is movable relative to the first jaw; and
at least one electrode in the first jaw;
a control circuit configured to provide electrosurgical energy to the at least one electrode, wherein the control circuit comprises a shaft control segment and an electrosurgical energy control segment; and
a first electrical conductor electrically connected between the end effector and the control circuit;
wherein the shaft control segment is configured to provide a control signal for operating the end effector to the end effector through the first electrical conductor;
wherein the electrosurgical energy control segment is configured to provide the electrosurgical energy to the at least one electrode through the first electrical conductor;
wherein the at least one electrode comprises a first set of electrodes located in the proximate portion of the first jaw and a second set of electrodes located in the distal portion of the first jaw, and wherein the electrosurgical energy control segment is configured to repeatedly alternate electrosurgical energy between the first set of electrodes and the second set of electrodes at a predetermined time interval.

2. The surgical instrument of claim 1, wherein the electrosurgical energy control segment is electrically isolated from the shaft control segment.

3. The surgical instrument of claim 1, wherein the electrosurgical energy control segment is configured to electrically isolate the first electrical conductor from the shaft control segment when providing the electrosurgical energy to the at least one electrode.

4. The surgical instrument of claim 3, further comprising a switch electrically coupled between the electrosurgical energy control segment and the shaft control segment, wherein the electrosurgical energy control segment is configured to electrically isolate the first electrical conductor from the shaft control segment by controlling the switch.

5. The surgical instrument of claim 1, wherein the electrosurgical energy control segment is configured to electrically isolate the first electrical conductor from the shaft control segment by opening a switch located between the first electrical conductor and the shaft control segment.

6. The surgical instrument of claim 1, further comprising a second electrical conductor, wherein the shaft control segment is configured to provide the control signal to the end effector through the second electrical conductor and wherein the shaft control segment is configured to provide the control signal to the end effector through the second electrical conductor but not through the first electrical conductor when the electrosurgical energy control segment is providing the electrosurgical energy to the at least one electrode through the first electrical conductor.

7. The surgical instrument of claim 1, wherein the second jaw comprises an anvil.

8. The surgical instrument of claim 1, wherein the electrosurgical energy comprises radio frequency (RF) energy.

9. The surgical instrument of claim 1, further comprising a cutting member, wherein the first jaw and the second jaw define an elongate slot therebetween extending from the proximate portion of the first jaw and wherein the cutting member is slideably receivable within the elongate slot to cut tissue located between the first jaw and the second jaw.

10. The surgical instrument of claim 9, wherein the first set of electrodes comprises a first electrode and a second electrode, wherein the first electrode is located on a left side of the elongate slot and the second electrode is located on a right side of the elongate slot.

11. The surgical instrument of claim 9, wherein the second set of electrodes comprises a third electrode and a fourth electrode, wherein the third electrode is located on a left side of the elongate slot and the fourth electrode is located on a right side of the elongate slot.

12. The surgical instrument of claim 1, wherein the predetermined time interval comprises a first time interval for the first set of electrodes and a second time interval for the second set of electrodes, wherein the first time interval is different from the second time interval.

13. The surgical instrument of claim 1, wherein the predetermined time interval for the alternation is sufficiently fast enough that the providing of the electrosurgical energy to the first set of electrodes and the second set of electrodes appears to be simultaneous.

14. The surgical instrument of claim 1, wherein the predetermined time interval is in the range of from about 0.1 to 0.5 seconds.

15. A surgical system comprising:
a radio frequency (RF) energy generator;
a handle body;
an end effector comprising:
a first jaw comprising a distal portion and a proximate portion;
a second jaw that is movable relative to the first jaw; and at least one electrode in the first jaw;

a control circuit configured to provide RF energy, from the RF energy generator, to the at least one electrode, wherein the control circuit comprises a shaft control segment and an RF control segment; and a first electrical conductor electrically connected between the end effector and the control circuit;

wherein the shaft control segment is configured to provide a control signal for operating the end effector to the end effector through the first electrical conductor;

wherein the RF control segment is configured to provide the RF energy to the at least one electrode through the first electrical conductor;

wherein the at least one electrode comprises a first set of electrodes located in the proximate portion of the first jaw and a second set of electrodes located in the distal portion of the first jaw, and wherein the RF control segment is configured to repeatedly alternate RF energy between the first set of electrodes and the second set of electrodes at a predetermined time interval.

16. The surgical system of claim 15, wherein the RF control segment is electrically isolated from the shaft control segment.

17. The surgical system of claim 15, wherein the RF control segment is configured to electrically isolate the first electrical conductor from the shaft control segment when providing the RF energy to the at least one electrode.

18. The surgical system of claim 17, further comprising a switch electrically coupled between the first electrical conductor and the shaft control segment, wherein the RF control segment is configured to electrically isolate the first electrical conductor from the shaft control segment by controlling the switch.

19. The surgical system of claim 15, wherein the RF control segment is configured to electrically isolate the first electrical conductor from the shaft control segment by opening a switch located between the first electrical conductor and the shaft control segment.

20. The surgical system of claim 15, further comprising a second electrical conductor, wherein the shaft control segment is configured to provide the control signal to the end effector through the second electrical conductor, and wherein the shaft control segment is configured to provide the control signal to the end effector through the second electrical conductor but not through the first electrical conductor when the RF control segment is providing the RF energy to the at least one electrode through the first electrical conductor.

* * * * *